United States Patent
Tumeh et al.

(10) Patent No.: US 11,275,080 B2
(45) Date of Patent: Mar. 15, 2022

(54) METHODS FOR STRATIFYING NON-RESPONDERS TO THERAPIES THAT BLOCK PD1/PDL1 AXIS

(71) Applicant: THE REGENTS OF THE UNIVERSITY OF CALIFORNIA, Oakland, CA (US)

(72) Inventors: Paul C. Tumeh, Santa Monica, CA (US); Antoni Ribas, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/933,853

(22) Filed: Nov. 5, 2015

(65) Prior Publication Data
US 2016/0123964 A1    May 5, 2016

Related U.S. Application Data

(60) Provisional application No. 62/084,484, filed on Nov. 25, 2014, provisional application No. 62/075,503, filed on Nov. 5, 2014.

(51) Int. Cl.
| | |
|---|---|
| *C07K 16/00* | (2006.01) |
| *G01N 33/50* | (2006.01) |
| *C07K 16/28* | (2006.01) |
| *A61K 39/00* | (2006.01) |

(52) U.S. Cl.
CPC ..... *G01N 33/5091* (2013.01); *C07K 16/2818* (2013.01); *A61K 2039/505* (2013.01); *C07K 2317/76* (2013.01); *G01N 2800/52* (2013.01)

(58) Field of Classification Search
CPC .............................................. A61K 2039/5056
USPC .......................................................... 435/4
See application file for complete search history.

(56) References Cited

U.S. PATENT DOCUMENTS

| | | |
|---|---|---|
| 2013/0071403 A1 | 3/2013 | Rolland et al. |
| 2016/0176962 A1 | 6/2016 | Murriel et al. |

FOREIGN PATENT DOCUMENTS

| | | |
|---|---|---|
| WO | WO2012038068 A2 | 3/2012 |
| WO | WO2012038068 A3 | 3/2012 |
| WO | WO2012038068 A8 | 3/2012 |
| WO | 2013186374 A1 | 12/2013 |
| WO | WO2016015095 A1 | 2/2016 |
| WO | WO2016061142 A1 | 4/2016 |
| WO | WO2016073760 A1 | 5/2016 |
| WO | WO2018009904 A1 | 1/2018 |

OTHER PUBLICATIONS

Peng et al (Cancer Res, 2012, 72(20): 5209-5218).*
Hamid et al (NEJM, 2013, 369(2): 134-144).*
Green et al (Blood, 2010, 116(17): 3268-3277).*
Berger et al (Clin Cancer Res, 2008, 14(10): 3044-3051).*
Chen et al (Clin Cancer Res, 2013, 19(13): 3462-3476).*
Horland et al (Cancer Sci, 2016, 107(11): 1695-1707).*
Vassilakopoulos et al (The Oncologist, 2012, 17: 239-249).*
Dowlatshahi et al (Journal of Investigative Dermatology, 2013, 133: 1879-1889).*
Brahmer et al (NEJM, 2012, 366: 2455-2465).*
Galon, Jerome et al., "Location of Immune Cells Within Human Colorectal Tumors Predict Clinical Outcome", Science, vol. 313(5795). Sep. 29, 2006, pp. 1960-1964.
Halama, Niels et al., "The localization and density of immune cells in primary tumors of human metastatic colorectal cancer shows an association with response to chemotherapy", Cancer Immunity, Feb. 19, 2009, vol. 9, p. 1-6.
Prado-Garcia, Heriberto, et al., "Tumor-Induced CD8+ T-Cell Dysfunction in Lung Cancer Patients", Hindawi Publishing Corporation, Clinical and Developmental Immunology, vol. 2012, Article ID 741741, 11 pages.
Tumeh, Paul C. et al., "PD-1 blockade induces responses by inhibiting adaptive immune resistance", Nature, vol. 515, Nov. 27, 2014, pp. 568-571.
Yano, Shuya, et al., "Spatial—temporal FUCCI imaging of each cell in a tumor demonstrates locational dependence of cell cycle dynamics and chemoresponsiveness", Cell Cycle 13:13, 2110-2119; Jul. 1, 2014.
International Search Report dated Feb. 15, 2016, from co-pending International Application PCT/US2015/059299 filed Nov. 5, 2015.
Bald, T. et al., "Immune Cell-Poor Melanomas Benefit from PD-1 Blockade after Targeted Type I IFN Activation" Cancer Discovery, 2014;4:674-687.

(Continued)

*Primary Examiner* — Sean E Aeder
(74) *Attorney, Agent, or Firm* — Karen S. Canady; canady + lortz LLP

(57) ABSTRACT

A method of analyzing a biological sample from a subject that has a tumor or cancer, comprising: determining, for target cells having a phenotype of interest spatial resolution of the target cells, density of the spatially resolved target cells in the sample; and proximity between spatially resolved target cells of interest in the sample; and determining an overall score based at least in part on the preceding parameters. A method for identifying a patient as a responder to single agent anti-PD-1 or anti-PD-L1 therapy is provided. Similar methods are provided for detecting adaptive immune resistance, the presence of cancer in a patient sample, determining efficacy of cancer therapy, and determining response to and monitoring the efficacy of cancer therapy.

17 Claims, 14 Drawing Sheets

(56) References Cited

OTHER PUBLICATIONS

Herbst, R.S. et al. "Predictive correlates of response to the anti-PD-L1 antibody MPDL3280A in cancer patients" Nature, 2014; 515:563-567.
Ribas, A. et al. "The Future of Cancer Therapy: Selecting Patients Likely to Respond to PD1/L1 Blockade" Clinical Cancer Research, American Association for Cancer Research, 2014; 4982.
Taube, J. et al. "Association of PD-1, PD-1 ligands, and other features of the tumor immune microenvironment with response to anti-PD-1 therapy" Clinical Cancer Research. Oct. 1, 2014; 20(19): 5064-5074. doi:10.1158/1078-0432. CCR-13-3271.
Totonez, M. "AACR 2015: Report from Day 5" Cancer Research Institute Blog, Apr. 22, 2015.
Galon, Jerome et al., Towards the introduction of the 'Immunoscore' in the classification of malignant tumours. J Pathol. Jan. 2014;232(2):199-209. doi: 10.1002/path.4287.
Gajewski, TF, et al., Cancer immunotherapy strategies based on overcoming barriers within the tumor microenvironment. Curr Opin Immunol. Apr. 2013;25(2):268-76. doi: 10.1016/j.coi.2013.02.009. Epub Apr. 8, 2013.
Spranger, S., et al., Mechanism of tumor rejection with doublets of CTLA-4, PD-1/PD-L1, or IDO blockade involves restored IL-2 production and proliferation of CD8+ T cells directly within the tumor microenvironment. J Immunother Cancer. 2014; 2: 3. Published online Feb. 18, 2014. doi: 10.1186/2051-1426-2-3.
Extended European Search Report dated Mar. 6, 2018 from corresponding European Application No. 15857303.0 (Publication No. EP3215852).
Denkert et al. Tumor-associated lymphocytes as an independent predictor of response to neoadjuvant chemotherapy in breast cancer, J Clin Oncol., 28(1): 105-113 (2010).
Fremd, et al. B cell-regulated immune responses in tumor models and cancer patients. Oncoimmunology. Jul. 1, 2013;2(7):e25443.
Gentles et al. The prognostic landscape of genes and infiltrating immune cells across human cancers, Nature Medicine, 21(8): 938-945 (2015).
Hanahan et al. Hallmarks of cancer: the next generation, Cell, 144(5): 646-674 (2011).
Kroeger et al. Tumor-Infiltrating Plasma Cells Are Associated with Tertiary Lymphoid Structures, Cytolytic T-Cell Responses, and Superior Prognosis in Ovarian Cancer, Clin Cancer Res., 22(12): 3005-3015 (2016).
Pardoll, et al. The blockade of immune checkpoints in cancer immunotherapy Nat Rev Cancer. Apr. 2012; 12(4):252-264.
Raje, et al. Phase 1 Study of Tabalumab, a Human Anti-B-Cell Activating Factor Antibody, and Bortezomib in Patients with Relapsed/Refractory Multiple Myeloma. Clinical Cancer Research, vol. 22, No. 23, Jun. 10, 2016 (Jun. 10, 2016), pp. 5688-5695.
Rihacek, et al. B-Cell Activating Factor as a Cancer Biomarker and Its Implications in Cancer-Related Cachexia. Biomed Res Int. 2015;2015:792187. doi: 10.1155/2015/792187. Epub Aug. 3, 2015.
Schwartz, et al. B cell regulation of the anti-tumor response and role in carcinogenesis. J Immunother Cancer. Jul. 19, 2016;4:40. doi: 10.1186/s40425-016-0145-x. eCollection 2016.
Zagouri, et al. Emerging antibodies for the treatment of multiple myeloma. Expert Opin Emerg Drugs. Jun. 2016;21(2):225-37. doi: 10.1080/14728214.2016.1186644.
International Search Report and Written Opinion for PCT/US2017/041256 (WO2018009904) dated Jan. 11, 2018.

\* cited by examiner

| Region of Interest | Green Pixels | Red Pixels | → | Proximity Call |
|---|---|---|---|---|
| ROI-1 | 0 | 13 | | Negative |
| ROI-2 | 13 | 0 | | Negative |
| ROI-3 | 13 | 13 | | Positive |
| ROI-4 | 0 | 0 | | Negative |
| ROI-5 | 7 | 3 | | Positive |

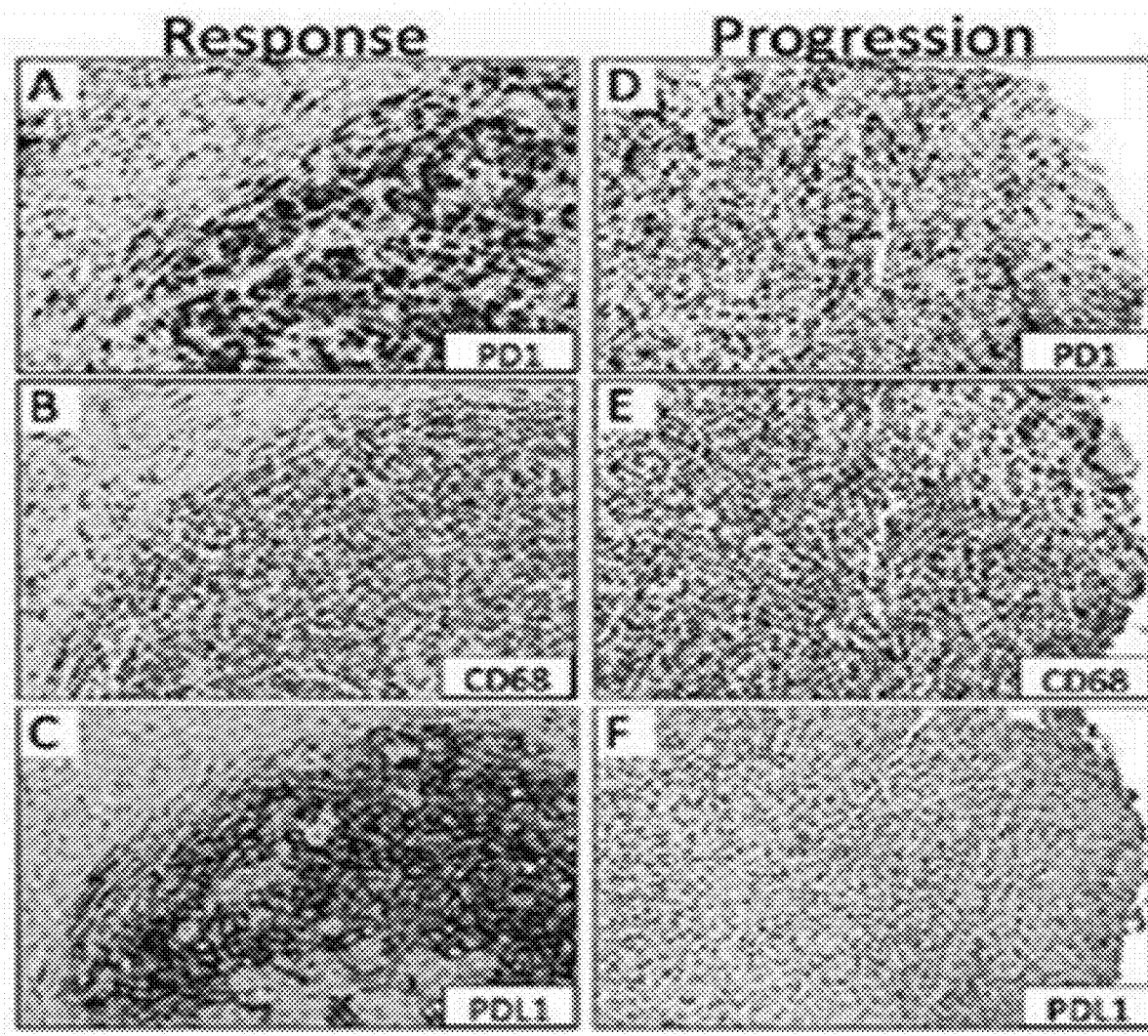
FIGURES 8A-F

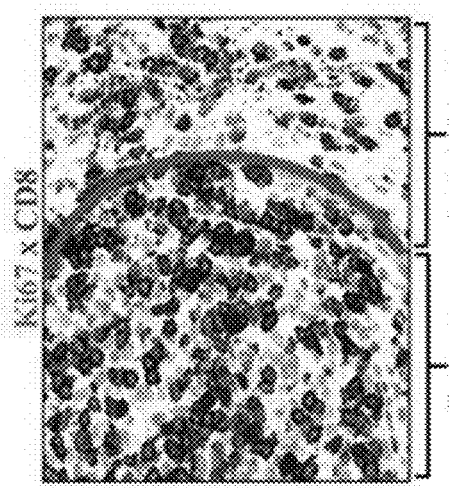
FIGURE 10A
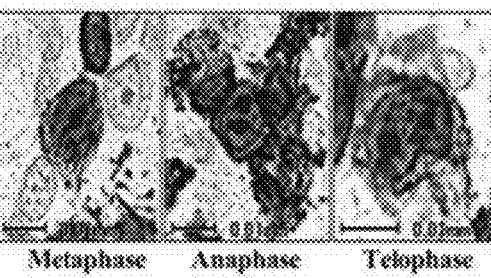
FIGURE 10B
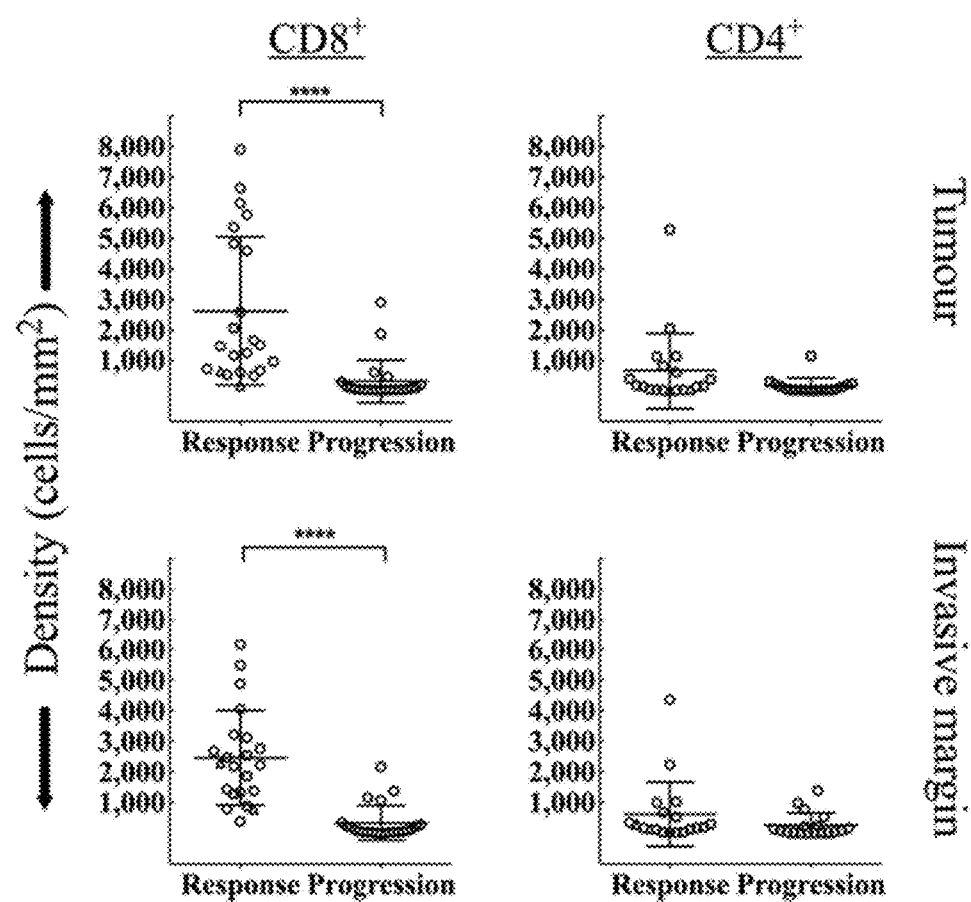
FIGURE 11

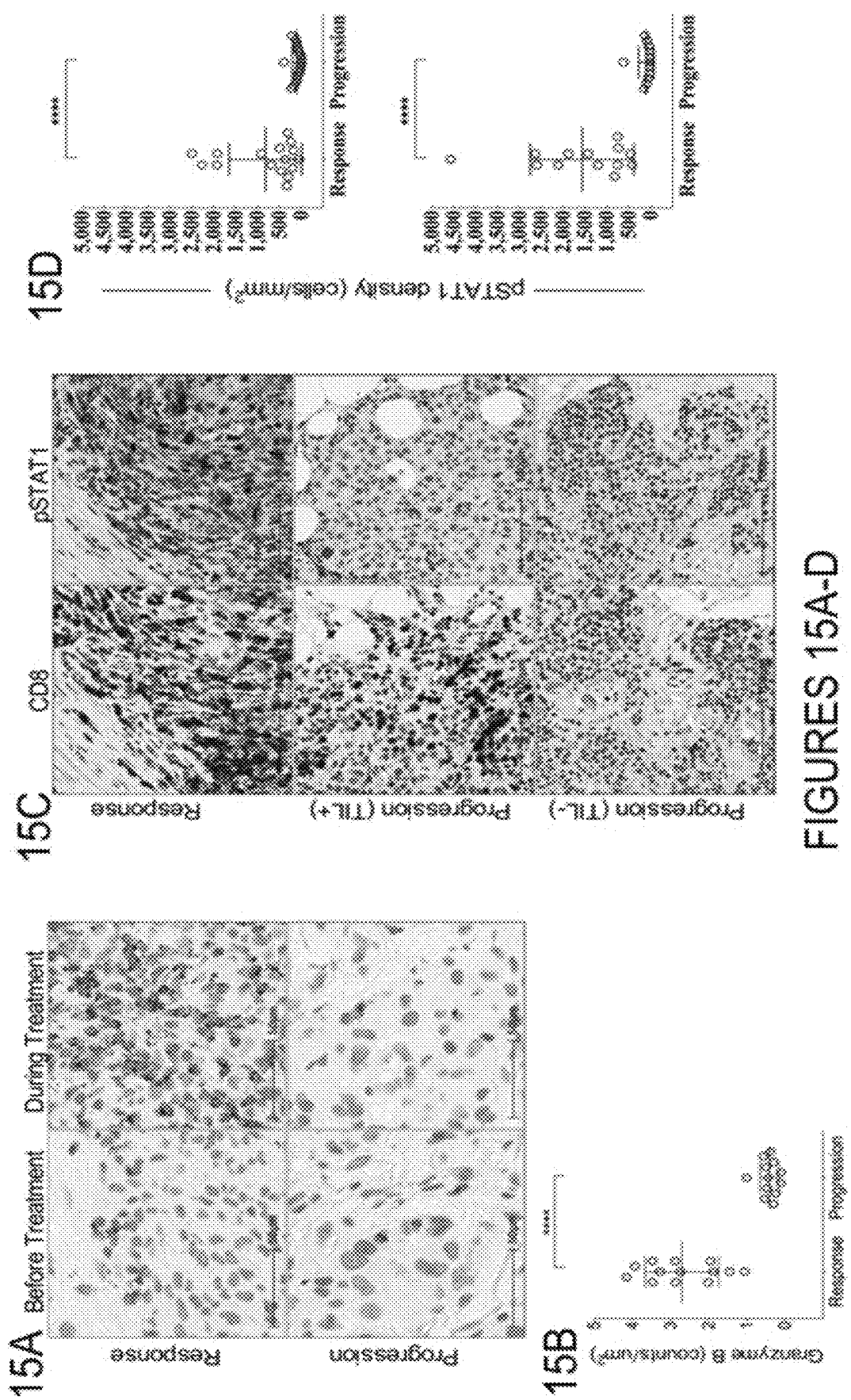
FIGURES 15A-D

METHODS FOR STRATIFYING NON-RESPONDERS TO THERAPIES THAT BLOCK PD1/PDL1 AXIS

This application claims the benefit of U.S. provisional patent applications 62/075,503, filed Nov. 5, 2014, and 62/084,484, filed Nov. 25, 2014, the entire contents of each of which are incorporated herein by reference.

STATEMENT REGARDING FEDERALLY SPONSORED RESEARCH

This invention was made with Government support under Grant No. AI091663, awarded by the National Institutes of Health. The Government has certain rights in the invention.

TECHNICAL FIELD OF THE INVENTION

The present invention relates generally to detection, monitoring and treatment of cancer and adaptive immune resistance. The invention relates to analyzing a tumor sample that can be applied in diagnosis, monitoring, clinical practice, clinical trial design, drug discovery, drug development, and so on. The invention also relates to materials and methods for the prediction and identification of patients likely to respond to treatments that block the PD-1/PD-L1 pathway, as well as to stratify patients that do not respond to such treatments, and methods of treating patients based on their responder/non-responder profile.

BACKGROUND

Pembrolizumab is an immunotherapeutic agent that blocks activity of the programmed death 1 (PD-1) molecule, a cell-surface receptor found on activated T cells. This receptor falls under the "immune-checkpoint" family of receptors present in/on immune cells and serves to control the immune response to a perturbation by controlling the magnitude and duration of T-cell activity. The activation of the PD-1 molecule occurs when another molecule, the programmed death 1 ligand (PD-L1) that is present on other cells (paracrine regulation) or on the same T-cell (autocrine regulation) binds to PD-1. PD-L1 is upregulated when T-cells secrete cytokines and other molecules into the external environment. The cells in the area then trigger translation of their PD-L1 transcript into protein to go to their cell surface. These cells then interact with the local activated T-cells and make T-cells inert. Hence, PD-L1 expression is a direct downstream reactive process to activated T-cells at the site of the tissue (Taube et al. *Sci Transl Med* 2012). This interaction helps to modulate the immune response of T cells to various conditions, including inflammation and infection. Cancer cells have been shown to recruit (or hijack) this mechanism to escape immune surveillance and killing. In recent early clinical trials in melanoma patients, several therapeutic antibodies that block PD-1 and/or PD-L1 (with the end result of interrupting the pathway hijacked by cancer cells) have shown an unprecedented percentage of patients experiencing objective clinical responses as defined by RECIST 1.1 criteria.

An important question that remains unknown is why some patients respond to anti-PD1 (or anti-PD-L1) and others do not. The first generation immune checkpoint blocking agent, anti-CTLA4, showed non-specific increases in T-cells in both responders and non-responders. This well-established phenomenon and the large amount of data supporting PD-L1 to be a direct downstream reactive process to activated T-cells has led experts in the field to focus their efforts on detecting expression of PD-L1. Since equivocal findings with respect to activated T-cells were previously well-established with immune checkpoint blockade, indirect measurement based on detecting PD-L1 has largely dictated progress.

Unfortunately, PD-L1 expression has shown to be a strategy limited by variable expression among strong responders and strong expression by non-melanoma normal cells of the parenchyma. Although 70% of patients do not respond, there are no known means to characterize non-responders. Hence, a significant clinical unmet need remains to develop improved and effective methods for identifying and treating patients based on their responsiveness to anti-PD1/PD-L1 therapy. The present invention directly addresses this need and others, as described below.

SUMMARY

The invention provides a method for microanatomic quantitative mapping of CD8+ T-cell organization within the tumor microenvironment of metastatic lesions to predict response to a targeted immunotherapy. The predictive value of PD-L1 expression is directly dependent on the CD8+ T cell organization in the tumor microenvironment with specific T cell receptors (TCRs) for recognizing tumor antigens (demonstrated by increased TCR Vb clonality). The invention provides a method that identifies characteristics of T cells in the tumor microenvironment that have been independent of any prior therapies and discovered to be directly relevant to T cell activity and the ability to predict response to anti-PD-1 therapy.

The present disclosure describes a method of analyzing a tumor sample that can be applied in diagnosis, monitoring, clinical practice, clinical trial design, drug discovery, drug development, and so on. Some embodiments of the disclosure relate to a method of analyzing a biological sample from a subject that has a tumor or cancer, comprising:

(1) determining, for target cells having a phenotype of interest:
   (a) location of the target cells in the tumor microenvironment of the sample (spatial resolution of the target cells);
   (b) density of the spatially resolved target cells in the sample; and
   (c) proximity between spatially resolved target cells of interest in the sample; and
(2) determining an overall score based at least in part on parameters (a) to (c).

In certain embodiments, the biological sample is obtained from the subject prior to treatment or during treatment. The phrase "obtained from the subject prior to treatment" may mean, e.g., obtained from a subject that has been previously treated with an antitumor agent and prior to treatment with a different antitumor agent, or obtained from a treatment-naive subject. In some embodiments, the method further comprises determining a score (density score) for the density of the spatially resolved target cells in the sample and/or a score (proximity score) for the proximity between spatially resolved target cells of interest in the sample, and wherein the density score is determined based at least in part on weighting of the density of particular types of spatially resolved target cells in the sample; the proximity score is determined based at least in part on weighting of the proximity between particular types of spatially resolved target cells of interest in the sample; and the overall score is determined based at least in part on weighting of the density score and/or the proximity score.

The invention provides a method of identifying a patient as a responder to single agent anti-PD-1 or anti-PD-L1 therapy. In one embodiment, the method comprises contacting a tissue sample from the patient with an assay reagent that detects CD8+ T cells. The method further comprises assaying for the presence of CD8+ T cells in the patient tissue sample, and comparing the amount of CD8+ T cells present in the patient tissue sample with a control sample of cancer biopsy tissue. An increased number of CD8+ T cells in the patient sample relative to the control (e.g., from known non-responder samples) is indicative of a responder to anti-PD-1 therapy.

Optionally, the method can comprise contacting the tissue sample with an assay reagent that detects CD8 expression and contacting the tissue sample (typically an adjacent section of the same tissue sample) with an assay reagent that detects S100 expression. The method further comprises assaying for presence of CD8 and S100 (or other tumor marker) in adjacent (or nearly adjacent) tissue sections from the patient sample. The use of a tumor marker such as S100 permits delineation of intratumoral and peritumoral regions within the tissue sample. The method optionally further comprises microanatomic alignment of tissue samples, such as by using newly developed algorithms to define subregions in the tumor microenvironment. The alignment of samples (or other method of comparing the assayed samples) permits analysis of the number of CD8+ T cells in the tumor.

In one embodiment, the assay reagents comprise antibodies that specifically detect CD8+ cells. The assaying typically comprises performing an immunoassay. The immunoassay is typically immunohistochemistry, but can be, for example, ELISA, radioimmunoassay, or other immunoassay known to those skilled in the art. The increase in CD8+ T cells can comprise an increased density of CD8+ cells in the patient sample relative to control. In some embodiments, the assaying comprises analysis of CD8+ T cell tumor infiltration, analysis of intratumoral, peritumoral, and/or perivascular CD8+ T cell location, CD8+ T cell density, and/or CD8+ T cell phenotype. In a particular embodiment, the assaying comprises comparing CD8+ T cell density in intratumoral and/or peritumoral areas in the patient tissue sample with a control (non-responder tumor) sample. A greater density of intratumoral and/or peritumoral CD8+ T cells relative to control is indicative of a responder to anti-PD-1 therapy.

The invention provides a method for identifying a patient as a responder to single agent anti-PD-1 or anti-PD-L1 therapy. In one embodiment, the method comprises contacting a sample from the patient with an assay reagent that detects myeloid-derived cells (MDCs). The method further comprises assaying for the presence of PDL1+ and PDL2+ MDCs in the patient tissue sample, and optionally comparing the amount of MDCs present in the patient sample with a control sample of cancer biopsy tissue. An increased number of MDCs in the patient sample relative to the control (e.g., from known non-responder samples) is indicative of a responder to anti-PD-1 therapy. Similar methods are provided for detecting adaptive immune resistance, the presence of cancer in a patient sample, determining efficacy of cancer therapy, and determining response to and monitoring the efficacy of cancer therapy.

The invention further provides a method of detecting adaptive immune resistance in a tumor sample. In one embodiment, the method comprises contacting the tumor sample with an assay reagent that detects PD-L1+ or PD-L2+ myeloid-derived cells (MDCs); and assaying for the presence of PD-L1+ or PD-L2+ MDCs in the tumor sample. The presence of PD-L1+ or PD-L2+ MDCs is indicative of adaptive immune resistance in the tumor sample. The presence of PD-L1+ or PD-L2+ MDCs in the tumor sample, for example in the invasive tumor margin, is indicative of adaptive immune resistance, and of likelihood of responding to anti-PD1 or anti-PDL1 therapy.

The invention additionally provides a method of overcoming adaptive immune resistance in a subject having a tumor. In one embodiment, the method comprises contacting a sample comprising the tumor with an assay reagent that detects PD-L1+ or PD-L2+ myeloid-derived cells (MDCs); and assaying for the presence of PD-L1+ or PD-L2+ MDCs in the tumor sample. The method further comprises administering to the subject an anti-PD-1 or anti-PD-L1 therapeutic agent if PD-L1+ or PD-L2+ MDCs are detected in the tumor sample. In the preceding methods, the assaying optionally further comprises assaying for the presence of CD8+, PD1+ and/or CD68+ cells in the tumor sample.

The invention also provides a method of identifying a patient as a responder to anti-PD-1 or anti-PD-L1 therapy. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of a responder to anti-PD-1 or PD-L1 blocking therapy. Also provided is a method of detecting cancer in a subject. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of cancer.

The invention further provides a method of determining efficacy of anti-PD-1 or anti-PD-L1 therapy in a patient. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of a responder to anti-PD-1 or PD-L1 blocking therapy. In one embodiment, the assaying is repeated after administration of anti-PD-1 or anti-PD-L1 therapy to the patient, and an increase in the presence of PD-L1+ or PD-L2+ MDCs in the patient sample relative to the previously assayed sample is indicative of effective anti-PD-1 or anti-PD-L1 therapy.

In the methods described herein, the sample can be a cell-containing sample, or a fluid-containing sample. The sample may comprise extracellular, cell dissociated, and/or cell-derived products. The tumor sample can be, for example, a tumor biopsy. Typically, the tumor sample comprises an invasive tumor margin. In one embodiment, the tumor sample is obtained from a metastatic lesion. In one embodiment, the sample comprises peripheral blood. In one embodiment, the patient is suspected of having a metastatic cancer. The methods described above can optionally further comprise treating the patient with anti-PD-1 therapy if identified as a responder, and with combination therapy if not identified as a responder.

Examples of PD-L1+ MDCs include, but are not limited to, MDCs having a phenotype selected from the group consisting of: PD-L1+CD11b+; PD-L1+CD11c+; PD-L1+CD14+; PD-L1+CD33+; PD-L1+CD38+; PD-L1+CD34+;

PD-L1+CD36/SR-b3+; PD-L1+CD59+; PD-L1+CD68+; PD-L1+CD163+; PD-L1+CD164+; PD-L1+HAM-56+; PD-L1+CD66a+; PD-L1+CD66b+; PD-L1+CD66c+; PD-L1+CD66d+; PD-L1+CD68/SR-D1+; PD-L1+CD42b/ GPIb alpha+; PD-L1+CDCXCR3+; and PD-L1+F4/80/ EMR1+. Examples of PD-L2+ MDCs include, but are not limited to, MDCs having a phenotype selected from the group consisting of: PD-L2$^+$CD11b$^+$; PD-L2$^+$CD11c$^+$; PD-L2$^+$CD24$^+$; PD-L2$^+$CD33$^+$; PD-L2$^+$CD38$^+$; PD-L2$^+$ CD34$^+$; PD-L2$^+$CD36/SR-b3$^+$; PD-L2$^+$CD59$^+$; PD-L2$^+$ CD68$^+$; PD-L2$^+$CD163$^+$; PD-L2$^+$CD164$^+$; PD-L2$^+$HAM-56$^+$; PD-L2$^+$CD66a$^+$; PD-L2$^+$CD66b$^+$; PD-L2$^+$CD66c$^+$; PD-L2$^+$CD66d$^+$; PD-L2$^+$CD68/SR-D2$^+$; PD-L2$^+$CD42b/ GPIb alpha$^+$; PD-L2$^+$CDCXCR3$^+$; and PD-L2$^+$F4/80/ EMR2$^+$.

In a typical embodiment of a method of the invention, the assay reagent comprises an antibody. Examples of antibodies include, but are not limited to, antibodies that specifically bind PD-L1+ and/or PD-L2+, as well as antibodies that bind markers of MDCs. In one embodiment, the assay reagent comprises an antibody that specifically binds PD-L1+ and an antibody that specifically binds CD11b+; CD11c+; CD14+; CD33+; CD38+; CD34+; CD36/SR-b3+; CD59+; CD68+; CD163+; CD164+; HAM-56+; CD66a+; CD66b+; CD66c+; CD66d+; CD68/SR-D1+; CD42b/GPIb alpha+; CDCXCR3+; or F4/80/EMR1+. In one embodiment, the assay reagent comprises an antibody that specifically binds PD-L2+ and an antibody that specifically binds CD11b$^+$; CD11c$^+$; CD24$^+$; CD33$^+$; CD38$^+$; CD34$^+$; CD36/SR-b3$^+$; CD59$^+$; CD68$^+$; CD163$^+$; CD164$^+$; HAM-56$^+$; CD66a$^+$; CD66b$^+$; CD66c$^+$; CD66d$^+$; CD68/SR-D2$^+$; CD42b/GPIb alpha$^+$; CDCXCR3$^+$; or F4/80/EMR2$^+$.

Representative assays include, but are not limited to, immunoassay, polymerase chain reaction, sequencing, including next generation sequencing, and analysis of MDC phenotype. Examples of an immunoassay include immunohistochemistry and immunofluorescence, including quantitative immunohistochemistry and quantitative immunofluorescence. These assays can be performed in single and multiplex formats.

Also provided is a method of analyzing a tumor sample that can be applied in diagnosis, monitoring, clinical practice, clinical trial design, drug discovery, drug development, and so on. Some embodiments of the disclosure relate to a method of analyzing a biological sample from a subject that has a tumor or cancer. In one embodiment, the method comprises: (1) determining, for target cells having a phenotype of interest: (a) location of the target cells in the tumor microenvironment of the sample (spatial resolution of the target cells); (b) density of the spatially resolved target cells in the sample; and (c) proximity between spatially resolved target cells of interest in the sample; and (2) determining an overall score based at least in part on parameters (a) to (c). In some embodiments, the method further comprises determining a score (density score) for the density of the spatially resolved target cells in the sample and/or a score (proximity score) for the proximity between spatially resolved target cells of interest in the sample. Typically, the density score is determined based at least in part on weighting of the density of particular types of spatially resolved target cells in the sample; the proximity score is determined based at least in part on weighting of the proximity between particular types of spatially resolved target cells of interest in the sample; and the overall score is determined based at least in part on weighting of the density score and/or the proximity score. In additional embodiments, the density score (e.g., weighting to determine the density score), the proximity score (e.g., weighting to determine the proximity score), or the overall score (e.g., weighting to determine the overall score), or any combination or all thereof, is adjusted based on therapeutic outcome of treatment of other subjects with a particular type of tumor or cancer (optionally considering also disease severity) using a particular single agent that blocks the PD-1/PD-L1/PD-L2 pathway, or using a particular anti-PD-1/PD-L1/PD-L2 agent and a particular additional antitumor agent (combination therapy).

The invention also provides a method of treating cancer in a patient. In one embodiment, the method comprises Identifying the patient as a responder to anti-PD-1 or anti-PD-L1 therapy in accordance with the methods described herein; and treating the patient with anti-PD-1 therapy if identified as a responder, and with combination therapy, or other alternative therapy, if not identified as a responder.

In one embodiment, the invention provides a method for stratifying non-responders to anti-PD-1 or anti-PD-L1 therapy. The method comprises microanatomic quantitative cellular mapping of CD8+, PD-1, PD-L1, and CD68 cellular organization within the invasive margin of the tumor microenvironment of metastatic lesions. This allows one to predict which sub-type of non-responder is presented, and to plan an effective treatment strategy. The lack of any one of the components: CD8, PD1 cells interfacing with CD68 PDL1 cells at the invasive margin, is indicative of a non-responder.

As described herein, non-responders can be reliably stratified into sub-types. Therapeutics can then be tailored to the specific sub-type of non-responder, for example, to convert their tumors to anti-PD1 responsive tumors. Listed below are examples of relevant profiles that can be observed at the invasive tumor margin:

The location, density and phenotype of CD68+ macrophages that express or do not express PDL1;

The location, density, and phenotype of CD8+ T-cells that express or do not express PD1;

One class of non-responders are CD8low-PD1low-CD68low-PDL1low at the invasive tumor margin;

Another class of non-responders are CD8high-PD1 high-CD68low-PDL1low at the invasive tumor margin;

Another class of non-responders are CD8low-PD1low-CD68low-PDL1 high at the invasive margin; and Another class of non-responders CD8low-PD1low-CD68high-PDL1 high at the invasive margin.

The drugs or therapies for treatment of non-responders can be selected based on their ability to modulate tumors to achieve a cellular signature at the invasive tumor margin that is needed to achieve a response to anti-PD1 therapy.

The invention further comprises a kit that can be used in practicing the methods described herein. The kit can comprise one or more antibodies, an oligonucleotide probe or a pair of oligonucleotide probes, or other assay reagents selected from those described herein. The reagents can optionally be labelled with a detectable marker. The kit can further comprise one or more containers for housing the, antibodies, primers, probe(s) and other reagents for use with the method.

BRIEF DESCRIPTION OF THE FIGURES

FIG. 4A shows CD8+ T cell density in cells/mm2 over time (baseline, 20-60 days, 8-120 days, >120 days) for responders (left panel), delayed responders (center panel) and progressors (right panel). FIG. 4B shows CD8+ T cell density at baseline for these same three response profiles in the peritumoral (left panel) and intratumoral (right panel) microenvironments.

FIGS. 8A-8F are digital photomicrographs of IHC analysis of PD1 (FIGS. 8A, 8D), PDL1 (FIGS. 8C, 8F), and CD68 (FIGS. 8B, 8E) from two patients, one with a regressing tumor (FIGS. 8A-8C) and one with a progressing tumor (FIGS. 8D-8F). 2 µm serially sectioned cuts show loss of PDL1 expression with anti-PD1 therapy.

FIGS. 9A and 9B, are digital photomicrographs showing examples of CD8 expression in melanoma tumours serially biopsied before PD-1 blocking treatment (Tx; left column of images) and 20-60 days after treatment began (Days$^+$20-60; right column of images) from a patient in the Response (FIG. 9A) and Progression (FIG. 9B) groups. Thick line separates tumour parenchyma (below line) and invasive margin (above line). Magnification, ×20. FIGS. 9C and 9D plot CD8$^+$ cell density at the tumour center (left panel) and invasive margin (right panel) in samples from all Responders (FIG. 9C, n=13) and Progressors (FIG. 9D, n=12) who received a biopsy before and during treatment. •=complete response, ○=partial response, Δ=delayed response.

FIGS. 10A-10B are digital photomicrographs showing that regressing tumours during treatment are associated with proliferating CD8$^+$ T cells that localize to the tumour. FIG. 10A, Representative example of CD8/Ki67 chromogenic double staining from a sample obtained during tumour regression shows double positive CD8 cells localized to the tumour parenchyma. The thick line separates the invasive margin (above line) and tumour (below line). FIG. 10B, Top: Representative single positive quiescent CD8+ cells (no Ki-67 labeling in nucleus) from the invasive margin. Bottom: Representative double positive cells (labeled Ki67 nucleus, CD8 labeled membrane) with characteristic chromatin patterns associated with subphases of mitosis. Magnification, ×40.

FIG. 11 is a set of plots showing baseline density and location of CD8$^+$ and CD4+ cells, according to treatment outcome. Melanoma samples collected before treatment with PD-1 blocking therapy were assessed for CD8 (Response n=22, Progression n=24) and CD4 (Response n=19, Progression n=18) density by quantitative immunohistochemistry in the tumour compartment and at the invasive margin. P<0.01, *P<0.001, ****P<0.0001.

FIGS. 15A-15D show immunohistochemical analysis of Granzyme B and pSTAT1 expression before and during treatment in terms of clinical response. FIG. 15A, Representative examples of granzyme B expression according to clinical response. FIG. 15B, Samples collected during PD-1 blocking therapy were evaluated for Granzyme B signal (Response n=13, Progression n=12) using quantitative immunohistochemistry. ****P<0.0001. FIG. 15C, Localization of CD8 and pSTAT1 cells in samples obtained before treatment from a responder, and two progressors (+/−a CD8 presence). The progressor with a moderate presence of CD8 cells did not show pSTAT1 expression in the area. FIG. 15D, Using quantitative IHC analysis, the Response group was associated with significantly higher expression of pSTAT1$^+$ at the invasive margin before and during treatment (Response n=16, Progression n=18, p=0.002 for pre-treatment biopsies and Response n=13, Progression n=12, p<0.0001 for post treatment biopsies).

DETAILED DESCRIPTION

Figure 1:
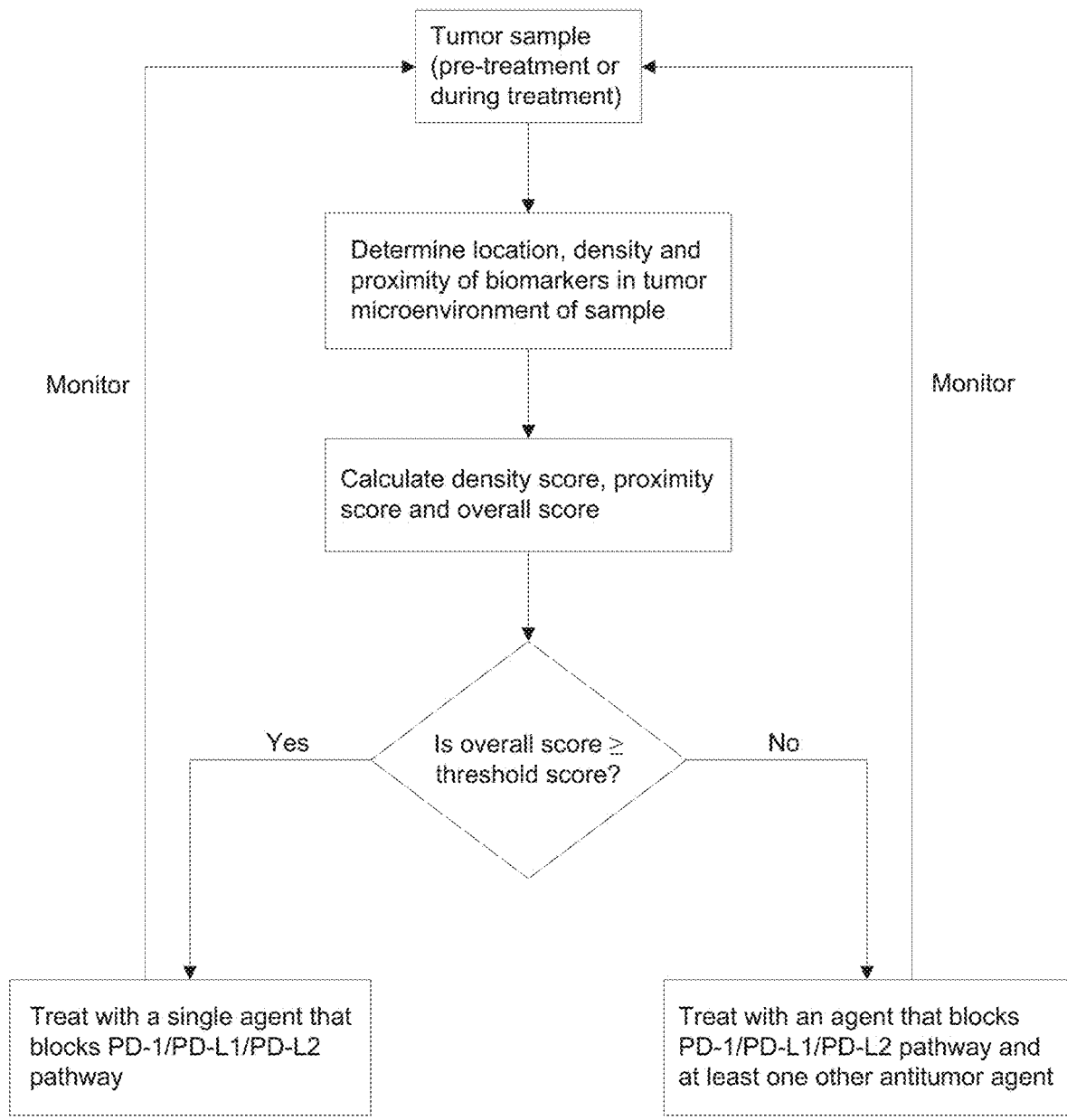
FIG. 1 is a flowchart of an embodiment of the method of analyzing a tumor sample described herein.

The present invention is based on the discovery that expression of PD1 and PD-L1 on immune cells infiltrating the tumor and their location in the tumor microenvironment is a key predictor of response to therapy. The data described herein show, using samples from patients with melanoma that were treated with anti-PD-1 therapy, that a certain set of conditions enables PD-1 blockade to mediate tumor regression. These are the presence of $CD8^+$ T cells and immune cells, including macrophages, that express PD-1 and PD-L1 at the tumor margin, together with a T-cell population with less-diverse antigen specificity. Tumors that have already been recognized by the immune system, and contain infiltrating immune cells bearing PD-1 and PD-L1, are particularly sensitive to immune-checkpoint blockade.

Definitions

All scientific and technical terms used in this application have meanings commonly used in the art unless otherwise specified. As used in this application, the following words or phrases have the meanings specified.

As used herein, "control biopsy tissue" or "control sample" refers to a sample of cancer tissue that is representative of typical cancer tissue that is non-metastatic or not responsive to anti-PD1 therapy.

As used herein, the term "tumor cells" includes cancer cells, the term "primary tumor" includes primary cancer, the term "secondary (metastatic) tumor" includes secondary (metastatic) cancer, the term "solid tumor" includes solid cancer, the term "tumor sample" includes cancer sample, the term "tumor microenvironment" includes cancer microenvironment, the term "invasive tumor margin" includes invasive cancer margin, the term "tumor parenchyma" includes cancer parenchyma, and the term "antitumor agent" includes anticancer agent.

As used herein, an "oligonucleotide probe" is an oligonucleotide having a nucleotide sequence sufficiently complementary to its target nucleic acid sequence to be able to form a detectable hybrid probe:target duplex under high stringency hybridization conditions. An oligonucleotide probe is an isolated chemical species and may include additional nucleotides outside of the targeted region as long as such nucleotides do not prevent hybridization under high stringency hybridization conditions. Non-complementary sequences, such as promoter sequences, restriction endonuclease recognition sites, or sequences that confer a desired secondary or tertiary structure such as a catalytic active site can be used to facilitate detection using the invented probes. An oligonucleotide probe optionally may be labeled with a detectable marker such as a radioisotope, a fluorescent moiety, a chemiluminescent moiety, an enzyme or a ligand, which can be used to detect or confirm probe hybridization to its target sequence. "Probe specificity" refers to the ability of a probe to distinguish between target and non-target sequences.

The term "nucleic acid", "oligonucleotide" or "polynucleotide" refers to a deoxyribo-nucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, a "detectable marker" or "label" is a molecule attached to, or synthesized as part of a reagent. This molecule should be uniquely detectable and will allow the reagent to be detected as a result. These detectable moieties are often radioisotopes, chemiluminescent molecules, enzymes, haptens, or even unique oligonucleotide sequences.

As used herein, a "hybrid" or a "duplex" is a complex formed between two single-stranded nucleic acid sequences by Watson-Crick base pairings or non-canonical base pairings between the complementary bases.

As used herein, "hybridization" is the process by which two complementary strands of nucleic acid combine to form a double-stranded structure ("hybrid" or "duplex"). "Stringency" is used to describe the temperature and solvent composition existing during hybridization and the subsequent processing steps. Under high stringency conditions only highly complementary nucleic acid hybrids will form; hybrids without a sufficient degree of complementarity will not form. Accordingly, the stringency of the assay conditions determines the amount of complementarity needed between two nucleic acid strands forming a hybrid. Stringency conditions are chosen to maximize the difference in stability between the hybrid formed with the target and the non-target nucleic acid. Exemplary stringency conditions are described herein below.

As used herein, "complementarity" is a property conferred by the base sequence of a single strand of DNA or RNA which may form a hybrid or double-stranded DNA: DNA, RNA:RNA or DNA:RNA through hydrogen bonding between Watson-Crick base pairs on the respective strands. Adenine (A) ordinarily complements thymine (T) or Uracil (U), while guanine (G) ordinarily complements cytosine (C). "Fully complementary", when describing a probe with respect to its target sequence, means that complementarity is present along the full length of the probe.

As used herein, "adjacent", in the context of nucleotide sequences and oligonucleotides, means immediately next to one another (end to end), such that two adjacent molecules do not overlap with one another and there is no gap between them. For example, two oligonucleotide probes hybridized to adjacent regions of a target nucleic acid molecule have no nucleotides of the target sequence (unpaired with either of the two probes) between them.

By "sufficiently complementary" or "substantially complementary" is meant nucleic acids having a sufficient amount of contiguous complementary nucleotides to form, under high stringency hybridization conditions, a hybrid that is stable for detection.

By "preferentially hybridize" is meant that, under high stringency hybridization conditions, oligonucleotide probes can hybridize with their target nucleic acids to form stable probe:target hybrids (thereby indicating the presence of the target nucleic acids) without forming stable probe:non-target hybrids (that would indicate the presence of non-target nucleic acids from other organisms). Thus, the probe hybridizes to target nucleic acid to a sufficiently greater extent than to non-target nucleic acid to enable one skilled in the art to accurately detect the presence of the relevant bacteria and distinguish their presence from that of other organisms.

Preferential hybridization can be measured using techniques known in the art and described herein.

As used herein, "room temperature" means about 20-25° C.

As used herein, "a" or "an" means at least one, unless clearly indicated otherwise.

"Expression" includes intracellular mRNA expression; intracellular protein expression; extracellular cell surface-anchored protein expression; extracellular, cell-dissociated, but cell-derived mRNA; extracellular, cell-dissociated, but cell-derived protein. Expression can include a complete mRNA sequence, a complete protein, or portions of the sequence or protein that remain identifiable.

"Myeloid-derived cells (MDCs)" means cells expressing one or more of the following: $CD11b^+$; $CD11c^+$; $CD14^+$; $CD33^+$; $CD38^+$; $CD34^+$; $CD36/SR-b3^+$; $CD59^+$; $CD68^+$; $CD163^+$; $CD164^+$; $HAM-56^+$; $CD66a^+$; $CD66b^+$; $CD66c^+$; $CD66d^+$; $CD68/SR-D1^+$; $CD42b/GPIb\ alpha^+$; $CDCXCR3^+$; $F4/80/EMR1^+$, and other myeloid-specific markers.

"PD-L1 expressing myeloid-derived cells (PD-L1+ MDCs)" means intact cells exhibiting intracellular mRNA expression, intracellular protein expression comprising co-expression of the following groups: $PD-L1^+CD11\ b^+$; $PD-L1^+CD11c^+$; $PD-L1^+CD14^+$; $PD-L1^+CD33^+$; $PD-L1^+CD38^+$; $PD-L1^+CD34^+$; $PD-L1^+CD36/SR-b3^+$; $PD-L1^+CD59^+$; $PD-L1^+CD68^+$; $PD-L1^+CD163^+$; $PD-L1^+CD164^+$; $PD-L1^+HAM-56^+$; $PD-L1^+CD66a^+$; $PD-L1^+CD66b^+$; $PD-L1^+CD66c^+$; $PD-L1^+CD66d^+$; $PD-L1^+CD68/SR-D1^+$; $PD-L1^+CD42b/GPIb\ alpha^+$; $PD-L1^+CDCXCR3^+$; $PD-L1^+F4/80/EMR1^+$.

"PD-L2 expressing myeloid-derived cells (PD-L2+ MDCs)" means intact cells exhibiting intracellular mRNA expression or intracellular protein expression comprising co-expression of the following groups: $PD-L2^+CD11b^+$; $PD-L2^+CD11c^+$; $PD-L2^+CD24^+$; $PD-L2^+CD33^+$; $PD-L2^+CD38^+$; $PD-L2^+CD34^+$; $PD-L2^+CD36/SR-b3^+$; $PD-L2^+CD59^+$; $PD-L2^+CD68^+$; $PD-L2^+CD163^+$; $PD-L2^+CD164^+$; $PD-L2^+HAM-56^+$; $PD-L2^+CD66a^+$; $PD-L2^+CD66b^+$; $PD-L2^+CD66c^+$; $PD-L2^+CD66d^+$; $PD-L2^+CD68/SR-D2^+$; $PD-L2^+CD42b/GPIb\ alpha^+$; $PD-L2^+CDCXCR3^+$; $PD-L2^+F4/80/EMR2^+$.

As used herein, "cell-containing sample" refers to cells obtained from a human or animal from the peripheral blood, peripheral venous blood, peripheral arterial blood, peripheral whole blood monocytes, peripheral mononuclear cell enriched monocytes, red blood cell lysate of whole peripheral blood, serum, plasma, tears, hair, sputum, bronchoalveoli, cerebrospinal fluid, pericardial fluid, pleural fluid, peritoneal fluid, synovial fluid, vaginal fluid, urethral fluid, pericarditis fluid, pleural effusion fluid, ascites fluid, saliva, sweat, tumor, lymph, lymphatic vessels, lymph node tissue, adenoid tissue, spleen, spleen cells, or cancer tissue.

As used herein, "cell-derived extracellular products" means products derived from cells that are dissociated from cells and extracellular in form and comprise of nucleic acids, proteins, lipids, carbohydrates, nanovesicles, microvesicles, glycated end-products, enzymes, chemical products of metabolism, chemical by-products of metabolism, cations, and anions.

As used herein, "myeloid cell-derived cell products" is intended to mean cell-derived products that are dissociated from cells and extracellular where products comprising nucleic acids, proteins, lipids, carbohydrates, nanovesicles, microvesicles, glycated end-products, enzymes, chemical products of metabolism, chemical by-products of metabolism, cations, and anions can uniquely identify myeloid-cells.

"A sample comprising extracellular, cell-dissociated, cell-derived products that are independently or dependently cell-dissociated" refers to sample comprising the co-presence in the same sample of one of the following: $PD-L1^+$ and $CD11b^+$; $PD-L1^+$ and $CD11c^+$; $PD-L1^+$ and $CD14^+$; $PD-L1^+$ and $CD33^+$; $PD-L1^+$ and $CD38^+$; $PD-L1^+$ and $CD34^+$; $PD-L1^+$ and $CD36/SR-b3^+$; $PD-L1^+$ and $CD59^+$; $PD-L1^+$ and $CD68^+$; $PD-L1^+$ and $CD163^+$; $PD-L1^+$ and $CD164^+$; $PD-L1^+$ and $HAM-56^+$; $PD-L1^+$ and $CD66a^+$; $PD-L1^+$ and $CD66b^+$; $PD-L1^+$ and $CD66c^+$; $PD-L1^+$ and $CD66d^+$; $PD-L1^+$ and $CD68/SR-D1^+$; $PD-L1^+$ and $CD42b/GPIb\ alpha^+$; $PD-L1^+$ and $CDCXCR3^+$; $PD-L1^+$ and $F4/80/EMR1^+$ or $PD-L2^+$ and $CD11b^+$; $PD-L2^+$ and $CD11c^+$; $PD-L2^+$ and $CD14^+$; $PD-L2^+$ and $CD33^+$; $PD-L2^+$ and $CD38^+$; $PD-L2^+$ and $CD34^+$; $PD-L2^+$ and $CD36/SR-b3^+$; $PD-L2^+$ and $CD59^+$; $PD-L2^+$ and $CD68^+$; $PD-L2^+$ and $CD163^+$; $PD-L2^+$ and $CD164^+$; $PD-L2^+$ and $HAM-56^+$; $PD-L2^+$ and $CD66a^+$; $PD-L2^+$ and $CD66b^+$; $PD-L2^+$ and $CD66c^+$; $PD-L2^+$ and $CD66d^+$; $PD-L2^+$ and $CD68/SR-D1^+$; $PD-L2^+$ and $CD42b/GPIb\ alpha^+$; $PD-L2^+$ and $CDCXCR3^+$; $PD-L2^+$ and $F4/80/EMR1^+$.

As used herein, "anti-PD-1" or "anti-PD-L1 therapy" means a therapeutic strategy that targets the programmed death 1 (PD-1) molecule or its ligands, PD-L1 and PD-L2, such as by disrupting established, present interactions between PD-1 and PD-L1 or PD-L2, or blocking future interactions between PD-1 and PD-L1 or between PD-1 and PD-L2, blocking activation of PD-1 independently of whether it is interacting with PD-L1 or PD-L2, or blocking PD-L1 or PD-L2 signaling pathways that are triggered upon PD-L1 or PD-L2 interacting with PD-1. These therapeutic strategies include, for example, immunotherapy directed against PD-1 or PD-L1 and include small molecules, peptides, monoclonal antibodies, polyclonal antibodies, interfering RNA oligonucleotides, and interfering DNA oligonucleotides. Examples of anti-PD-1 immunotherapeutic agents include, but are not limited to, pembrolizumab, nivolumab, and pidilizumab. Examples of anti-PD-L1 immunotherapeutic agents include, but are not limited to, BMS-936559 and atezolizumab.

As used herein, an "effective amount" is intended to mean an amount, dosage, administration schedule that is sufficient to obtain beneficial outcomes.

As used herein, "treating" or "treatment" of a disease in a patient refers to (1) preventing the symptoms or disease from occurring in a human or animal that is does not yet display symptoms of the disease; (2) inhibiting the disease or arresting its progression; or (3) ameliorating or causing regression of the disease or the symptoms associated with the disease.

As used herein, the term "nucleic acid" refers to a deoxyribo-nucleotide or ribonucleotide sequence in either single- or double-stranded form, and unless otherwise limited, encompasses known analogs of natural nucleotides that hybridize to nucleic acids in a manner similar to naturally-occurring nucleotides.

CD33 or Siglec-3 is a transmembrane receptor expressed on cells of myeloid lineage. CD33 is usually considered myeloid-specific, but it can also be found on some lymphoid cells. The following GenBank DNA accession numbers represent the CD33 protein sequence: NP 001763.3, NP 001171079.1, NP 001076087.1, P20138.2, CAD36509.1, AAH28152.1, AAK83654.1, EAW71996.1, EAW71995.1, and EAW71994.1. The sequences represented by each of these GenBank accession numbers is incorporated herein by reference for all purposes.

CD14 is a marker of monocytes in the body, another myeloid-derived population that circulates in peripheral blood. The following GenBank DNA accession numbers represent the CD14 protein sequence: CAG33297.1, AAA51930.1, P08571.2, NP 001167576.1, NP 001167575.1, NP_001035110.1, NP 000582.1, ADX31876.1, AAC83816.1, EAW62037.1, AAH10507.1, and BAG55282.1. The sequences represented by each of these GenBank accession numbers is incorporated herein by reference for all purposes.

CD66b is a marker of granulocytes in the body, another myeloid-derived population that circulates in peripheral blood. In cancer these myeloid populations may be induced to become suppressive MDSC. The following GenBank DNA accession numbers represent the CD66b protein sequence: AAH26263.1, P31997.2, NP 001806.2, AAC13659.1, and CAB08298.1. The sequences represented by each of these GenBank accession numbers is incorporated herein by reference for all purposes.

Methods

The invention provides a method for identifying a patient as a responder to single agent anti-PD-1 or anti-PD-L1 therapy. In one embodiment, the method comprises contacting a sample from the patient with an assay reagent that detects myeloid-derived cells (MDCs). The method further comprises assaying for the presence of PDL1+ and PDL2+ MDCs in the patient tissue sample, and optionally comparing the amount of MDCs present in the patient sample with a control sample of cancer biopsy tissue. An increased number of MDCs in the patient sample relative to the control (e.g., from known non-responder samples) is indicative of a responder to anti-PD-1 therapy. These method steps can be adapted for detecting the presence of cancer in a patient sample, determining efficacy of cancer therapy, and determining response to and monitoring the efficacy of cancer therapy.

The invention further provides a method of detecting adaptive immune resistance in a tumor sample. In one embodiment, the method comprises contacting the tumor sample with an assay reagent that detects PD-L1+ or PD-L2+ myeloid-derived cells (MDCs); and assaying for the presence of PD-L1+ or PD-L2+ MDCs in the tumor sample. The presence of PD-L1+ or PD-L2+ MDCs is indicative of adaptive immune resistance in the tumor sample. The presence of PD-L1+ or PD-L2+ MDCs in the tumor sample, for example in the invasive tumor margin, is indicative of adaptive immune resistance, and of likelihood of responding to anti-PD1 or anti-PDL1 therapy.

The invention additionally provides a method of overcoming adaptive immune resistance in a subject having a tumor. In one embodiment, the method comprises contacting a sample comprising the tumor with an assay reagent that detects PD-L1+ or PD-L2+ myeloid-derived cells (MDCs); and assaying for the presence of PD-L1+ or PD-L2+ MDCs in the tumor sample. The method further comprises administering to the subject an anti-PD-1 or anti-PD-L1 therapeutic agent if PD-L1+ or PD-L2+ MDCs are detected in the tumor sample. In the preceding methods, the assaying optionally further comprises assaying for the presence of CD8+, PD1+ and/or CD68+ cells in the tumor sample.

The invention also provides a method of identifying a patient as a responder to anti-PD-1 or anti-PD-L1 therapy. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of a responder to anti-PD-1 or PD-L1 blocking therapy. Also provided is a method of detecting cancer in a subject. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of cancer.

The invention further provides a method of determining efficacy of anti-PD-1 or anti-PD-L1 therapy in a patient. In one embodiment, the method comprises contacting a sample from the patient with an assay reagent that detects PD-L1+ or PD-L2+ myeloid-derived cells (MDCs); and assaying for the presence of PD-L1+ or PD-L2+ MDCs in the patient sample. The presence of PD-L1+ or PD-L2+ MDCs is indicative of a responder to anti-PD-1 or PD-L1 blocking therapy. In one embodiment, the assaying is repeated after administration of anti-PD-1 or anti-PD-L1 therapy to the patient, and an increase in the presence of PD-L1+ or PD-L2+ MDCs in the patient sample relative to the previously assayed sample is indicative of effective anti-PD-1 or anti-PD-L1 therapy.

In the methods described herein, the sample can be a cell-containing sample, or a fluid-containing sample. The sample may comprise extracellular, cell dissociated, and/or cell-derived products. The tumor sample can be, for example, a tumor biopsy. Typically, the tumor sample comprises an invasive tumor margin. In one embodiment, the tumor sample is obtained from a metastatic lesion. In one embodiment, the sample comprises peripheral blood. In one embodiment, the patient is suspected of having a metastatic cancer. The methods described above can optionally further comprise treating the patient with anti-PD-1 therapy if identified as a responder, and with combination therapy if not identified as a responder.

Examples of PD-L1+ MDCs include, but are not limited to, MDCs having a phenotype selected from the group consisting of: PD-L1+CD11b+; PD-L1+CD11c+; PD-L1+CD14+; PD-L1+CD33+; PD-L1+CD38+; PD-L1+CD34+; PD-L1+CD36/SR-b3+; PD-L1+CD59+; PD-L1+CD68+; PD-L1+CD163+; PD-L1+CD164+; PD-L1+HAM-56+; PD-L1+CD66a+; PD-L1+CD66b+; PD-L1+CD66c+; PD-L1+CD66d+; PD-L1+CD68/SR-D1+; PD-L1+CD42b/GPIb alpha+; PD-L1+CDCXCR3+; and PD-L1+F4/80/EMR1+. Examples of PD-L2+ MDCs include, but are not limited to, MDCs having a phenotype selected from the group consisting of: PD-L2$^+$CD11b$^+$; PD-L2$^+$CD11c$^+$; PD-L2$^+$CD24$^+$; PD-L2$^+$CD33$^+$; PD-L2$^+$CD38$^+$; PD-L2$^+$CD34$^+$; PD-L2$^+$CD36/SR-b3$^+$; PD-L2$^+$CD59$^+$; PD-L2$^+$CD68$^+$; PD-L2$^+$CD163$^+$; PD-L2$^+$CD164$^+$; PD-L2$^+$HAM-56$^+$; PD-L2$^+$CD66a$^+$; PD-L2$^+$CD66b$^+$; PD-L2$^+$CD66c$^+$; PD-L2$^+$CD66d$^+$; PD-L2$^+$CD68/SR-D2$^+$; PD-L2$^+$CD42b/GPIb alpha$^+$; PD-L2$^+$CDCXCR3$^+$; and PD-L2$^+$F4/80/EMR2$^+$.

In a typical embodiment of a method of the invention, the assay reagent comprises an antibody. Examples of antibodies include, but are not limited to, antibodies that specifically bind PD-L1+ and/or PD-L2+, as well as antibodies that bind markers of MDCs. In one embodiment, the assay reagent comprises an antibody that specifically binds PD-L1+ and an antibody that specifically binds CD11b+; CD11c+; CD14+; CD33+; CD38+; CD34+; CD36/SR-b3+; CD59+; CD68+; CD163+; CD164+; HAM-56+; CD66a+; CD66b+; CD66c+; CD66d+; CD68/SR-D1+; CD42b/GPIb alpha+;

CDCXCR3+; or F4/80/EMR1+. In one embodiment, the assay reagent comprises an antibody that specifically binds PD-L2+ and an antibody that specifically binds CD11b$^+$; CD11c$^+$; CD24$^+$; CD33$^+$; CD38$^+$; CD34$^+$; CD36/SR-b3$^+$; CD59$^+$; CD68$^+$; CD163$^+$; CD164$^+$; HAM-56$^+$; CD66a$^+$; CD66b$^+$; CD66c$^+$; CD66d$^+$; CD68/SR-D2$^+$; CD42b/GPIb alpha$^+$; CDCXCR3$^+$; or F4/80/EMR2$^+$.

Representative assays include, but are not limited to, immunoassay, polymerase chain reaction, sequencing, including next generation sequencing, and analysis of MDC phenotype. Examples of an immunoassay include immunohistochemistry and immunofluorescence, including quantitative immunohistochemistry and quantitative immunofluorescence. These assays can be performed in single and multiplex formats.

The invention also provides a method of treating cancer in a patient. In one embodiment, the method comprises Identifying the patient as a responder to anti-PD-1 or anti-PD-L1 therapy in accordance with the methods described herein; and treating the patient with anti-PD-1 therapy if identified as a responder, and with combination therapy if not identified as a responder.

In one embodiment, the invention provides a method for stratifying non-responders to anti-PD-1 or anti-PD-L1 therapy. The method comprises microanatomic quantitative cellular mapping of CD8+, PD-1, PD-L1, and CD68 cellular organization within the invasive margin of the tumor microenvironment of metastatic lesions. This allows one to predict which sub-type of non-responder is presented, and to plan an effective treatment strategy. The lack of any one of the components: CD8, PD1 cells interfacing with CD68 PDL1 cells at the invasive margin, is indicative of a non-responder.

As described herein, non-responders can be reliably stratified into sub-types. Therapeutics can then be tailored to the specific sub-type of non-responder, for example, to convert their tumors to anti-PD1 responsive tumors. Listed below are examples of relevant profiles that can be observed at the invasive tumor margin:

The location, density and phenotype of CD68+ macrophages that express or do not express PDL1;
The location, density, and phenotype of CD8+ T-cells that express or do not express PD1;
One class of non-responders are CD8low-PD1low-CD68low-PDL1low at the invasive tumor margin;
Another class of non-responders are CD8high-PD1high-CD68low-PDL1low at the invasive tumor margin;
Another class of non-responders are CD8low-PD1low-CD68low-PDL1high at the invasive margin; and
Another class of non-responders CD8low-PD1low-CD68high-PDL1 high at the invasive margin.

The drugs or therapies for treatment of non-responders can be selected based on their ability to modulate tumors to achieve a cellular signature at the invasive tumor margin that is needed to achieve a response to anti-PD1 therapy.

The sample is typically a tumor sample, such as a biopsy or surgical excision obtained from the patient. Typically, the tumor sample is obtained from a metastatic lesion. The patient can be one who is suspected of having a metastatic cancer. Examples of cancer include, but are not limited to, melanoma, lung cancer, including for example non-small cell lung cancer, breast cancer, head and neck cancer, urothelial cancer. Further examples of cancer include adrenocortical carcinoma, anal cancer, bladder cancer, blood cancer, brain tumor, brain stem glioma, brain tumor, cerebellar astrocytoma, brain tumor, cerebral astrocytoma, ependymoma, breast cancer, carcinoid tumor, carcinoma of unknown primary, cervical cancer, colon cancer, endometrial cancer, esophageal cancer, extrahepatic bile duct cancer, Ewings family of tumors (PNET), extracranial germ cell tumor, eye cancer, intraocular melanoma, gallbladder cancer, gastric cancer, germ cell tumor, extragonadal, gestational trophoblastic tumor, head and neck cancer, hypopharyngeal cancer, islet cell carcinoma, kidney cancer (renal cell cancer), laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell and small cell, lymphoma, cutaneous T-cell lymphoma, Hodgkin's disease, non-Hodgkin's disease, multiple myeloma and other plasma cell neoplasms, mycosis fungoides, myelodysplastic syndrome, myeloproliferative disorders, nasopharyngeal cancer, neuroblastoma, oral cancer, oropharyngeal cancer, osteosarcoma, ovarian epithelial cancer, ovarian germ cell tumor, pancreatic cancer, islet cell carcinoma, paranasal sinus and nasal cavity cancer, parathyroid cancer, penile cancer, pituitary cancer, plasma cell neoplasm, prostate cancer, rhabdomyosarcoma, rectal cancer, renal cell cancer, salivary gland cancer, sezary syndrome, skin cancer, kaposi's sarcoma, melanoma, small intestine cancer, soft tissue sarcoma, stomach cancer, testicular cancer, thymoma, malignant, thyroid cancer, urethral cancer, uterine cancer, sarcoma, vaginal cancer, vulvar cancer, and Wilms' tumor.

The method can optionally further comprise treating the patient with anti-PD-1 therapy if identified as a responder. Patients identified as non-responders (or "progressors" or not identified as responders) can be treated with combination therapy. Examples of combination therapy include those known in the art, and will be selected in the judgment of the treating physician. The therapy can be a combination of anti-PD-1 therapy with conventional cancer therapy, such as chemotherapeutic agents and/or other immunotherapeutic agents, such as anti-CTLA4, as well as radiation therapy, including local radiation therapy, and small molecule therapeutics. Some representative examples of chemotherapeutic agents include cisplatin, pemetrexed, carboplatin, paclitaxel, dacarbazine, temozolomide, and combinations thereof.

Also provided is a method of treating cancer in a patient. In one embodiment the method comprises identifying the patient as a responder to anti-PD-1 or anti-PD-L1 therapy in accordance with the methods described herein, and treating the patient with anti-PD-1 therapy if identified as a responder. Alternatively, the patient is treated with combination therapy if not identified as a responder.

Kits

The invention further comprises a kit that can be used in practicing the methods described herein. The kit can comprise one or more antibodies, an oligonucleotide probe or a pair of oligonucleotide probes, or other assay reagents selected from those described herein. The reagents can optionally be labelled with a detectable marker. The kit can further comprise one or more containers for housing the, antibodies, primers, probe(s) and other reagents for use with the method.

Method of Analyzing a Tumor Sample and Applications Thereof

The present disclosure describes a method of analyzing a tumor sample that can be applied in diagnosis, monitoring, clinical practice, clinical trial design, drug discovery, drug development, and so on. Some embodiments of the disclosure relate to a method of analyzing a biological sample from a subject that has a tumor or cancer, comprising:

(1) determining, for target cells having a phenotype of interest:
  (a) location of the target cells in the tumor microenvironment of the sample (spatial resolution of the target cells);
  (b) density of the spatially resolved target cells in the sample; and
  (c) proximity between spatially resolved target cells of interest in the sample; and
(2) determining an overall score based at least in part on parameters (a) to (c).

Location considerations include the invasive tumor margin, stroma (connective tissue), tumor parenchyma, perivascular regions (blood and lymphatic), as well as intravascular (blood and lymphatic). Proximity can be, for example, pixel based, intracellular based, intercellular based, and/or extracellular based. Multiparametric considerations include pixel based, cell based, location based, and whole slide based analysis. Density analysis can be, for example, pixel based, area based, cell based, and/or whole slide based. Density of positive pixels can, for example, be based on the number of positive pixels per square mm, number of positive pixels per total number of pixels per unit area, and number of positive pixels per total number of pixels. In one embodiment, the density of positive pixels is determined for one to 1,000 positive pixels. The density of positive cells can, for example, be based on the number of positive cells per square mm, or the number of positive cells per total number of nucleated cells. In one embodiment, the density of positive cells is determined for up to ten targets on one cell. Targets can include, for example, intracellular proteins or derivatives, including cytoplasmic (or soluble), intraorganelle, organelle membrane attached, or intraorganelle membrane targets. Also included are membrane proteins and/or derivatives, including peripheral and integral proteins, and extracellular proteins and/or derivatives, including membrane bound, secreted, excreted, vesicular, naked, blebbing, exosomal, lysosomal, pore derived, necrotic cell derived, and vascular derived proteins and their derivatives.

In certain embodiments, the biological sample is obtained from the subject prior to treatment or during treatment. The phrase "obtained from the subject prior to treatment" may mean, e.g., obtained from a subject that has been previously treated with an antitumor agent and prior to treatment with a different antitumor agent, or obtained from a treatment-naive subject.

In some embodiments, the method further comprises determining a score (density score) for the density of the spatially resolved target cells in the sample and/or a score (proximity score) for the proximity between spatially resolved target cells of interest in the sample, and wherein:
  the density score is determined based at least in part on weighting of the density of particular types of spatially resolved target cells in the sample;
  the proximity score is determined based at least in part on weighting of the proximity between particular types of spatially resolved target cells of interest in the sample; and
  the overall score is determined based at least in part on weighting of the density score and/or the proximity score.

The density score, the proximity score, or the overall score, or any combination or all thereof, can be adjusted based on any one or more appropriate factors. In certain embodiments, the density score (e.g., weighting to determine the density score), the proximity score (e.g., weighting to determine the proximity score), or the overall score (e.g., weighting to determine the overall score), or any combination or all thereof, is adjusted based on whether the sample is obtained from the subject prior to treatment or during treatment.

In further embodiments, the density score (e.g., weighting to determine the density score), the proximity score (e.g., weighting to determine the proximity score), or the overall score (e.g., weighting to determine the overall score), or any combination or all thereof, is adjusted based on the particular type of tumor or cancer (and optionally the disease severity [e.g., the stage of the disease]) the subject has.

In yet further embodiments, the density score (e.g., weighting to determine the density score), the proximity score (e.g., weighting to determine the proximity score), or the overall score (e.g., weighting to determine the overall score), or any combination or all thereof, is adjusted based on the location of the primary tumor and/or the location of any secondary (metastatic) tumor.

In still further embodiments, the density score (e.g., weighting to determine the density score), the proximity score (e.g., weighting to determine the proximity score), or the overall score (e.g., weighting to determine the overall score), or any combination or all thereof, is adjusted based on information relating to the subject, such as the ethnicity, the race, the gender, the age, the body mass index, the diet, risk factors (e.g., drinking, smoking, stress and/or inactivity), the (individual and/or family) medical history or the overall health, or any combination or all thereof, of the subject.

In additional embodiments, the density score (e.g., weighting to determine the density score), the proximity score (e.g., weighting to determine the proximity score), or the overall score (e.g., weighting to determine the overall score), or any combination or all thereof, is adjusted based on therapeutic outcome of treatment of other subjects with a particular type of tumor or cancer (optionally considering also disease severity) using a particular single agent that blocks the PD-1/PD-L1/PD-L2 pathway, or using a particular anti-PD-1/PD-L1/PD-L2 agent and a particular additional antitumor agent (combination therapy).

In some embodiments, the target cells having a phenotype of interest comprise cells expressing (e.g., expressing on the surface or within the cell, or secreting) one or more biomarkers (e.g., protein markers). In certain embodiments, the target cells express biomarkers selected from the group consisting of CD4, CD8, CD11b, CD11c, CD15, CD16, CD19, CD25, CD56, CD68, CD80, CD123, CD138, CD163, CTLA-4, Foxp3, granzyme B, HLA-A, HLA-B, HLA-C, HLA-DR, IgG-κ, IgG-λ, Ki67, LDH, MPO, OX40 (CD134), PD-1, PD-L1, PD-L2 and pSTAT1. In some embodiments, the target cells express at least 5, 10, 15, 20 or 25, or all, of the biomarkers described herein.

In some embodiments, the target cells comprise immune cells (e.g., adaptive immune cells and/or innate immune cells) and/or tumor cells, or all thereof. In certain embodiments, the target cells comprise at least 5, or all, of the following types of cells:
  (1) T cells (e.g., cytotoxic and/or regulatory T cells) expressing CD4, CD8, CD25, CTLA-4, Foxp3, granzyme B, Ki67, OX40, PD-1 or pSTAT1, or any combination or all thereof;
  (2) B cells expressing CD19 and/or CD80;
  (3) plasma cells (plasma/effector B cells) expressing CD138;
  (4) macrophages expressing CD11b. CD16, CD68, CD163, PD-L1 or PD-L2, or any combination or all thereof;

(5) dendritic cells expressing CD11c, CD68, CD123, PD-L1 or PD-L2, or any combination or all thereof;
(6) natural killer (NK) cells expressing CD16, CD56 or granzyme B, or any combination or all thereof;
(7) granulocytes (e.g., neutrophils) expressing CD15, CD16 or MPO, or any combination or all thereof;
(8) monocytes expressing CD16 and/or CD80; and
(9) tumor cells expressing PD-L1, PD-L2 or CD15, or any combination or all thereof.

The biomarkers, or the target cells expressing the biomarkers, can be detected using any suitable methodology and reagents. In certain embodiments, the biomarkers, or the target cells expressing the biomarkers, are detected by staining using antibodies that specifically bind to the biomarkers.

In some embodiments, the location of the target cells in the tumor microenvironment of the sample comprises a location, or location, at the invasive tumor margin (e.g., in a connective tissue surrounding the tumor) and/or a location, or location, within the tumor parenchyma (within the tumor). In certain embodiments, staining for S100 is used to delineate the invasive tumor margin (S100-negative) from the tumor parenchyma (S100-positive).

The ability of the immune system to attack tumor cells can be significantly influenced by the density and proximity of cells having a phenotype of interest in the tumor microenvironment. For example, immune cells can change their activity depending on their proximity to other immune cells and/or tumor cells. In certain embodiments, the density of the spatially resolved target cells in the sample comprises density of cells expressing CD8, CD11b, CD68, granzyme B, Ki67, PD-1, PD-L1, PD-L2 and pSTAT1 at the invasive tumor margin and within the tumor parenchyma. In further embodiments, the proximity between spatially resolved target cells of interest in the sample comprises proximity between PD-1-expressing cells (e.g., T cells) and PD-L1-expressing cells (e.g., immune cells and/or tumor cells) at the invasive tumor margin and within the tumor parenchyma.

In some embodiments, the following substitutions of phrases can be made:
the phrase "target cells having a phenotype of interest" can be substituted with the phrase "biomarkers of interest";
the phrase "location of the target cells in the tumor microenvironment of the sample (spatial resolution of the target cells)" can be substituted with the phrase "location of the biomarkers in the tumor microenvironment of the sample (spatial resolution of the biomarkers)";
the phrase "density of the spatially resolved target cells in the sample" can be substituted with the phrase "density of the spatially resolved biomarkers in the sample"; and
the phrase "proximity between spatially resolved target cells of interest in the sample" can be substituted with the phrase "proximity between spatially resolved biomarkers of interest in the sample".

Accordingly, in certain embodiments the density of the spatially resolved target cells in the sample comprises cellular density (e.g., in cells/mm$^2$) of biomarkers of interest at the invasive tumor margin and within the tumor parenchyma in the sample obtained from the subject prior to treatment or during treatment.

In some embodiments, the biological sample comprises tissue and/or blood. In certain embodiments, the biological sample comprises tissue that is fixed with formalin and embedded in paraffin wax before being sectioned, and wherein the formalin-fixed, paraffin-embedded (FFPE) tissue sections are de-paraffinized and treated (e.g., with heat) for antigen retrieval prior to immunohistochemical staining.

In further embodiments, the biological sample comprises a tumor sample. In certain embodiments, the tumor sample comprises an invasive tumor margin and/or tumor parenchyma. In additional embodiments, the tumor sample comprises a primary tumor and/or a secondary (metastatic) tumor.

In certain embodiments, the tumor or cancer of the subject is a solid tumor. In other embodiments, the tumor or cancer of the subject is a hematological malignancy. In additional embodiments, the tumor or cancer of the subject is a tumor or cancer of the brain (e.g., glioma or glioblastoma), head or neck (e.g, mouth, throat or thyroid), gastrointestinal tract (e.g., esophagus, stomach, small or large intestine, colon or rectum), lung (e.g., small cell lung cancer [SCLC] or non-small cell lung cancer [NSCLC], such as squamous NSCLC or non-squamous NSCLC), pancreas, liver, kidney (e.g., renal cell cancer), bladder, breast (e.g., triple-negative breast cancer), uterus, cervix, ovary, prostate (e.g., castration-resistant prostate cancer), testicle, skin (e.g., melanoma, such as metastatic melanoma), epithelial tissue or cells (e.g., gastric carcinoma, colorectal carcinoma, hepatocellular carcinoma, renal cell carcinoma, urothelial bladder cancer, endometrial cancer, or squamous cell carcinoma [e.g., of the head or neck]), or hematopoietic or lymphoid tissue or cells (e.g., leukemia [e.g., acute myeloid leukemia or chronic lymphocytic leukemia], lymphoma [e.g., Hodgkin's lymphoma or non-Hodgkin's lymphoma], myeloma [e.g., multiple myeloma], or myelodysplastic syndrome).

In some embodiments, the subject is a mammal, such as a primate (e.g., a human, a chimpanzee or a monkey), a rodent (e.g., a rat, a mouse, a gerbil or a hamster), a lagomorph (e.g., a rabbit), a swine (e.g., a pig), an equine (e.g., a horse), a canine (e.g., a dog) or a feline (e.g., a cat). In certain embodiments, the subject is a human (a human subject can also be called a "patient"). In other embodiments, the subject is a non-human mammal. A non-human subject can be studied in, e.g., drug discovery or development, or can be a patient in veterinary medicine.

In some embodiments, the overall score correlates to the strength or ability of the subject's immune system to attack tumor cells. In further embodiments, the overall score correlates to a probability or likelihood that the subject will respond to treatment with a single agent that blocks an immune checkpoint. In certain embodiments, the overall score correlates to a probability or likelihood that the subject will respond to treatment with a single agent that blocks the PD-1/PD-L1/PD-L2 pathway. In some embodiments:
(1) if the overall score is equal to or greater than a threshold score, the overall score indicates or predicts that the subject will respond to treatment with a single agent that blocks the PD-1/PD-L1/PD-L2 pathway (the subject is predicted to be a responder to PD-1/PD-L1/PD-L2 blockade therapy); or
(2) if the overall score is less than a threshold score, the overall score indicates or predicts that the subject will not respond to treatment with a single agent that blocks the PD-1/PD-L1/PD-L2 pathway (the subject is predicted to be a progressor or non-responder to PD-1/PD-L1/PD-L2 blockade therapy).

In certain embodiments, the method correctly predicts that a subject will respond to treatment with a single agent that blocks the PD-1/PD-L1/PD-L2 pathway at least about 70%, 75%, 80%, 85%, 90%, 95% or 98% (e.g., at least about 90% or 95%) of the time (accuracy of prediction). In other embodiments, the method correctly predicts that a subject will not respond to treatment with a single agent that blocks the PD-1/PD-L1/PD-L2 pathway at least about 70%, 75%, 80%, 85%, 90%, 95% or 98% (e.g., at least about 90% or 95%) of the time (accuracy of prediction).

In additional embodiments, the method further comprises:
(1) if the overall score is equal to or greater than a threshold score:
  (a) administering to the subject an effective amount of a single agent that blocks the PD-1/PD-L1/PD-L2 pathway based on the overall score for the sample obtained from the subject prior to treatment; or
  (b) if the subject is initially treated with an anti-PD-1/PD-L1/PD-L2 agent, continuing administration of the same single agent that blocks the PD-1/PD-L1/PD-L2 pathway based on the overall score for the sample obtained from the subject during treatment; or
  (c) if the subject is initially provided combination therapy, discontinuing administration of at least one other antitumor agent and continuing administration of the same agent that blocks the PD-1/PD-L1/PD-L2 pathway based on the overall score for the sample obtained from the subject during treatment; or
(2) if the overall score is less than a threshold score:
  (a) administering to the subject an effective amount of an agent that blocks the PD-1/PD-L1/PD-L2 pathway and an effective amount of at least one other antitumor agent (combination therapy) based on the overall score for the sample obtained from the subject prior to treatment; or
  (b) if the subject is initially treated with an anti-PD-1/PD-L1/PD-L2 agent, administering to the subject an effective amount of at least one other antitumor agent, and administering the same agent (its dose and/or dosing frequency can be adjusted [e.g., increased]) or a different agent that blocks the PD-1/PD-L1/PD-L2 pathway, based on the overall score for the sample obtained from the subject during treatment; or
  (c) if the subject is initially provided combination therapy, administering the same agent (the dose and/or dosing frequency can be adjusted [e.g., increased]) or a different agent that blocks the PD-1/PD-L1/PD-L2 pathway, and administering at least one other antitumor agent that may be the same as (the dose and/or dosing frequency can be adjusted [e.g., increased]) or different from the at least one other antitumor agent initially provided, based on the overall score for the sample obtained from the subject during treatment.

The method described herein can be performed at the initial decision point to guide selection of treatment of a subject with a tumor or cancer, and/or during treatment to monitor response of the subject to the current treatment regimen. FIG. 1 is a flowchart of an embodiment of the present method. In some embodiments, the method is performed:
(1) on a biological sample obtained from the subject prior to treatment to guide decision on selection of treatment with a single agent that blocks the PD-1/PD-L1/PD-L2 pathway, or with an agent that blocks the PD-1/PD-L1/PD-L2 pathway and at least one other antitumor agent (combination therapy); and
(2) on at least one biological sample obtained from the subject during treatment to monitor response of the subject to the current treatment regimen and to guide decision on selection of treatment with a single-agent PD-1/PD-L1/PD-L2 blockade therapy or with a combination therapy.

Results of the analysis of the sample from the subject can be compared to information stored in a database. The information stored in the database can include without limitation the profile (e.g., the density and proximity profile) of spatially resolved immune cells and tumor cells having certain phenotypes (e.g., expressing certain biomarkers) for subjects having a wide range of tumors and cancers, and the therapeutic outcome of treatment of subjects with a particular type of tumor or cancer using a particular single agent that blocks the PD-1/PD-L1/PD-L2 pathway, or using a particular anti-PD-1/PD-L1/PD-L2 agent and a particular additional antitumor agent (combination therapy). Such information can be obtained in pre-clinical testing (of non-human subjects), clinical trial or clinical practice, or any combination or all thereof. The present method can be used to correlate the immune and tumor cell profile (e.g., the density and proximity profile) relating to different phenotypes (e.g., different biomarkers) for subjects having different types of tumors and cancers to different responses to a (or a particular) single-agent therapy or a (or a particular) combination therapy. In certain embodiments, the overall score correlates to a probability that, or predicts whether, the subject will respond to treatment with a particular single agent that blocks the PD-1/PD-L1/PD-L2 pathway, or with a particular anti-PD-1/PD-L1/PD-L2 agent and a particular additional antitumor agent.

In some embodiments, the method further comprises:
(1) comparing the density and proximity profile and the overall score of the subject to the density and proximity profile and the overall score of other subjects with the same type of tumor or cancer (and optionally substantially the same disease severity) stored in a database, wherein the database further stores the therapeutic outcome of treatment of the other subjects with a particular single agent that blocks the PD-1/PD-L1/PD-L2 pathway, or with a particular anti-PD-1/PD-L1/PD-L2 agent and a particular additional antitumor agent; and
(2) based on the comparison, administering to the subject:
  (a) an effective amount of a single agent, or a particular single agent, that blocks the PD-1/PD-L1/PD-L2 pathway; or
  (b) an effective amount of an agent, or a particular agent, that blocks the PD-1/PD-L1/PD-L2 pathway, and an effective amount of an additional antitumor agent, or a particular additional antitumor agent (combination therapy).

The results of the analysis of the sample from the subject and the outcome of the treatment of the subject with the selected single-agent therapy or combination therapy can be stored in the database and can be used to improve the method described herein. For example, such results and outcome can be utilized to improve algorithms used to calculate the density score, the proximity score and the overall score, and to predict whether a subject with a particular type of tumor or cancer will respond to a (or a particular) single-agent therapy or a (or a particular) combination therapy.

The present method aids in selecting the optimal therapy, whether a single-agent therapy or a combination therapy, from the beginning of the treatment process. Patients with late-stage cancer (e.g., stage III or IV) may be given a prognosis of a limited amount of time to live and may have time for only a single course of therapy. Furthermore, the survival term of cancer patients correlates with the efficacy of the first-line (initial) therapy.

The method described herein has a range of applications. The present method can be applied in, e.g., diagnosis (e.g., identification of candidates for single-agent immune checkpoint [e.g., PD-1/PD-L1/PD-L2] blockade therapy or combination therapy and determination of whether relapse or resistance of a tumor or cancer has occurred), monitoring (e.g., determination of whether the same or a different single-agent immune checkpoint [e.g., PD-1/PD-L1/PD-L2] blockade therapy or combination therapy should be used), clinical practice (e.g., selection of a [or a particular] single-agent immune checkpoint [e.g., PD-1/PD-L1/PD-L2] blockade therapy or a [or a particular] combination therapy for a particular type of tumor or cancer), clinical trial design (e.g., stratification and selection of patients and selection of single-agent or combination therapies having the greatest chance of success in clinical trial), drug discovery (e.g., identification of new biomarkers and validation of cancer immunotherapy targets besides the PD-1/PD-L1/PD-L2 pathway), and drug development (e.g., development of effective immune checkpoint [e.g., PD-1/PD-L1/PD-L2] blockade agents and combination therapies for particular types of tumors and cancers). As a non-limiting example, the present method can be used to predict whether a subject will respond to treatment with a cancer vaccine prior to administration of the vaccine. In addition, the method can be used to see whether a subject has an increased chance of responding to treatment with a cancer vaccine after administration of the vaccine.

In certain embodiments, the present method is used to stratify subjects as responders or non-responders to PD-1/PD-L1/PD-L2 blockade therapy and to select subjects in clinical practice, in the design of a clinical trial, or in drug discovery or development, whether relating to a (or a particular) single-agent therapy or a (or a particular) combination therapy. In further embodiments, the method is used to guide or effect treatment decision in clinical practice, in a clinical trial, or in drug discovery or development, whether relating to a (or a particular) single-agent therapy or a (or a particular) combination therapy. The method can be used to identify a subject with a particular type of tumor or cancer that will respond to treatment with a particular single anti-PD-1/PD-L1/PD-L2 agent (single-agent therapy), or with a particular anti-PD-1/PD-L1/PD-L2 agent and a particular additional antitumor agent (combination therapy).

The agent that blocks the PD-1/PD-L1/PD-L2 pathway can inhibit PD-1, PD-L1 or PD-L2, or any combination thereof. In some embodiments, the agent that blocks the PD-1/PD-L1/PD-L2 pathway is selected from the group consisting of anti-PD-1 antibodies (e.g., nivolumab [BMS-936558, MDX-1106 or ONO-4538], pembrolizumab [lambrolizumab or MK-3475], pidilizumab [CT-011] and MEDI-0680 [AMP-514]), anti-PD-1 fusion proteins (e.g., AMP-224 [containing an $F_c$ antibody domain and PD-L2]), anti-PD-L1 antibodies (e.g., BMS-936559 [MDX-1105], MEDI-4736, MPDL3280A [RG7446] and MSB0010718C), and analogs, derivatives, fragments and salts thereof. In certain embodiments, the agent that blocks the PD-1/PD-L1/PD-L2 pathway is an anti-PD-1 agent (e.g., an anti-PD-1 antibody, such as nivolumab or pembrolizumab).

In some embodiments, the at least one other antitumor agent, or the additional antitumor agent, is selected from the group consisting of cytotoxic agents, immune system stimulators, other immune checkpoint inhibitors, angiogenesis inhibitors, targeted antitumor therapeutics (including immunotherapeutics), and other kinds of antitumor agents (including cancer vaccines). In certain embodiments, the at least one other antitumor agent, or the additional antitumor agent, comprises another immune checkpoint inhibitor (e.g., a CTLA-4 inhibitor, such as ipilimumab) and/or an immune system stimulator (e.g., a TLR9 agonist, such as agatolimod).

In some embodiments, the at least one other antitumor agent, or the additional antitumor agent, is selected from the group consisting of:
(1) cytotoxic agents, including without limitation:
  (i) alkylating agents, such as aziridines (e.g., diaziquone, mytomycin and thiotepa), nitrogen mustards (e.g., mannomustine, mustine [mechlorethamine], aniline mustard, bendamustine, benzoic acid mustard, chlorambucil, C6-galactose mustard, melphalan, ossichlorin [nitromin], prednimustine, uramustine, nitrogen mustard carbamates [e.g., estramustine], and oxazaphosphorines [e.g., cyclophosphamide, ifosfamide, mafosfamide, and trofosfamide]), nitrosoureas (e.g., carmustine, fotemustine, lomustine, nimustine, N-nitroso-N-methylurea, ranimustine, semustine and streptozotocin), platinum-containing compounds (e.g., cisplatin, carboplatin and oxaliplatin), alkylsulfonates (e.g., busulfan, mannosulfan and treosulfan), hydrazines (e.g., dacarbazine and procarbazine), imidazotetrazines (e.g., mitozolomide and temozolomide), and triazines (e.g., hexamethylmelamine [altretamine]);
  (ii) cytotoxic antibiotics, such as anthracyclines (e.g., aclarubicin, daunorubicin, doxorubicin, epirubicin, idarubicin, mitoxantrone, pirarubicin and valrubicin), actinomycins (e.g., actinomycin D), bleomycins (e.g., bleomycins $A_2$ and $B_2$), mitomycins (e.g., mitomycin C), and plicamycins;
  (iii) anti-metabolites, such as anti-folates (e.g., aminopterin, methotrexate and pemetrexed), deoxynucleoside analogs (e.g., 5-azacytidine [azacitidine], 5-aza-2'-deoxycytidine [decitabine], cladribine, clofarabine, cytarabine, decitabine, fludarabine, gemcitabine, nelarabine and pentostatin), fluoropyrimidines (e.g., 5-fluorouracil, 5-fluoro-5'-deoxyuridine [doxifluridine] and capecitabine), and thiopurines (e.g., thioguanine, azathioprine and mercaptopurine);
  (iv) anti-microtubule agents, such as dolastatins (e.g., dolastatin 15), epothilones (e.g., epothilones A-F), taxanes (e.g., paclitaxel and docetaxel), vinca alkaloids (e.g., vinblastine, vincristine, vindesine, vinflunine and vinorelbine), colchicine, nocodazole, podophyllotoxin and rhizoxin;
  (v) histone deacetylase inhibitors, such as trichostatins (e.g., trichostatin A), romidepsin and vorinostat;
  (vi) kinase inhibitors, such as curcumin, cyclocreatine, deguelin, fostriecin, hispidin, tyrphostins (e.g., tyrphostins AG 34 and AG 879), bortezomib, erlotinib, gefitinib, imatinib, vemurafenib and vismodegib;
  (vii) topoisomerase I inhibitors, such as camptothecin, irinotecan and topotecan;
  (viii) topoisomerase II-targeting agents, such as topoisomerase II poisons (e.g., etoposide, tafluposide, teniposide, doxorubicin and mitoxantrone) and topoisomerase II inhibitors (e.g., novobiocin, merbarone and aclarubicin);
  (ix) DNA or RNA synthesis inhibitors, such as 3-amino-1,2,4-benzotriazine 1,4-dioxide, cytosine β-D-arabinofuranoside, 5,6-dichlorobenzimidazole 1-β-D-ribofuranoside, ganciclovir and hydroxyurea;
  (x) protein synthesis inhibitors, such as homoharringtonine;

(xi) cell growth and differentiation regulators, such as retinoids (e.g., all-trans retinol [vitamin A], 11-cis retinol, all-trans retinal [vitamin A aldehyde], 11-cis retinal, all-trans retinoic acid [tretinoin], 9-cis-retinoic acid [alitretinoin], 11-cis retinoic acid, 13-cis-retinoic acid [isotretinoin], all-trans retinyl esters, etretinate, acitretin, adapalene, bexarotene and tazarotene);

(xii) cell proliferation inhibitors, such as mTOR inhibitors (e.g., rapamycin [sirolimus]), apigenin, cholecalciferol (vitamin D3) and sex hormone-binding globulin;

(xiii) apoptosis inducers, such as 17-allylamino-17-demethoxygeldanamycin, melatonin, mevinolin, psoralen, thapsigargin and troglitazone; and analogs, derivatives and salts thereof;

(2) agents that stimulate the immune system, including without limitation:

(i) agonists/activators of tumor necrosis factor receptor superfamily member 4 (TNFRSF4, OX40 or CD134), such as OX40-targeting antibodies (e.g., MEDI-6469 and 9B12) and ligands for OX40 (e.g., OX40L);

(ii) agonists/activators of TNFRSF member 5 (TNFRSF5 or CD40), such as CD40-targeting antibodies (e.g., dacetuzumab and CP-870,893) and ligands for CD40 (e.g., CD40[CD154]);

(iii) agonists/activators of TNFRSF member 9 (TNFRSF9, 4-1BB or CD137), such as 4-1BB-targeting antibodies (e.g., urelumab [BMS-663513] and PF-05082566) and ligands for 4-1BB (e.g., 4-1BBL);

(iv) agonists/activators of TNFRSF member 18 (TNFRSF18, glucocorticoid-induced TNFR-related protein [GITR] or CD357), such as GITR-targeting antibodies (e.g., DTA-1 and TRX518) and ligands for GITR (e.g., GITRL);

(v) agonists/activators of toll-like receptors (TLRs), such as ligands for TLR9 (e.g., unmethylated CpG oligodeoxynucleotides [CpG ODNs], such as agatolimod); and analogs, derivatives, fragments and salts thereof;

(3) other agents that block immune checkpoints, including without limitation:

(i) inhibitors of cytotoxic T lymphocyte-associated protein 4 (CTLA-4) receptor or ligands thereof, such as anti-CTLA-4 antibodies (e.g., ipilimumab and tremelimumab);

(ii) inhibitors of killer cell immunoglobulin-like receptors (KIRs) or ligands thereof, such as anti-KIR antibodies (e.g., lirilumab [IPH2102 or BMS-986015]);

(iii) inhibitors of lymphocyte activation gene 3 (LAG-3) receptor or ligands thereof, such as anti-LAG-3 antibodies (e.g., BMS-986016);

(iv) inhibitors of indoleamine 2,3-dioxygenase (IDO or IDO1), such as indoximod (1-methyl-D-tryptophan or NLG-8189), NLG-919, INCB024360, α-methyl-tryptophan, β-carboline (9H-pyrido[3,4-b]indole or norharmane), and cyclooxygenase 2 (COX-2) inhibitors (e.g., coxibs [such as apricoxib, celecoxib, etoricoxib, lumiracoxib, parecoxib, rofecoxib and valdecoxib], which down-regulate the expression of IDO); and analogs, derivatives, fragments and salts thereof;

(4) angiogenesis inhibitors, including without limitation inhibitors of vascular endothelial growth factors (VEGFs) (e.g., squalamine and anti-VEGF antibodies such as bevacizumab) or receptors therefor (VEGFRs) (e.g., axitinib, pazopanib, sorafenib and sunitinib), inhibitors of platelet-derived growth factors (PDGFs) (e.g., squalamine) or receptors therefor (PDGFRs) (e.g., axitinib, pazopanib, sorafenib and sunitinib), inhibitors of fibroblast growth factors (FGFs) (e.g., squalamine) or receptors therefor (FGFRs), inhibitors of angiopoietins (e.g., anti-angiopoietin antibodies such as nesvacumab) or receptors therefor, inhibitors of integrins (e.g., ALG-1001 and JSM-6427), anecortave (anecortave acetate), angiostatin (e.g., angiostatin K1-3), $\alpha_\nu\beta_3$ inhibitors (e.g., etaracizumab), berberine, bleomycins, borrelidin, carboxyamidotriazole, cartilage-derived angiogenesis inhibitors (e.g., chondromodulin I and troponin I), castanospermine, CM101, cyclopropene fatty acids (e.g., sterculic acid), α-difluoromethylornithine, endostatin, everolimus, fumagillin, genistein, interferon-α, interleukin-12, itraconazole, linomide, matrix metalloproteinase (MMP) inhibitors (e.g., batimastat, cipemastat, ilomastat, marimastat, prinomastat, rebimastat, tanomastat, and tetracyclines [e.g., doxycycline, incyclinide and minocycline]), 2-methoxyestradiol, pigment epithelium-derived factor (PEDF), platelet factor-4, PPAR-γ agonists (e.g., thiazolidinediones, such as ciglitazone, lobeglitazone, netoglitazone, pioglitazone, rivoglitazone, rosiglitazone and troglitazone), prolactin, sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, Withaferin A, and analogs, derivatives, fragments and salts thereof; and (5) other kinds of antitumor agents, including without limitation:

(i) drug-efflux pump inhibitors, such as P-glycoprotein inhibitors (e.g., mifepristone and verapamil);

(ii) cell adhesion inhibitors, such as cimetidine;

(iii) Golgi apparatus disruptors, such as brefeldins (e.g., brefeldin A);

(iv) ionizing radiation, such as X-ray;

(v) radiation sensitizers of tumor cells, such as poly (ADP-ribose) polymerase (PARP) inhibitors (e.g., 4-amino-1,8-naphthalimide), berberine and indomethacin;

(vi) enhancers of cell survival after treatment with cytotoxic drugs or radiation, such as pifithrin-α;

(vii) vaccines, such as those that stimulate the immune system to recognize proteins produced by tumor cells and thereby to attack tumor cells; and analogs, derivatives and salts thereof.

A particular antitumor agent may have more than one mechanism of action and may be classified in more than one category.

The at least one other antitumor agent, or the additional antitumor agent, can also be selected for more targeted therapy of tumors and cancers. Table 1 below lists non-limiting examples of antitumor agents designed for targeted therapy.

TABLE 1

Representative Antitumor Agents for Targeted Therapy

| Tumor/Cancer | Targeted Antitumor Therapeutics |
|---|---|
| Breast cancer | selective estrogen receptor antagonists (e.g., tamoxifen, 4-hydroxytamoxifen, raloxifene, toremifene, fulvestrant) |
| Breast cancer (post-menopausal) | aromatase inhibitors (e.g., anastrozole, letrozole, exemestane, formestane, megestrol acetate) |
| Breast cancer | androgens (testosterone-like) (e.g., fluoxymesterone) |
| Breast cancer | anti-Her2/neu receptor monoclonal antibodies (e.g., trastuzumab) |
| Breast cancer and other solid tumors | dual inhibitors of Her2/neu receptor and epidermal growth factor receptor (EGFR) (e.g., lapatinib, neratinib) |
| Ovarian cancer | poly(ADP-ribose) polymerase (PARP) inhibitors (e.g., olaparib) |
| Prostate cancer | gonadotropin-releasing hormone (GnRH) analogs (e.g., leuprolide, goserelin) |
| Prostate cancer | androgen receptor inhibitors (e.g., flutamide, bicalutamide, estrace) |
| Prostate cancer | estrogen agonists (e.g., diethylstilbestrol, estrace, polyestradiol phosphate) |
| Breast, endometrial and prostate cancers | progestins (progesterone-like) (e.g., megestrol acetate, medroxyprogesterone acetate) |
| Breast, colorectal, renal and non-small cell lung cancers, and brain tumors | anti-VEGF monoclonal antibodies (e.g., bevacizumab) |
| Non-small cell lung cancer | EGFR tyrosine kinase inhibitors (e.g., afatinib, gefitinib, erlotinib) |
| Non-small cell lung cancer | anaplastic lymphoma kinase (ALK) inhibitors (e.g., ceritinib, crizotinib) |
| Colorectal, non-small cell lung, and squamous cell head and neck cancers | anti-EGFR monoclonal antibodies (e.g., cetuximab, necitumumab, nimotuzumab, panitumumab) |
| Colorectal, gastric and non-small cell lung cancers | anti-VEGFR monoclonal antibodies (e.g., ramucirumab) |
| Melanoma | B-Raf inhibitors (e.g., vemurafenib, dabrafenib) and/or MEK inhibitors (e.g., cobimetinib, trametinib) |
| Basal cell carcinoma | Hedgehog signaling pathway inhibitors (e.g., sonidegib [erismodegib]) |
| Thyroid cancer | VEGFR inhibitors (e.g., lenvatinib) |
| Acute myelogenous leukemia | anti-CD33 antibody-drug conjugates (e.g., gemtuzumab ozogamicin) |
| Chronic myelogenous leukemia & gastrointestinal stromal tumor | Bcr-Abl tyrosine kinase inhibitors (e.g., bafetinib, bosutinib, dasatinib, imatinib, nilotinib, ponatinib) |
| Chronic lymphocytic leukemia & non-Hodgkin's lymphoma | anti-CD20 monoclonal antibodies (e.g., obinutuzumab, ofatumumab, rituximab, tositumomab, $^{90}$Y- or $^{111}$In-ibritumomab tiuxetan); and/or anti-CD52 monoclonal antibodies (e.g., alemtuzumab) |
| Acute lymphoblastic leukemia & non-Hodgkin's lymphoma | anti-CD19 monoclonal antibodies (e.g., blinatumomab) |
| Hodgkin's lymphoma and anaplastic large-cell lymphoma | anti-CD30 antibody-drug conjugates (e.g., brentuximab vedotin) |
| Multiple myeloma | proteasome inhibitors (e.g., bortezomib, carfilzomib); and/or histone deacetylase inhibitors (e.g., panobinostat) |
| Multiple myeloma | anti-angiogenic and anti-proliferative (e.g., lenalidomide, pomalidomide) |
| Multiple myeloma | antibodies targeting CD38 (e.g., daratumumab) or signaling lymphocytic activation molecule F7 (SLAMF7) (e.g., elotuzumab) |
| Cancer stem cells | salinomycin |

The method described herein can be automated. Accordingly, in some embodiments the method is implemented with a computer system (e.g., a server, a desktop computer, a laptop, a tablet or a smartphone) comprising at least one processor. The computer system can be configured or provided with algorithms, instructions or codes for performing the method which are executable by the at least one processor. The computer system can generate a report containing information on any or all aspects relating to the method, including results of the analysis of the biological sample from the subject. The disclosure further provides a non-transitory computer-readable medium encoded with computer-executable instructions for performing the present method.

Figure 2:
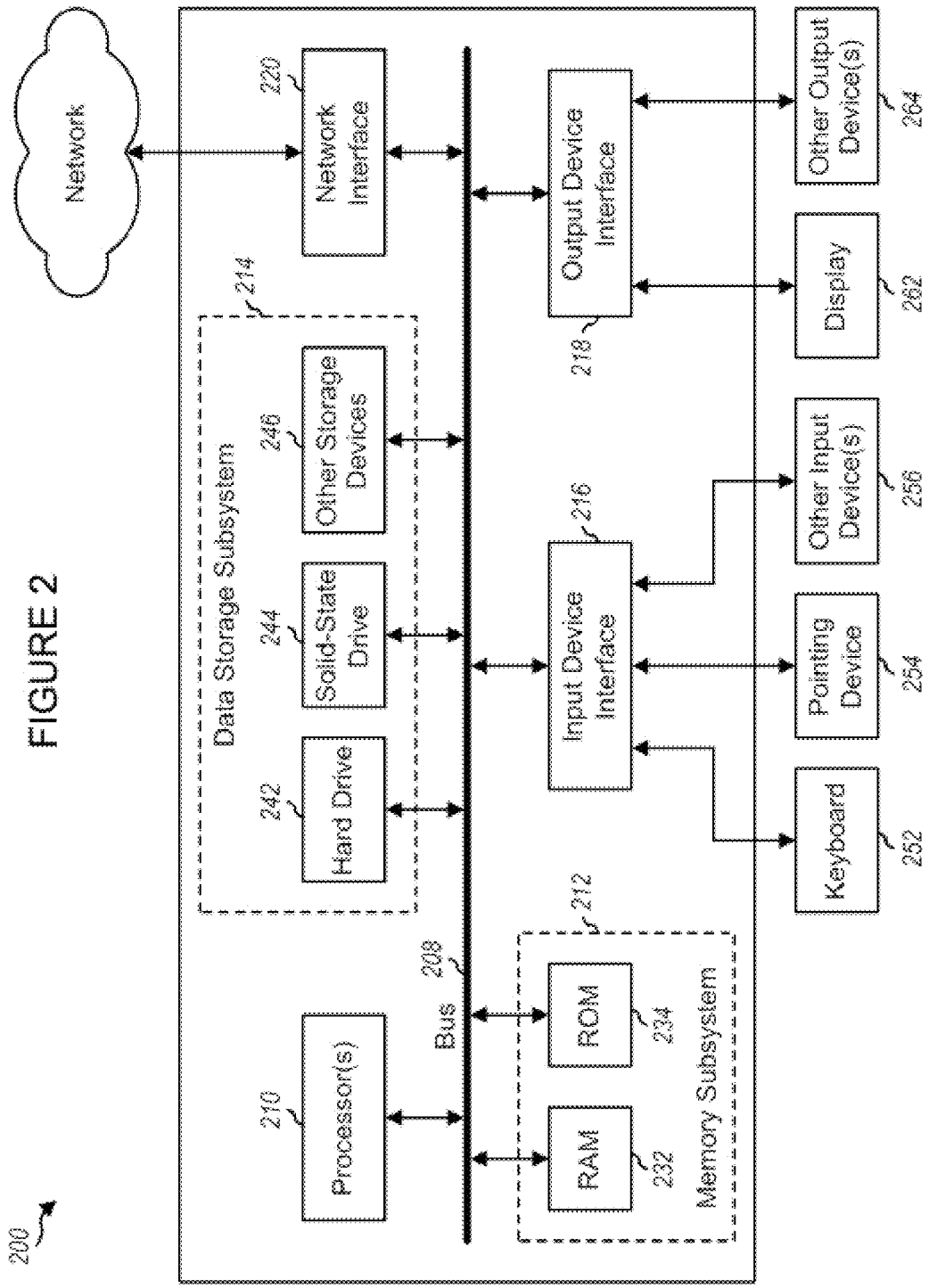
FIG. 2 is a block diagram of an embodiment of a computer system that can be used to implement the method of analyzing a tumor sample.

FIG. 2 is a block diagram of an embodiment of a computer system 200 that can be used to implement the method of analyzing a tumor sample described herein. System 200 includes a bus 208 that interconnects major subsystems such as one or more processors 210, a memory subsystem 212, a data storage subsystem 214, an input device interface 216, an output device interface 218, and a network interface 220. Processor(s) 210 perform many of the processing functions for system 200 and communicate with a number of peripheral devices via bus 208.

Memory subsystem 212 can include, e.g., a RAM 232 and a ROM 234 used to store codes/instructions/algorithms and data that implement various aspects of the present method. Data storage subsystem 214 provides non-volatile storage for program codes/instructions/algorithms and data that implement various aspects of the present method, and can include, e.g., a hard disk drive 242, a solid-state drive 244, and other storage devices 246 (e.g., a CD-ROM drive, an optical drive, a removable-media drive, and so on). Memory subsystem 212 and/or data storage subsystem 214 can be used to store, e.g., the density and proximity profile and the overall score of subjects with a particular type of tumor or cancer, and the therapeutic outcome of treatment of those subjects with a particular single agent that blocks the PD-1/PD-L1/PD-L2 pathway, or with a particular anti-PD-1/PD-L1/PD-L2 agent and a particular additional antitumor agent. The codes/instructions/algorithms for implementing certain aspects of the present method can be operatively disposed in memory subsystem 212 or stored in data storage subsystem 214.

Input device interface 216 provides interface with various input devices, such as a keyboard 252, a pointing device 254 (e.g., a mouse, a trackball, a scanner, a pen, a tablet, a touch pad or a touch screen), and other input device(s) 256. Output device interface 218 provides an interface with various output devices, such as a display 262 (e.g., a CRT or an LCD) and other output device(s) 264. Network interface 220 provides an interface for computer system 200 to communicate with other computer systems coupled to a network to which system 200 is coupled.

Other devices and/or subsystems (not shown) can also be coupled to computer system 200. In addition, it is not necessary for all of the devices and subsystems shown in FIG. 2 to be present to practice the method described herein. Furthermore, the devices and subsystems can be interconnected in configurations different from that shown in FIG. 2.

Those of ordinary skill in the art would understand that the various embodiments of the method described herein can be implemented in electronic hardware, computer software, or a combination of both (e.g., firmware). Whether the present method is implemented in hardware and/or software may depend on, e.g., the particular application and design constraints imposed on the overall system. Ordinary artisans can implement the present method in varying ways depending on, e.g., particular application and design constraints, but such implementation decisions do not depart from the scope of the present disclosure.

The computer programs/algorithms for performing the present method can be implemented with, e.g., a general-purpose processor, a digital signal processor (DSP), an application-specific integrated circuit (ASIC), a field-programmable gate array (FPGA), or other programmable logic device, discrete gate or transistor logic, discrete hardware components, or any combination thereof designed to perform the functions and steps described herein. A general-purpose processor can be a microprocessor, but alternatively the processor can be any conventional processor, controller, microcontroller or state machine. A processor can also be implemented as a combination of computing devices, e.g., a combination of a DSP and a microprocessor, a plurality of microprocessors, one or more microprocessors in conjunction with a DSP core, or any other such configuration.

The steps of the present method, or the computer programs/algorithms for performing the method, can be embodied directly in hardware, in a software module executed by a processor, or in a combination of hardware and software (e.g., firmware). A software module can reside in, e.g., RAM memory, flash memory, ROM memory, EPROM memory, EEPROM memory, registers, a hard drive, a solid-state drive, a removable disk or disc, a CD-ROM, or any other form of storage medium known in the art. An exemplary storage medium is coupled to the processor such that the processor can read information from, and write information to, the storage medium. Alternatively, the storage medium can be integral to the processor. The processor and the storage medium can reside in, e.g., an ASIC, which in turn can reside in, e.g., a user terminal. In the alternative, the processor and the storage medium can reside as discrete components in, e.g., a user terminal.

In one or more exemplary designs, the functions for carrying out the method described herein can be implemented in hardware, software, firmware or any combination thereof. If implemented in software, the functions can be stored on or transmitted over a computer-readable medium as instructions or codes. Computer-readable media include without limitation computer storage media and communication media, including any medium that facilitates transfer of a computer program/algorithm from one place to another. A storage medium can be any available medium that can be accessed by a general-purpose or special-purpose computer or processor. As a non-limiting example, computer-readable media can comprise RAM, ROM, EEPROM, CD-ROM or other optical disc storage, magnetic disk storage or other magnetic storage devices, or any other medium that can be used to carry or store a computer program/algorithm in the form of instructions/codes and/or data structures and that can be accessed by a general-purpose or special-purpose computer or processor. In addition, any connection is deemed a computer-readable medium. For example, if the software is transmitted from a website, a server or other remote source using a coaxial cable, fiber optic cable, twisted pair, digital subscriber line (DSL), or a wireless technology such as infrared, radio wave or microwave, then the coaxial cable, fiber optic cable, twisted pair, DSL, or wireless technology such as infrared, radio wave or microwave are computer-readable media. Discs and disks include without limitation compact disc (CD), laser disc, optical disc, digital versatile disc (DVD), blu-ray disc, hard disk and floppy disk, where discs normally reproduce data optically using a laser, while disks normally reproduce data magnetically. Combinations of the above are also included within the scope of computer-readable media.

REPRESENTATIVE EMBODIMENTS

The following embodiments of the disclosure are provided by way of example only:

1. A method of analyzing a biological sample from a subject that has a tumor or cancer, comprising:
 (1) determining, for target cells having a phenotype of interest:
  (a) location of the target cells in the tumor microenvironment of the sample (spatial resolution of the target cells);
  (b) density of the spatially resolved target cells in the sample; and
  (c) proximity between spatially resolved target cells of interest in the sample; and
 (2) determining an overall score based at least in part on parameters (a) to (c).

2. The method of embodiment 1, wherein the biological sample is obtained from the subject prior to treatment or during treatment.

3. The method of embodiment 1 or 2, further comprising determining a score (density score) for the density of the spatially resolved target cells in the sample and/or a score (proximity score) for the proximity between spatially resolved target cells of interest in the sample, and wherein:
 the density score is determined based at least in part on weighting of the density of particular types of spatially resolved target cells in the sample;
 the proximity score is determined based at least in part on weighting of the proximity between particular types of spatially resolved target cells of interest in the sample; and
 the overall score is determined based at least in part on weighting of the density score and/or the proximity score.

4. The method of embodiment 3, wherein the density score (e.g., weighting to determine the density score), the proximity score (e.g., weighting to determine the proximity score), or the overall score (e.g., weighting to determine the overall score), or any combination or all thereof, is adjusted based on whether the sample is obtained from the subject prior to treatment or during treatment.

5. The method of embodiment 3 or 4, wherein the density score (e.g., weighting to determine the density score), the proximity score (e.g., weighting to determine the proximity score), or the overall score (e.g., weighting to determine the overall score), or any combination or all thereof, is adjusted based on the particular type of tumor or cancer (and optionally the disease severity) the subject has.

6. The method of any one of embodiments 3 to 5, wherein the density score (e.g., weighting to determine the density score), the proximity score (e.g., weighting to determine the proximity score), or the overall score (e.g., weighting to determine the overall score), or any combination or all thereof, is adjusted based on the location of the primary tumor and/or the location of any secondary (metastatic) tumor.

7. The method of any one of embodiments 3 to 6, wherein the density score (e.g., weighting to determine the density score), the proximity score (e.g., weighting to determine the proximity score), or the overall score (e.g., weighting to determine the overall score), or any combination or all thereof, is adjusted based on information relating to the subject, such as the ethnicity, the race, the gender, the age, the body mass index, the diet, risk factors (e.g., drinking, smoking, stress and/or inactivity), the (individual and/or family) medical history or the overall health, or any combination or all thereof, of the subject.

8. The method of any one of embodiments 3 to 7, wherein the density score (e.g., weighting to determine the density score), the proximity score (e.g., weighting to determine the proximity score), or the overall score (e.g., weighting to determine the overall score), or any combination or all thereof, is adjusted based on therapeutic outcome of treatment of other subjects with a particular type of tumor or cancer (optionally considering also disease severity) using a particular single agent that blocks the PD-1/PD-L1/PD-L2 pathway, or using a particular anti-PD-1/PD-L1/PD-L2 agent and a particular additional antitumor agent (combination therapy).

9. The method of any one of the preceding embodiments, wherein the target cells having a phenotype of interest comprise cells expressing (e.g., expressing on the surface or within the cell, or secreting) one or more biomarkers (e.g., protein markers).

10. The method of embodiment 9, wherein the target cells express biomarkers selected from the group consisting of CD4, CD8, CD11b, CD11c, CD15, CD16, CD19, CD25, CD56, CD68, CD80, CD123, CD138, CD163, CTLA-4, Foxp3, granzyme B, HLA-A, HLA-B, HLA-C, HLA-DR, IgG-κ, IgG-λ, Ki67, LDH, MPO. OX40 (CD134). PD-1, PD-L1, PD-L2 and pSTAT1.

11. The method of embodiment 10, wherein the target cells express at least 5, 10, 15, 20 or 25, or all, of the biomarkers recited in embodiment 10.

12. The method of any one of embodiments 9 to 11, wherein the target cells comprise immune cells (e.g., adaptive immune cells and/or innate immune cells) and/or tumor cells, or all thereof.

13. The method of embodiment 12, wherein the target cells comprise at least 5, or all, of the following types of cells:

(1) T cells (e.g., cytotoxic and/or regulatory T cells) expressing CD4, CD8, CD25, CTLA-4, Foxp3, granzyme B, Ki67, OX40, PD-1 or pSTAT1, or any combination or all thereof;

(2) B cells expressing CD19 and/or CD80;

(3) plasma cells (plasma/effector B cells) expressing CD138;

(4) macrophages expressing CD11b, CD16, CD68, CD163, PD-L1 or PD-L2, or any combination or all thereof;

(5) dendritic cells expressing CD11c, CD68, CD123, PD-L1 or PD-L2, or any combination or all thereof;

(6) natural killer (NK) cells expressing CD16, CD56 or granzyme B, or any combination or all thereof;

(7) granulocytes (e.g., neutrophils) expressing CD15, CD16 or MPO, or any combination or all thereof;

(8) monocytes expressing CD16 and/or CD80; and (9) tumor cells expressing PD-L1, PD-L2 or CD15, or any combination or all thereof.

14. The method of any one of embodiments 9 to 13, wherein the biomarkers, or the target cells expressing the biomarkers, are detected by staining using antibodies that specifically bind to the biomarkers.

15. The method of any one of the preceding embodiments, wherein the location of the target cells in the tumor microenvironment of the sample comprises a location at the invasive tumor margin (e.g., in a connective tissue surrounding the tumor) and/or a location within the tumor parenchyma (tumor).

16. The method of embodiment 15, wherein staining for S100 is used to delineate the invasive tumor margin (S100-negative) from the tumor parenchyma (S100-positive).

17. The method of any one of the preceding embodiments, wherein the density of the spatially resolved target cells in the sample comprises density of cells expressing CD8, CD11b, CD68, granzyme B, Ki67, PD-1, PD-L1, PD-L2 and pSTAT1 at the invasive tumor margin and within the tumor parenchyma.

18. The method of any one of the preceding embodiments, wherein the density of the spatially resolved target cells in the sample comprises cellular density (e.g., in cells/mm$^2$) of biomarkers of interest at the invasive tumor margin and within the tumor parenchyma in the sample obtained from the subject prior to treatment or during treatment.

19. The method of any one of the preceding embodiments, wherein the proximity between spatially resolved target cells of interest in the sample comprises proximity between PD-1-expressing cells and PD-L1-expressing cells at the invasive tumor margin and within the tumor parenchyma.

20. The method of any one of the preceding embodiments, wherein:

the phrase "target cells having a phenotype of interest" can be substituted with the phrase "biomarkers of interest";

the phrase "location of the target cells in the tumor microenvironment of the sample (spatial resolution of the target cells)" can be substituted with the phrase "location of the biomarkers in the tumor microenvironment of the sample (spatial resolution of the biomarkers)";

the phrase "density of the spatially resolved target cells in the sample" can be substituted with the phrase "density of the spatially resolved biomarkers in the sample"; and the phrase "proximity between spatially resolved target cells of interest in the sample" can be substituted with the phrase "proximity between spatially resolved biomarkers of interest in the sample".

21. The method of any one of the preceding embodiments, wherein the biological sample comprises tissue and/or blood.

22. The method of embodiment 21, wherein the biological sample comprises tissue that is fixed with formalin and embedded in paraffin wax before being sectioned, and wherein the formalin-fixed, paraffin-embedded (FFPE) tissue sections are de-paraffinized and treated (e.g., with heat) for antigen retrieval prior to immunohistochemical staining.

23. The method of any one of the preceding embodiments, wherein the biological sample comprises a tumor sample.

24. The method of embodiment 23, wherein the tumor sample comprises an invasive tumor margin and/or tumor parenchyma.

25. The method of embodiment 23 or 24, wherein the tumor sample comprises a primary tumor and/or a secondary (metastatic) tumor.

26. The method of any one of the preceding embodiments, wherein the tumor or cancer is a solid tumor or a hematological malignancy.

27. The method of any one of the preceding embodiments, wherein the tumor or cancer is a tumor or cancer of the brain (e.g., glioma or glioblastoma), head or neck (e.g, mouth, throat or thyroid), gastrointestinal tract (e.g., esophagus, stomach, small or large intestine, colon or rectum), lung (e.g., small cell lung cancer [SCLC] or non-small cell lung cancer [NSCLC], such as squamous NSCLC or non-squamous NSCLC), pancreas, liver, kidney (e.g., renal cell cancer), bladder, breast (e.g., triple-negative breast cancer), uterus, cervix, ovary, prostate (e.g., castration-resistant prostate cancer), testicle, skin (e.g., melanoma, such as metastatic melanoma), epithelial tissue or cells (e.g., gastric carcinoma, colorectal carcinoma, hepatocellular carcinoma, renal cell carcinoma, urothelial bladder cancer, endometrial cancer, or squamous cell carcinoma [e.g., of the head or neck]), or hematopoietic or lymphoid tissue or cells (e.g., leukemia [e.g., acute myeloid leukemia or chronic lymphocytic leukemia], lymphoma [e.g., Hodgkin's lymphoma or non-Hodgkin's lymphoma], myeloma [e.g., multiple myeloma], or myelodysplastic syndrome).

28. The method of any one of the preceding embodiments, wherein the subject is a mammal, such as a primate (e.g., a human, a chimpanzee or a monkey), a rodent (e.g., a rat, a mouse, a gerbil or a hamster), a lagomorph (e.g., a rabbit), a swine (e.g., a pig), an equine (e.g., a horse), a canine (e.g., a dog) or a feline (e.g., a cat).

29. The method of embodiment 28, wherein the subject is a human (a human "subject" can also be called a "patient").

30. The method of any one of the preceding embodiments, wherein the overall score correlates to the strength or ability of the subject's immune system to attack tumor cells.

31. The method of any one of the preceding embodiments, wherein the overall score correlates to a probability or likelihood that the subject will respond to treatment with a single agent that blocks an immune checkpoint.

32. The method of embodiment 31, wherein the overall score correlates to a probability or likelihood that the subject will respond to treatment with a single agent that blocks the PD-1/PD-L1/PD-L2 pathway.

33. The method of embodiment 32, wherein:
    (1) if the overall score is equal to or greater than a threshold score, the overall score indicates or predicts that the subject will respond to treatment with a single agent that blocks the PD-1/PD-L1/PD-L2 pathway (the subject is predicted to be a responder to PD-1/PD-L1/PD-L2 blockade therapy); or
    (2) if the overall score is less than a threshold score, the overall score indicates or predicts that the subject will not respond to treatment with a single agent that blocks the PD-1/PD-L1/PD-L2 pathway (the subject is predicted to be a progressor or non-responder to PD-1/PD-L1/PD-L2 blockade therapy).

34. The method of embodiment 33, further comprising:
    (1) if the overall score is equal to or greater than the threshold score:
        (a) administering to the subject an effective amount of a single agent that blocks the PD-1/PD-L1/PD-L2 pathway based on the overall score for the sample obtained from the subject prior to treatment; or
        (b) if the subject is initially treated with an anti-PD-1/PD-L1/PD-L2 agent, continuing administration of the same single agent that blocks the PD-1/PD-L1/PD-L2 pathway based on the overall score for the sample obtained from the subject during treatment; or
        (c) if the subject is initially provided combination therapy, discontinuing administration of at least one other antitumor agent and continuing administration of the same agent that blocks the PD-1/PD-L1/PD-L2 pathway based on the overall score for the sample obtained from the subject during treatment; or
    (2) if the overall score is less than the threshold score:
        (a) administering to the subject an effective amount of an agent that blocks the PD-1P/PD-L1/PD-L2 pathway and an effective amount of at least one other antitumor agent (combination therapy) based on the overall score for the sample obtained from the subject prior to treatment; or
        (b) if the subject is initially treated with an anti-PD-1/PD-L1/PD-L2 agent, administering to the subject an effective amount of at least one other antitumor agent, and administering the same agent (its dose and/or dosing frequency can be adjusted [e.g., increased]) or a different agent that blocks the PD-1/PD-L1/PD-L2 pathway, based on the overall score for the sample obtained from the subject during treatment; or
        (c) if the subject is initially provided combination therapy, administering the same agent (the dose and/or dosing frequency can be adjusted [e.g., increased]) or a different agent that blocks the PD-1/PD-L1/PD-L2 pathway, and administering at least one other antitumor agent that may be the same as (the dose and/or dosing frequency can be adjusted [e.g., increased]) or different from the at least one other antitumor agent initially provided, based on the overall score for the sample obtained from the subject during treatment.

35. The method of any one of the preceding embodiments, which is performed:
    (1) on a biological sample obtained from the subject prior to treatment to guide decision on selection of treatment with a single agent that blocks the PD-1/PD-L1/PD-L2 pathway, or with an agent that blocks the PD-1/PD-L1/PD-L2 pathway and at least one other antitumor agent (combination therapy); and
    (2) on at least one biological sample obtained from the subject during treatment to monitor response of the subject to the current treatment regimen and to guide decision on selection of treatment with a single-agent PD-1/PD-L1/PD-L2 blockade therapy or with a combination therapy.

36. The method of any one of the preceding embodiments, further comprising:
    (1) comparing the density and proximity profile and the overall score of the subject to the density and proximity profile and the overall score of other subjects with the same type of tumor or cancer (and optionally substantially the same disease severity) stored in a database, wherein the database further stores the therapeutic outcome of treatment of the other subjects with a particular single agent that blocks the PD-1/PD-L1/PD-L2 pathway, or with a particular anti-PD-1/PD-L1/PD-L2 agent and a particular additional antitumor agent; and
    (2) based on the comparison, administering to the subject:
        (a) an effective amount of a single agent, or a particular single agent, that blocks the PD-1/PD-L1/PD-L2 pathway; or
        (b) an effective amount of an agent, or a particular agent, that blocks the PD-1/PD-L1/PD-L2 pathway, and an effective amount of an additional antitumor agent, or a particular additional antitumor agent (combination therapy).

37. The method of embodiment 33, which is used to stratify subjects as responders or non-responders to PD-1/PD-L1/PD-L2 blockade therapy and to select subjects in clinical practice, in a clinical trial, or in drug discovery or development, whether relating to a (or a particular) single-agent therapy or a (or a particular) combination therapy.

38. The method of any one of embodiments 34 to 36, which is used to guide or effect treatment decision in clinical practice, in a clinical trial, or in drug discovery or development, whether relating to a (or a particular) single-agent therapy or a (or a particular) combination therapy.

39. The method of any one of the preceding embodiments, wherein the overall score correlates to a probability that, or predicts whether, the subject will respond to treatment with a particular single agent that blocks the PD-1/PD-L1/PD-L2 pathway, or with a particular anti-PD-1/PD-L1/PD-L2 agent and a particular additional antitumor agent.

40. The method of any one of embodiments 8 to 39, wherein the agent that blocks the PD-1/PD-L1/PD-L2 pathway is selected from the group consisting of anti-PD-1 antibodies (e.g., nivolumab [BMS-936558, MDX-1106 or ONO-4538], pembrolizumab [lambrolizumab or MK-3475], pidilizumab [CT-011] and MEDI-0680 [AMP-514]), anti-PD-1 fusion proteins (e.g., AMP-224 [containing an $F_c$ antibody domain and PD-L2]), anti-PD-L1 antibodies (e.g., BMS-936559 [MDX-1105], MEDI-4736, MPDL3280A [RG7446] and MSB0010718C), and analogs, derivatives, fragments and salts thereof.

41. The method of embodiment 40, wherein the agent that blocks the PD-1/PD-L1/PD-L2 pathway is an anti-PD-1 agent (e.g., an anti-PD-1 antibody, such as nivolumab or pembrolizumab).

42. The method of any one of embodiments 8 to 41, wherein the at least one other antitumor agent, or the additional antitumor agent, is selected from the group consisting of cytotoxic agents, immune system stimulators, other immune checkpoint inhibitors, angiogenesis inhibitors, targeted antitumor therapeutics (including immunotherapeutics), and other kinds of antitumor agents (including cancer vaccines).

43. The method of embodiment 42, wherein the at least one other antitumor agent, or the additional antitumor agent, comprises another immune checkpoint inhibitor (e.g., a CTLA-4 inhibitor, such as ipilimumab) and/or an immune system stimulator (e.g., a TLR9 agonist, such as agatolimod).

44. The method of any one of the preceding embodiments, further comprising generating a report containing information relating to the method.

45. The method of any one of the preceding embodiments, which is implemented with a computer system (e.g., a server, a desktop computer, a laptop, a tablet or a smartphone) comprising at least one processor.

46. The method of embodiment 45, wherein the computer system is configured or provided with algorithms, instructions or codes for performing the method which are executable by the at least one processor.

47. A method of identifying a subject with a tumor or cancer as a responder or non-responder to treatment with a single agent that blocks the PD-1/PD-L1/PD-L2 pathway, which comprises the method of embodiment 33, and which is performed on a biological sample obtained from the subject prior to treatment or during treatment.

48. The method of embodiment 47, which is performed on a sample obtained from the subject during treatment to monitor response of the subject to treatment with a single agent that blocks the PD-1/PD-L1/PD-L2 pathway, or with an agent that blocks the PD-1/PD-L1/PD-L2 pathway and at least one other antitumor agent (combination therapy).

49. A method of treating a tumor or cancer of a subject, comprising the method of embodiment 34.

50. A non-transitory computer-readable medium encoded with computer-executable instructions for performing the method of any one of embodiments 1 to 48.

51. A non-transitory computer-readable medium embodying at least one program that, when executed by a computing device comprising at least one processor, causes the computing device to perform the method of any one of embodiments 1 to 48.

52. The medium of embodiment 51, wherein the at least one program contains algorithms, instructions or codes for causing the at least one processor to perform the method of any one of embodiments 1 to 48.

53. A non-transitory computer-readable storage medium storing computer-readable algorithms, instructions or codes that, when executed by a computing device comprising at least one processor, cause or instruct the at least one processor to perform the method of any one of embodiments 1 to 48.

54. A method of treating a tumor or cancer of a patient, comprising:
  (1) administering to the patient an effective amount of an agent that blocks the PD-1/PD-L1/PD-L2 pathway and an effective amount of at least one other antitumor agent (combination therapy) if a pre-treatment (baseline) sample of an invasive tumor margin from the patient has a low cellular density of any one of CD8, PD-1, CD68 and PD-L1; or
  (2) administering to the patient an effective amount of a single agent that blocks the PD-1/PD-L1/PD-L2 pathway if a pre-treatment (baseline) sample of an invasive tumor margin from the patient does not have a low cellular density of each one of CD8, PD-1, CD68 and PD-L1.

55. The method of embodiment 54, wherein the combination therapy is provided if the pre-treatment sample of the invasive tumor margin has cellular densities of:
  (1) $CD8^{low}$, $PD\text{-}1^{low}$, $CD68^{low}$ and $PD\text{-}L1^{low}$; or
  (2) $CD8^{low}$, $PD\text{-}1^{low}$, $CD68^{low}$ and $PD\text{-}L1^{high}$; or
  (3) $CD8^{low}$, $PD\text{-}1^{low}$, $CD68^{high}$ and $PD\text{-}L1^{high}$; or
  (4) $CD8^{moderate}$, $PD\text{-}1^{moderate}$, $CD68^{low}$ and $PD\text{-}L1^{low}$; or
  (5) $CD8^{moderate}$, $PD\text{-}1^{moderate}$, $CD68^{low}$ and $PD\text{-}L1^{high}$; or
  (6) $CD8^{high}$, $PD\text{-}1^{high}$, $CD68^{low}$ and $PD\text{-}L1^{low}$.

56. The method of embodiment 54 or 55, wherein the combination therapy is provided if the pre-treatment sample of the invasive tumor margin has cellular densities of:
  (1) $PD\text{-}1^{low}$ and $PD\text{-}L1^{low}$; or
  (2) $PD\text{-}1^{moderate}$ and $PD\text{-}L1^{low}$; or
  (3) $PD\text{-}1^{low}$ and $PD\text{-}L1^{moderate}$; or
  (4) $PD\text{-}1^{low}$ and $PD\text{-}L1^{high}$; or
  (5) $CD8^{low}$ and $PD\text{-}L1^{low}$.

57. The method of any one of embodiments 54 to 56, wherein the combination therapy is provided if the pre-treatment sample of the invasive tumor margin shows multifocal PD-L1 expression.

58. The method of any one of embodiments 54 to 57, wherein the combination therapy is provided if the pre-treatment sample of the invasive tumor margin has a CD8 cellular density of no more than about 400 or 500 cells/mm$^2$.

59. The method of any one of embodiments 54 to 58, wherein the combination therapy is provided if the pre-treatment sample of the invasive tumor margin has a low cellular density of PD-L2.

60. The method of any one of embodiments 54 to 59, wherein the combination therapy is provided if the pre-treatment sample of the invasive tumor margin (e.g., an area of CD8$^+$ T cell infiltration) has a low expression level of pSTAT1 (phosphorylated Signal Transducer and Activator of Transcription 1).

61. The method of any one of embodiments 54 to 60, wherein the combination therapy is provided if the pre-treatment sample of the invasive tumor margin has a low expression level of granzyme B.

62. The method of any one of embodiments 54 to 61, wherein the combination therapy is provided if the pre-treatment sample of the invasive tumor margin does not show a close proximity between PD-1 and PD-L1.

63. The method of any one of embodiments 54 to 62, wherein the combination therapy is provided if the pre-treatment sample of the invasive tumor margin shows a more diverse T cell antigen receptor (TCR) repertoire.

64. The method of embodiment 54, wherein only an agent that blocks the PD-1/PD-L1/PD-L2 pathway is administered if the pre-treatment sample of the invasive tumor margin:
   (1) has high cellular densities of CD8 and PD-L1; or
   (2) does not have a low expression level of pSTAT1 and/or granzyme B; or
   (3) shows a close proximity between PD-1 and PD-L1; or
   (4) shows a more clonal TCR repertoire; or
   (5) any combination, or all, of (1) to (4).

65. The method of any one of embodiments 54 to 64, wherein the CD8 and PD-1 are expressed on the surface of T cells (e.g., cytotoxic and regulatory T cells), the CD68 and PD-L1 are expressed on the surface of myeloid-derived cells (MDCs) (e.g., macrophages and dendritic cells), and the PD-L1 is expressed on the surface of tumor cells, at the invasive tumor margin.

66. The method of embodiment 65, wherein the MDCs expressing PD-L1 also express CD11b.

67. The method of any one of embodiments 54 to 66, wherein PD-L2 is expressed on the surface of MDCs (e.g., macrophages and dendritic cells) and possibly tumor cells.

68. The method of any one of embodiments 54 to 67, wherein the agent that blocks the PD-1/PD-L1/PD-L2 pathway is selected from the group consisting of anti-PD-1 antibodies (e.g., nivolumab [BMS-936558, MDX-1106 or ONO-4538], pembrolizumab [lambrolizumab or MK-3475], pidilizumab [CT-011] and MEDI-0680 [AMP-514]), anti-PD-1 fusion proteins (e.g., AMP-224 [containing an Fc antibody domain and PD-L2]), anti-PD-L1 antibodies (e.g., BMS-936559 [MDX-1105], MEDI-4736, MPDL3280A [RG7446] and MSB0010718C), and analogs, derivatives, fragments and salts thereof.

69. The method of embodiment 68, wherein the agent that blocks the PD-1/PD-L1/PD-L2 pathway is an anti-PD-1 agent (e.g., an anti-PD-1 antibody, such as nivolumab or pembrolizumab).

70. The method of any one of embodiments 54 to 69, wherein the at least one other antitumor agent is selected from the group consisting of cytotoxic agents, immune system stimulators, other immune checkpoint inhibitors, angiogenesis inhibitors, targeted antitumor therapeutics (including immunotherapeutics), and other kinds of antitumor agents (including cancer vaccines).

71. The method of embodiment 70, wherein the at least one other antitumor agent comprises another immune checkpoint inhibitor (e.g., a CTLA-4 inhibitor, such as ipilimumab) and/or an immune system stimulator (e.g., a TLR9 agonist, such as agatolimod).

72. The method of any one of embodiments 54 to 71, wherein the tumor or cancer is a solid tumor or a hematological malignancy.

73. The method of any one of embodiments 54 to 72, wherein the tumor or cancer is a tumor or cancer of the brain (e.g., glioma or glioblastoma), head or neck (e.g, mouth, throat or thyroid), gastrointestinal tract (e.g., esophagus, stomach, small or large intestine, colon or rectum), lung (e.g., small cell lung cancer [SCLC] or non-small cell lung cancer [NSCLC], such as squamous NSCLC or non-squamous NSCLC), pancreas, liver, kidney (e.g., renal cell cancer), bladder, breast (e.g., triple-negative breast cancer), uterus, cervix, ovary, prostate (e.g., castration-resistant prostate cancer), testicle, skin (e.g., melanoma, such as metastatic melanoma), epithelial tissue or cells (e.g., gastric carcinoma, colorectal carcinoma, hepatocellular carcinoma, renal cell carcinoma, urothelial bladder cancer, endometrial cancer, or squamous cell carcinoma [e.g., of the head or neck]), or hematopoietic or lymphoid tissue or cells (e.g., leukemia [e.g., acute myeloid leukemia or chronic lymphocytic leukemia], lymphoma [e.g., Hodgkin's lymphoma or non-Hodgkin's lymphoma], myeloma [e.g., multiple myeloma], or myelodysplastic syndrome).

74. The method of any one of embodiments 54 to 73, wherein the patient may or may not have been previously administered an antitumor agent.

75. The method of any one of embodiments 54 to 74, further comprising discontinuing administration of the at least one other antitumor agent and continuing administration of the agent that blocks the PD-1/PD-L1/PD-L2 pathway if the patient is initially provided combination therapy, and if a sample of the invasive tumor margin and/or tumor parenchyma from the patient during treatment with the combination therapy does not have a low cellular density of each one of CD8, PD-1, CD68 and PD-L1 and shows:
   (1) increased cellular density of each of CD8, PD-1, CD68 and PD-L1 compared to baseline; or
   (2) proliferation of CD8 T cells at the invasive tumor margin and/or in the tumor parenchyma (e.g., an increased number of CD8/Ki67 double-positive cells at least in the tumor parenchyma compared to baseline); or
   (3) accumulation of tumor-antigen specific T cells at least in the tumor parenchyma (e.g., a more clonal TCR repertoire at least in the tumor parenchyma compared to baseline); or
   (4) increased expression of pSTAT1 at least at the invasive tumor margin (e.g., an area of CD8+ T cell infiltration) and/or increased expression of granzyme B compared to baseline; or
   (5) a close proximity between PD-1 and PD-L1; or
   (6) any combination, or all, of (1) to (5).

76. The method of any one of embodiments 54 to 74, further comprising administering an effective amount of at least one other antitumor agent if the patient is initially administered only an agent that blocks the PD-1/PD-L1/PD-L2 pathway and does not respond to such treatment.

77. A method of identifying a patient as a responder to anti-PD-1 or anti-PD-L1 therapy, the method comprising:
   (a) contacting a sample from the patient with an assay reagent that detects PD-L1+ or PD-L2+ myeloid-derived cells (MDCs); and
   (b) assaying for the presence of PD-L1+ or PD-L2+ MDCs in the patient sample;
   wherein the presence of PD-L1+ or PD-L2+ MDCs is indicative of a responder to anti-PD-1 or PD-L1 blocking therapy.

78. A method of detecting cancer in a subject, the method comprising:
   (a) contacting a sample from the patient with an assay reagent that detects PD-L1+ or PD-L2+ myeloid-derived cells (MDCs); and
   (b) assaying for the presence of PD-L1+ or PD-L2+ MDCs in the patient sample;
   wherein the presence of PD-L1+ or PD-L2+ MDCs is indicative of cancer.

79. A method of determining efficacy of anti-PD-1 or anti-PD-L1 therapy in a patient, the method comprising:
(a) contacting a sample from the patient with an assay reagent that detects PD-L1+ or PD-L2+ myeloid-derived cells (MDCs); and
(b) assaying for the presence of PD-L1+ or PD-L2+ MDCs in the patient sample;
wherein the presence of PD-L1+ or PD-L2+ MDCs is indicative of a responder to anti-PD-1 or PD-L1 blocking therapy.

80. The method of embodiment 79, wherein the assaying is repeated after administration of anti-PD-1 or anti-PD-L1 therapy to the patient, and wherein an increase in the presence of PD-L1+ or PD-L2+ MDCs in the patient sample relative to the previously assayed sample is indicative of effective anti-PD-1 or anti-PD-L1 therapy.

81. The method of any one of embodiments 77 to 79, wherein the sample is a cell-containing sample, or a fluid-containing sample.

82. The method of any one of embodiments 77 to 79, wherein the sample comprises extracellular, cell dissociated, and/or cell-derived products.

83. The method of any one of embodiments 77 to 79, wherein the PD-L1+ MDCs have a phenotype selected from the group consisting of: PD-L1+CD11b+; PD-L1+CD11c+; PD-L1+CD14+; PD-L1+CD33+; PD-L1+CD38+; PD-L1+CD34+; PD-L1+CD36/SR-b3+; PD-L1+CD59+; PD-L1+CD68+; PD-L1+CD163+; PD-L1+CD164+; PD-L1+HAM-56+; PD-L1+CD66a+; PD-L1+CD66b+; PD-L1+CD66c+; PD-L1+CD66d+; PD-L1+CD68/SR-D1+; PD-L1+CD42b/GPIb alpha+; PD-L1+CDCXCR3+; and PD-L1+F4/80/EMR1+.

84. The method of any one of embodiments 77 to 79, wherein the PD-L2+ MDCs have a phenotype selected from the group consisting of: PD-L2$^+$CD11b$^+$; PD-L2$^+$CD11c$^+$; PD-L2$^+$CD24$^+$; PD-L2$^+$CD33$^+$; PD-L2$^+$CD38$^+$; PD-L2$^+$CD34$^+$; PD-L2$^+$CD36/SR-b3$^+$; PD-L2$^+$CD59$^+$; PD-L2$^+$CD68$^+$; PD-L2$^+$CD163$^+$; PD-L2$^+$CD164$^+$; PD-L2$^+$HAM-56$^+$; PD-L2$^+$CD66a$^+$; PD-L2$^+$CD66b$^+$; PD-L2$^+$CD66c$^+$; PD-L2$^+$CD66d$^+$; PD-L2$^+$CD68/SR-D2$^+$; PD-L2$^+$CD42b/GPIb alpha$^+$; PD-L2$^+$CDCXCR3$^+$; and PD-L2$^+$F4/80/EMR2$^+$.

85. The method of any one of embodiments 77 to 79, wherein the assay reagent comprises an antibody that specifically binds PD-L1+ and an antibody that specifically binds CD11b+; CD11c+; CD14+; CD33+; CD38+; CD34+; CD36/SR-b3+; CD59+; CD68+; CD163+; CD164+; HAM-56+; CD66a+; CD66b+; CD66c+; CD66d+; CD68/SR-D1+; CD42b/GPIb alpha+; CDCXCR3+; or F4/80/EMR1+.

86. The method of any one of embodiments 77 to 79, wherein the assay reagent comprises an antibody that specifically binds PD-L2+ and an antibody that specifically binds CD11b$^+$; CD11c$^+$; CD24$^+$; CD33$^+$; CD38$^+$; CD34$^+$; CD36/SR-b3$^+$; CD59$^+$; CD68$^+$; CD163$^+$; CD164$^+$; HAM-56$^+$; CD66a$^+$; CD66b$^+$; CD66c$^+$; CD66d$^+$; CD68/SR-D2$^+$; CD42b/GPIb alpha$^+$; CDCXCR3$^+$; or F4/80/EMR2$^+$.

87. The method of any one of embodiments 77 to 79, wherein the assaying comprises performing an immunoassay.

88. The method of embodiment 87, wherein the immunoassay comprises immunohistochemistry.

89. The method of any one of embodiments 77 to 79, wherein the assay comprises polymerase chain reaction.

90. The method of any one of embodiments 77 to 79, wherein the assaying comprises analysis of MDC phenotype.

91. The method of any one of embodiments 77 to 79, wherein the sample comprises tissue and/or peripheral blood.

92. The method of any one of embodiments 77 to 79, wherein the sample is a tumor sample.

93. The method of embodiment 92, wherein the tumor sample comprises an invasive tumor margin and/or tumor parenchyma.

94. The method of embodiment 92, wherein the tumor sample is obtained from a metastatic lesion.

95. The method of any one of embodiments 77 to 79, wherein the patient is suspected of having a metastatic cancer.

96. The method of embodiment 77, further comprising treating the patient with anti-PD-1 therapy if identified as a responder, and with combination therapy if not identified as a responder.

97. A method of treating cancer in a patient, the method comprising:
(a) identifying the patient as a responder to anti-PD-1 or anti-PD-L1 therapy in accordance with the method of embodiment 77; and
(b) treating the patient with anti-PD-1 therapy if identified as a responder, and with combination therapy if not identified as a responder.

EXAMPLES

The following examples are presented to illustrate the present invention and to assist one of ordinary skill in making and using the same. The examples are not intended in any way to otherwise limit the scope of the invention.

Example 1

Baseline CD8+ T Cell Organization within Tumor Predicts Anti-PD-1 Response

Figure 3:
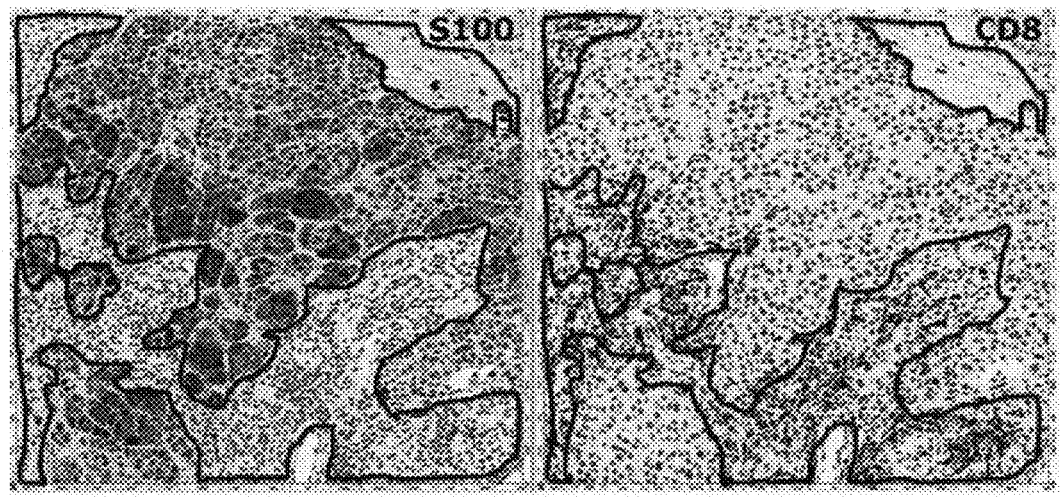
FIG. 3 is a pair of digital photomicrographs of serial sections of tumor biopsies stained for S100 (left panel) and CD8 (right panel). Lines indicate borders between peritumoral and intratumoral areas.

Histological sections were analyzed to reveal the distinct baseline CD8+ T cell organization within the tumor microenvironment of metastatic lesions that is found in patients who go on to respond to anti-PD-1 therapy. Quantification of baseline CD8+ T cell organization was found to predict response to therapy on IHC and CT scan. T cell organization was determined by microanatomic mapping and analyzing prevalence, distribution, and phenotype within the tumor microenvironment. FIG. 3 shows how CD8+ T cell organization in histological sections can be assessed using algorithms that enable whole slide colocalization and microanatomic mapping of CD8+ T cell prevalence, distribution, and location within the tumor microenvironment. Serial histological sections of 2-3 μM thickness were stained with S100 (left panel) and CD8 (right panel), respectively. The X and Y axes were scaled in 10 μM increments, providing coordinates for side-by-side alignment of tissue sections and analysis of regions in the tumor. "PR" refers to partial responders, "PD" to progressive disease. Direct correlation was found between anti-tumor response to therapy and baseline CD8+ T cell location and density. Two biopsies were performed on distinct and separate tumors of the same patient on the same clinic visit date, and demonstrated comparable qualitative and quantitative CD8+ T cell organization within the tumor microenvironment, before and after treatment.

Figure 4A:
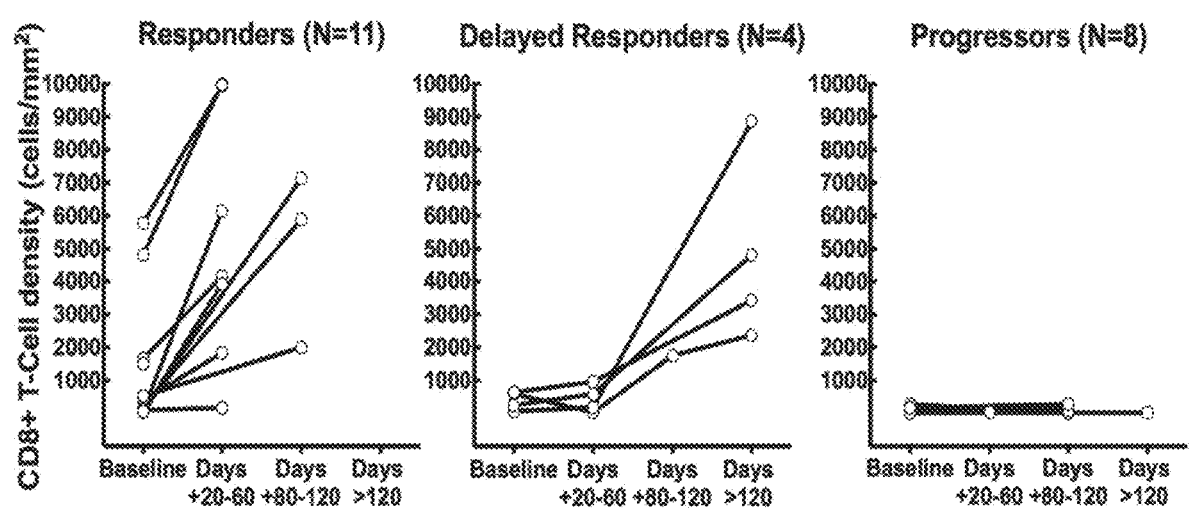
FIGS. 4A-4C are a series of graphs showing that quantification of baseline CD8+ T cell organization predicts response to therapy on IHC and CT scan.
Figure 4B:
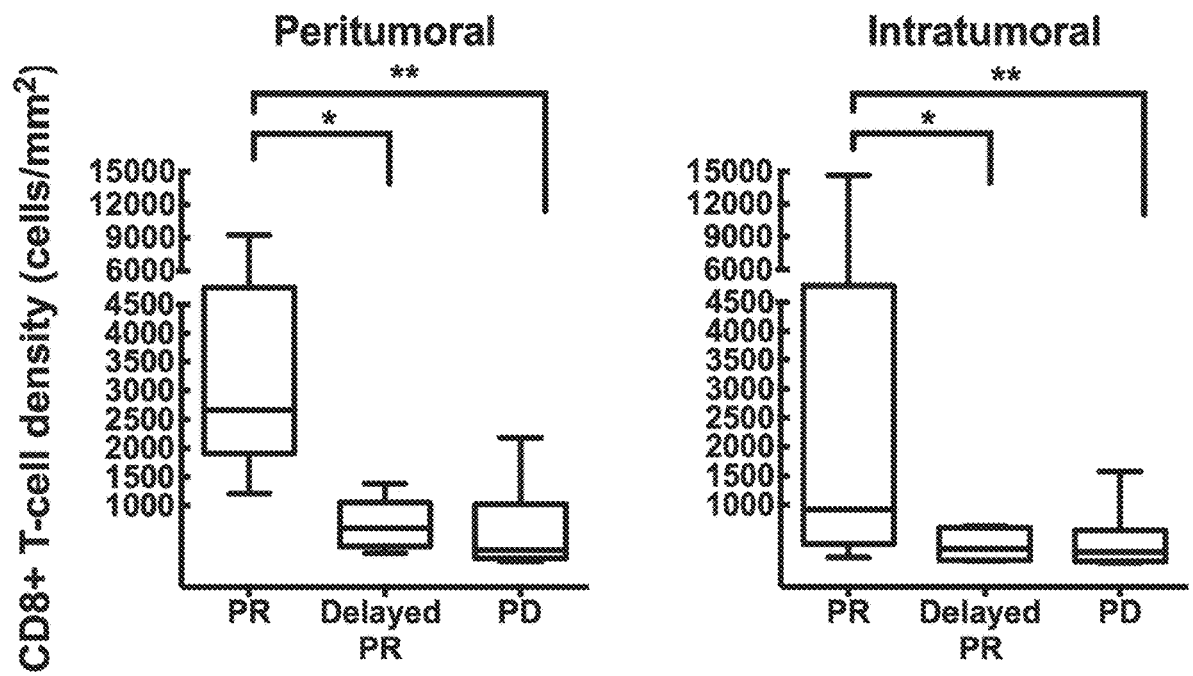
Figure 4C:
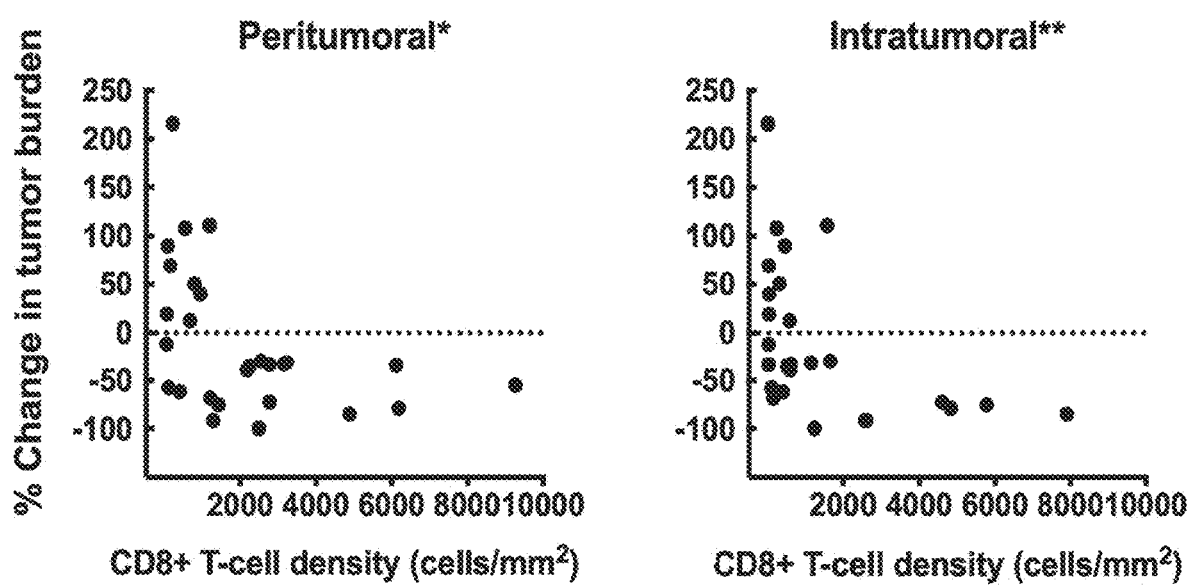

FIGS. 4A-4C illustrate quantification of baseline and treatment response/progression analyzed via immunohistochemistry and CT scan, and the relationship between these measures and response to therapy. The graphs in FIG. 4A show how CD8+ T cell density trends within the tumor microenvironment at baseline and over the course of treatment for responders (left panel), delayed responders (center) and progressors (right panel). Both peritumoral and intratumoral environments showed significant differences in T cell density between groups, as shown in FIGS. 4B and 4C. The difference in CD8+ T cell organization in the tumor microenvironment was comparable for both naïve and previously treated responders.

Figure 5:
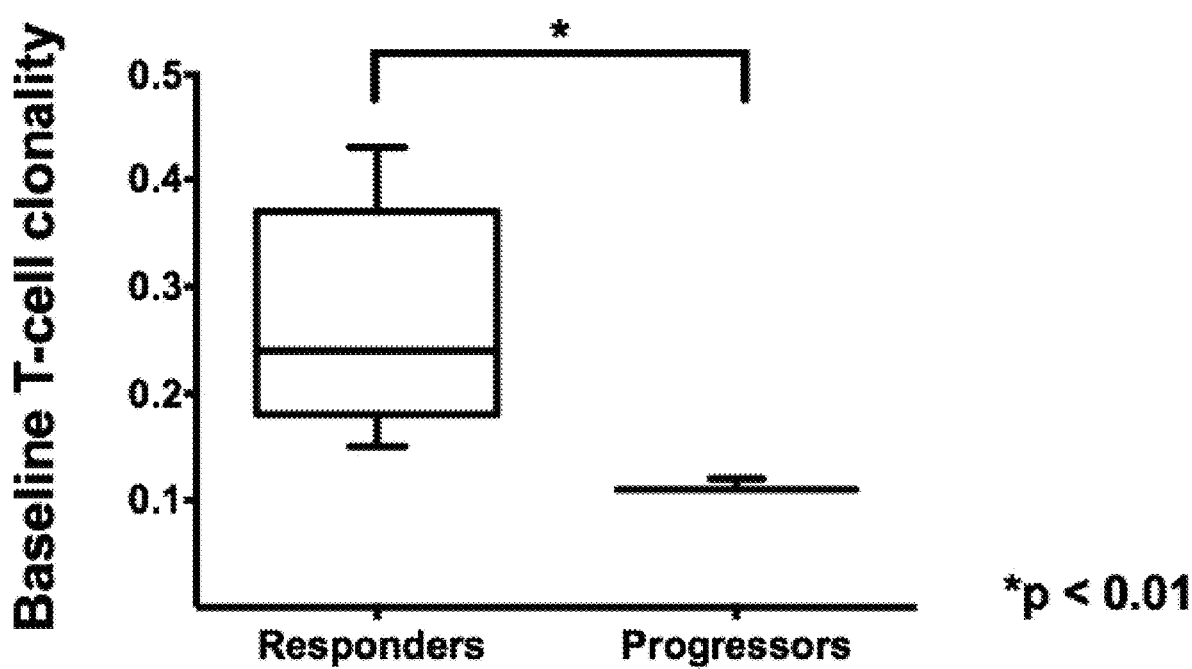
FIG. 5 shows the higher T cell clonality observed at baseline for responders versus progressors.

Analysis of photomicrographs comparing before treatment (baseline) and on-treatment samples showed that the CD8+ T cells in tumors of responders are uniquely capable of late-effector phase end-organ T cell activation and replication. The results also showed that T-cell populations within tumors at baseline (before treatment) display higher clonality for those that go on to respond to therapy compared to those that go on to progress on therapy (p<0.01). See FIG. 5.

Example 2

Determining the Impact of PD1 Blocking Antibody on the PDL1+ Myeloid-Cell Transcription Program in Tumors that Respond to Anti-PD1

Figures 6A, 6B, 6C, 6D:
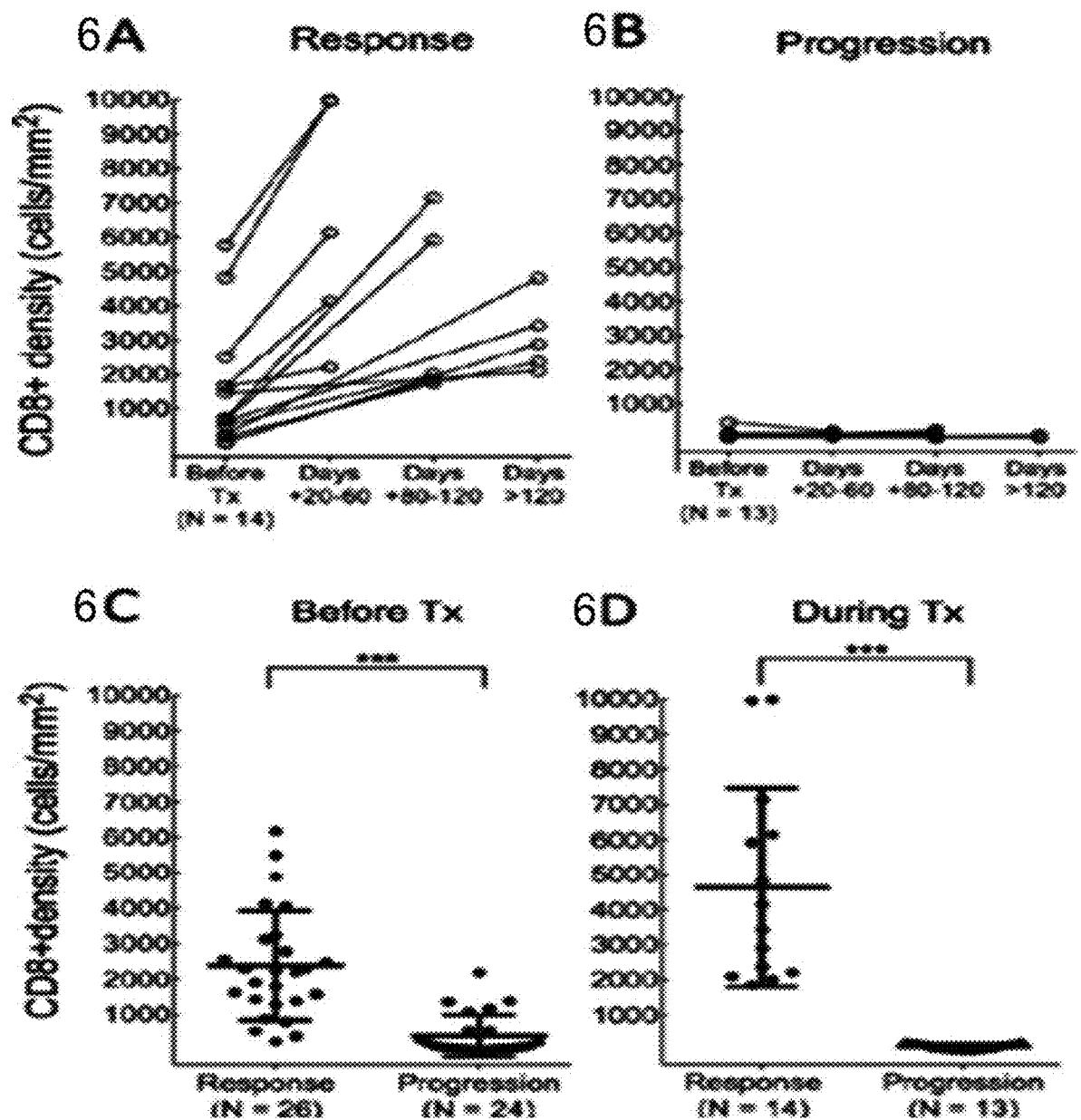
FIGS. 6A-6D are graphs depicting quantitative analysis of CD8+ T cells in tumor samples before and during anti-PD1 treatment. CD8+ T cell density was measured in serially biopsied matched tumors in the response (FIG. 6A; n=14) and progression (FIG. 6B; n=13) groups over time (baseline, 20-60 days, 8-120 days, >120 days). These measures for the response and progression groups were compared before treatment (FIG. 6C) and during treatment (FIG. 6D) with anti-PD1 therapy, with the response group showing a significantly higher CD8+ T cell density compared to the progression group; ***p<0.0001.

We analyzed 85 tumor samples obtained from 40 patients before and during pembrolizumab (MK-3475) (anti-PD1) treatment. Using quantitative immunohistochemistry (QIHC), we investigated CD8+ distribution as well as PD1 and PDL1 expression in terms of response (85 specimens; FIG. 6). In post-treatment samples, we found a significant correlation between CD8+ density and clinical response (p<0.001). In pre-treatment samples, the response group was associated with a significantly higher CD8+ density when compared to the progression group (p<0.0001). Further investigation showed CD8+ T-cells to express the majority of PD1 expression. Surprisingly, CD11 b+ MDCs represented a large percentage of the PDL1 expressing cells that was maintained in all tumor regressing samples. In patients with mixed responses, the density PDL1+ MDCs was high during regression and low during relapse.

Our findings suggest that PDL1+ MDCs are required to achieve durable tumor regression with anti-PD1 therapy. Additionally, in tumors that respond, PDL1+ MDCs likely undergo transcriptional and functional evolution that is characterized by an "anti-inflammatory" program and suppressive to T-cells (before PD1 blockade) that evolves into a "pro-inflammatory" program and stimulatory to T-cell (during PD1 blockade). To confirm this hypothesis, we have established an RNA-preserved, paraffin-embedded tumor bank that comprises of samples obtained from matched tumors before and during anti-PD1 therapy. One can use laser-capture microdissection (LCM) to enrich for MDCs, followed by targeted gene expression profiling using a human immune array panel. We have established the ability to extract RNA of high quality and yield from these samples. We hypothesize that PDL1+ MDCs will start with an "anti-inflammatory" signature before treatment and switch to a "pro-inflammatory" signature during anti-PD1 therapy. We can thus isolate PDL1+ MDCs from their native microenvironment and extract high quality RNA, and confirm that in responding tumors, PDL1+ MDCs undergo transcriptional re-programming that is characterized by an "anti-inflammatory" signature (before PD1) that switches to a "pro-inflammatory" signature (under PD1 blockade).

Figures 7A, 7B:
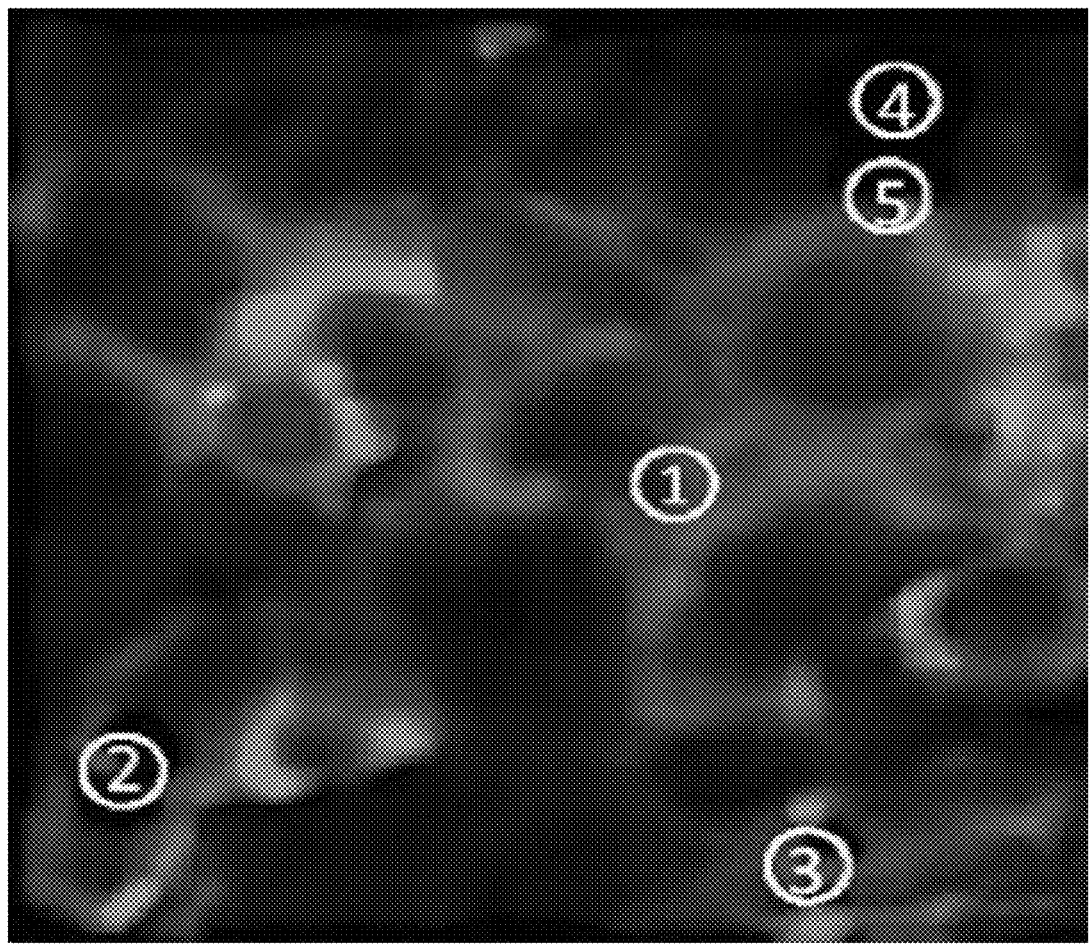
FIGS. 7A-7B illustrate the quantitative image analysis performed on double-fluorescent immuno-histochemistry stains to examine the spatial relationships between PD1+ and PDL1+ cells. 10,000 isolated regions of each slide were assessed for the presence of red and green pixels (one color for each stain). For example, when 5 regions of a slide are assessed (FIG. 7A), a total count of red and green pixels is quantified to generate a proximity call (FIG. 7B).

A tissue fixation system that preserves RNA and morphology—An innovative approach: To identify cellular mediators of tumor response, we established an approach that enables expression-level analysis of spatially-resolved RNA. Our preliminary data using formalin-free, alcohol-fixed paraffin embedded (AFPE) preservation protocol shows superior RNA preservation compared to formalin-fixed methods. We systematically obtained tumor samples and categorized them according to RECIST 1.1 criteria including: (1) Response: objective tumor size reductions of >30% (2) Progression: objective tumor size increases of >20% (3) Mixed: tumor size at 16 weeks showed a >30% reduction, but then reversed trajectory at a later time point and showed increase in size. Using FDA-approved, in-vitro diagnostic (IVD) antibodies QIHC with co-registration capabilities, we characterized the evolution of the following cell-types within the tumor microenvironment: lymphoid-derived: T-cells (CD8, CD4, FOXP3), B-cells (CD20), Natural-killer cells (CD56); myeloid-derived: (CD11b, CD163, CD68, CD14, CD15); melanoma: (S100, MART1, HMB-45). We applied a proximity assay involving quantitative image analysis algorithms on double-fluorescent immunohistochemistry stains for PD1 and PDL1 (FIG. 7). This assay allowed us to identify that PDL1+ MDCs exclusively interface with PD1+/CD8+ T-cells. In patients with objective responses, this relationship was invariably present before and during PD1 blockade, with both cell-types increasing in density and relative % prevalence over time. In patients that responded but later progressed, these spatially-defined MDCs lost expression of PDL1 (FIG. 8).

MDCs in tumors, defined by their expression of the lineage markers CD11b and/or CD33, represent the most prevalent immune cell in tumors. The hallmarks of MDCs comprise two biological capabilities: i) plasticity; that is, the ability to undergo functional changes in response to signals from the microenvironment, and ii) suppression of T-cell activity.[6,7] The finding that plasticity is a capability maintained among all MDC subtypes suggests this may be a common mechanism in regulating adaptive immunity. Among MDC interaction with other cell-types in tumors, mounting evidence shows that MDCs interface with adaptive lymphoid subsets and engage in complex bidirectional communication.[8]

To identify cell-types that are required to achieve durable tumor regression with anti-PD1 therapy, the transcriptional program of PDL1+ MDCs is investigated using our repository of formalin-free, molecular-content preserved, paraffin-embedded tumors obtained from patients enrolled in our MK-3475 (anti-PD1) Phase I clinical trial. We will show that PDL1+ MDCs are required to achieve tumor rejection with anti-PD1 therapy. Additionally, their phenotype and function evolve from "anti-inflammatory" with T-cell suppressive function (before PD1 blockade), to "pro-inflammatory" with T-cell stimulatory function (during PD1 blockade).

"Anti-inflammatory" MDCs are characterized by promoting tumor growth, expression of CD163, CD206, CCL18, CCL22, and E-cadherin, release of anti-inflammatory cytokines (IL-10 and IL1RA), upregulation of pro-angiogenic factors (IL-8, VEGF, EFG), and upregulation of Arg1, Ym1, Fizz1, and MGL. "Pro-inflammatory" MDCs are characterized by the ability to destroy tumors, higher expression levels of MHC class II and costimulatory molecules, efficient antigen presentation, release of pro-inflammatory cytokines (IL-23, IL-12, TNF, CXCL9, CXCL10), and reactive oxygen/nitrogen species. LCM is used to enrich for this cell-type, and quantitative real-time PCR (qRT-PCR) is used to perform targeted gene expression analysis using a human immune array panel.

To isolate RNA that is of high quality and yield to perform downstream targeted gene expression studies, we will use LCM to dissect out this population from our AFPE samples. Based on feasibility studies, we have established our ability to isolate RNA with quality and yields: RIN values: 6-8, A260/A280: >1.9, and A260/A230: >2.0, yields: 1.2-3.0 ng. Using LCM to isolate this spatially-defined cell-population, we reproducibly generate 1 picogram (pg) of RNA/cell. This translates to 1000 cells being required to achieve 1.0 ng of RNA; this is achievable based on QIHC, which generate density counts of 1000 PDL1+ cells/mm$^2$.

To date, MDCs that express PDL1 have not been identified outside of interfacing PD1+CD8+ T-cells (N=120 samples). In all experimental groups, only one spatially-defined MDC subpopulation will be isolated for gene expression studies: MDCs that interface with PD1+CD8+ T-cells. In the Response group (N=18), this MDC subpopulation invariably expresses PDL1. In both the Progressive and Mixed Response groups, this MDC subpopulation maintains co-localization with CD8+ T-cells, but varies in PDL1 expression: (i) PDL1+ MDC or (ii) PDL1− MDCs. The following groups will be included: Response group (a,b): (a) Pre-treatment: PDL1+ MDCs, (b) post-treatment: PDL1+ MDCs; the Progression group (c,d,e): (c) Pre-treatment: PDL1+ MDCs, (d) Post-treatment: PDL1+ MDCs, (e) Post-treatment: PDL1 negative MDCs that interface with PD1+CD8+ T-cells; and the Mixed Response Group (f, g, h, i): (f) Pre-treatment: PDL1+ MDCs, (g) Post-treatment during tumor regression: PDL1+ MDCs, (h) Post-treatment during tumor relapse and progression: PDL1+ MDCs, (i) Post-treatment during tumor relapse and progression: PDL1 negative MDCs that interface with PD1+CD8+ T-cells. Using qRT-PCR, we will examine a previously established cohort of genes that represent distinct MDC transcription programs (anti vs. pro-inflammatory), that encode for cytokines, chemokines, chemokine receptors, inflammatory mediators, and costimulatory molecules.[9] A threshold of ≥2-fold will be set to determine genes that have been upregulated. We will isolate RNA enriched for PDL1+ MDCs that meet the following criteria: RIN values >6, A260/A280 ratio >1.9, 260/230 ratio >2 and yield: >1 ng. Based on our LCM feasibility studies, 1000 cells translate to approximately a 1×10$^5$ um$^2$ area of tissue. Each sample was harvested from tumors using an 8 mm punch biopsy or greater, providing for at least 10×10$^6$ um$^2$ of tissue area for dissection, well over the required area amount. We will also generate transcriptional signatures of PDL1+ MDCs. RT-q-PCR is highly sensitive to sample degradation. If the RIN values on average are <5, we will perform nanostring, a multiplexing primer-based technology shown to have superior performance on samples with compromised RNA.[10] Each tumor sample at the time of harvest was transected and fixed with flash freezing, RNALater, and formalin. If unanticipated challenges occur, we will perform LCM on FFPE samples followed by Nanostring.

References Cited in Example 2

1. Hamid O, et al. New England Journal of Medicine 2013; 369:134-44.
2. Topalian S L, et al. New England Journal of Medicine 2012; 366:2443-54.
3. Riley J L. New England Journal of Medicine 2013; 369:187-9.
4. Pardoll D M. Nature Reviews Cancer 2012; 12:252-64.
5. Galli S J, et al. Nature Immunology 2011; 12:1035-44.
6. Talmadge J E, Gabrilovich D I. Nature Reviews Cancer 2013; 13:739-52.
7. Condamine T, Gabrilovich D I. Trends in Immunology 2011; 32:19-25.
8. Biswas S K, Mantovani A. Nature Immunology 2010; 11:889-96.
9. Kerkar S P, et al. Journal of Clinical Investigation 2011; 121:4746-57.
10. Geiss G K, et al. Nat Biotechnol 2008; 26:317-25.
11. Lechner M G, et al. Journal of Translational Medicine 2011; 9.

Example 3

Phenotype Profiling in Anti-PD1 Treatment Failures

This example describes the method for stratifying non-responders, as validated on the protein level in clinical samples of non-responders in 32 patients from pre-treatment biopsies prior to receiving anti-PD1 therapy. The presence of four components was found to be correlated with response to anti-PD1 therapy: CD8+ T cells, CD8+ T cells expressing PD-1 inhibitory receptor, CD68+ macrophages, and CD68+ macrophages expressing PD-L1 inhibitory ligand. One type of non-responder is CD8low-PD1low-CD68low-PDL1low at the invasive tumor margin; another is CD8high-PD1high-CD68low-PDL1low at the invasive tumor margin; another is CD8low-PD1low-CD68low-PDL1 high at the invasive margin; and another is CD8low-PD1low-CD68high-PDL1 high at the invasive margin.

Example 4

PD-1 Blockade Induces Responses by Inhibiting Adaptive Immune Resistance

This example shows that pre-existing CD8 T-cells distinctly located at the invasive tumour margin are associated with expression of the PD-1/PD-L1 immune inhibitory axis and predict response to therapy. We analyzed samples from 46 patients with metastatic melanoma obtained before and during anti-PD1 therapy (pembrolizumab) using quantitative immunohistochemistry, quantitative multiplex immunofluorescence, and next generation sequencing for T-cell receptors (TCR). In serially sampled tumours, responding patients showed proliferation of intratumoural CD8+ T-cells that directly correlated with radiographic reduction in tumour size. Pre-treatment samples obtained from responding patients showed higher numbers of CD8, PD1, and PD-L1 expressing cells at the invasive tumour margin and inside tumours, with close proximity between PD-1 and PD-L1, and a more clonal TCR repertoire. Using multivariate analysis, we established a predictive model based on CD8 expression at the invasive margin and validated the model in an independent cohort of 15 patients. Our findings indicate that tumour regression following therapeutic PD-1 blockade requires pre-existing CD8+ T cells that are negatively regulated by PD-1/PD-L1 mediated adaptive immune resistance.

This example builds upon the evidence that response rates to PD-1 or PD-L1 blocking antibodies are higher in patients whose tumours express PD-L1.[1,15] Since PD-L1 can be either constitutively expressed or induced upon T cell recognition and production of interferons,[11,15] we hypothesized that response to PD-1 blockade would more tightly covariate with the inducible PD-L1 expression in the presence of antigen-specific T cells,[7] termed adaptive immune resistance.[6] Indeed, we found interfacing PD-L1 expressing cells in tumours and PD-1 positive T-cells in pre-treatment samples of responders. Our data suggests that PD-L1 serves as an indirect marker of adaptive immune resistance in response to tumour antigen-specific T cell infiltration rather than a static constitutive biomarker. Hence, inducing a type-I interferon inflammatory response in combination with PD-L1 blockade merits further clinical investigation.[11]

T cell infiltrates have been found to have predictive value with respect to the natural history of primary cancers.[13,14,18] We report that the baseline density and location of T cells in metastatic melanomas have predictive value in the treatment outcome of patients receiving therapies that block the PD-1/PD-L1 axis. Releasing the PD-1 immune checkpoint results in clinically relevant antitumour activity when there is a greater density of pre-existing tumour antigen-restricted CD8 T cells that are negatively regulated by PD-1/PD-L1 interactions.

Tumour biopsies were obtained from a subset of patients enrolled in a phase 1a clinical trial that enrolled 411 patients;[19] patients were selected for this analysis by having adequate tumour biopsy samples and clinical follow up. Slides were stained with hematoxylin and eosin, S100, CD8, CD4, Ki67, pSTAT1, and granzyme B at the UCLA Anatomic Pathology IHC laboratory. Immunostaining was performed on Leica Bond III autostainers using Leica Bond ancillary reagents and REFINE polymer DAB detection system. $CD8^+$ expression was determined using two read-outs that were independent of each other to account for tumour heterogeneity: cell density (number of positive cells/$mm^2$) and percent cellularity (number of positive cells/number of nucleated cells). Cell density and percent cellularity correlated significantly ($R^2=0.89$ in tumour and 0.84 in the invasive margin). Antibodies used included rabbit polyclonal S100 (DAKO, 1/1500 dilution, low pH retrieval), CD8 clone C8/144B (DAKO, 1/100, low pH retrieval), and rabbit monoclonal Ki67 clone EP5 (Epitomics, 1/50 dilution, high pH retrieval). For digital image acquisition and analysis, an algorithm was designed based on pattern recognition that quantified immune cells within S100 positive areas (tumour) and S100 negative areas (invasive margin). Image analysis based on RGB (red, green, blue) spectra was used to detect all cells by counterstaining with hemotoxylin (blue), and DAB or fast red. Demographic, clinical, and immunohistochemical variables were compared between responders and progressors using Kruskal-Wallis tests for ordinal or quantitative variables and Fisher's exact test for categorical variables. Logistic regression models for response vs. progression were constructed to assess the prognostic ability of CD8 and CD4 for both tumour and invasive margin measures. To determine the generalizability of the model to external samples, the coefficient estimates from our model were used to calculate predicted probabilities of progression in the Gustave Roussy validation cohort. Analyses were performed using GraphPad Prism, SAS, and SPSS. All tests were 2-sided and equal variance was not assumed unless otherwise stated. P-values <0.05 were considered statistically significant.

Tumour Samples

All patients in the study and validation cohorts underwent mandatory biopsy of a metastatic tumour within 30 days of starting treatment and one or more optional biopsies at 20-60 days, 60-120 days, or greater than 120 days after starting aPD-1. Samples were immediately fixed in formalin followed by paraffin embedding. Biopsy collection and analyses were approved by UCLA IRBs 11-001918 and 11-003066. Tumour samples obtained from the initial cohort of 46 patients from UCLA were analyzed for immunohistochemical analysis of CD8 (n=46 patients, 45 samples before and 31 samples during treatment) and CD4 (n=37 patients, 37 samples before and 0 samples during treatment), multiplex chromogenic staining (n=13 patients, 12 samples before and 17 samples during treatment). The validation cohort included baseline biopsies of 15 patients from Gustave Roussy.

Treatment Outcome Groups

Patients at both sites received single agent pembrolizumab intravenously in one of three dosing regimens: 2 mg/kg every 3 weeks (2Q3W), 10 mg/kg every 3 weeks (10Q3W), or 10 mg/kg every 2 weeks (10Q2W) within a phase 1 clinical trial that enrolled a total of 411 patients.[19] Tumour responses to pembrolizumab were evaluated at 12 and 16 weeks after the first infusion, and every 12 weeks thereafter. Treatment outcomes were statistically identical between the three dosing regimens. The Response Evaluation Criteria in Solid Tumours (RECIST) version 1.1 was used to define objective clinical responses by an independent, central, blinded radiographic review. The protocol allowed to proceed beyond initial progression at the restaging scans at 3 months and have repeated imaging scans 4 weeks later following the immune-related response criteria (irRC).[20] Following this protocol-specified criteria, two patients had evidence of increase in size of target lesions at 12 weeks, but met criteria for objective partial response at 36 weeks and were considered within the Response group but denoted as having a delayed response.

Immunohistochemical (IHC) Staining

Slides were stained with hematoxylin and eosin, S100, CD8. CD4, CD80, Ki67, pSTAT1, and granzyme B at the UCLA Anatomic Pathology IHC Laboratory. Immunostaining was performed on Leica Bond III autostainers using Leica Bond ancillary reagents and REFINE polymer DAB detection system. Antibodies used included rabbit polyclonal S100 (DAKO, 1/1500 dilution, low pH retrieval), CD8 clone C8/144B (DAKO, 1/100, low pH retrieval), rabbit monoclonal pSTAT1 clone D3B7 (Cell Signaling, 1/300 30 min, low pH retrieval). All stained slides were evaluated in a blinded fashion by one dermatopathologist and one investigator trained to identify the features of melanoma. Slides were examined for the presence of CD8, CD4, Ki67, granzyme B, and pSTAT1 within the tumour parenchyma (tumour) and the connective tissue surrounding the tumour (invasive margin).

Digital Image Acquisition and Analysis

All slides were scanned at an absolute magnification of 200× (resolution of 0.5 μm/pixel). An algorithm was designed based on pattern recognition that quantified immune cells within S100 positive areas (tumour) and S100 negative areas (invasive margin). Image analysis based on RGB (red, green, blue) spectra was used to detect all cells by counterstaining with hemotoxylin (blue), and DAB or fast red. The algorithm calculated the density (cells/mm2) and % cellularity (% positive cells/all nucleated cells) using Indica Labs Halo platform.

Statistical Analysis

Demographic, clinical, and immunohistochemical variables were compared between responders and progressors using Wilcoxon rank sum tests for ordinal or quantitative variables and Fisher's exact test for categorical variables. Receiver operating characteristic (ROC) curves for response vs. progression were constructed to assess the proprognostic ability of CD8 and CD4 for both tumour and invasive margin measures. The area under the ROC curve (AUC) was used to measure model performance and the Wilcoxon test was used to assess significance of the AUC results. A logistic regression model was constructed using pre-treatment CD 8+ (cells/mm$^2$) versus the outcome of clinical response (Response and Progression) using the study cohort. This fixed model was then applied to the CD 8+ density measurements in the Gustave Roussy validation cohort to compute predicted probabilities of response to treatment. Sensitivity and specificities were calculated. All tests were 2-sided and equal variance was not assumed unless otherwise stated. P-values <0.05 were considered statistically significant.

Figures 9A, 9B, 9C, 9D:
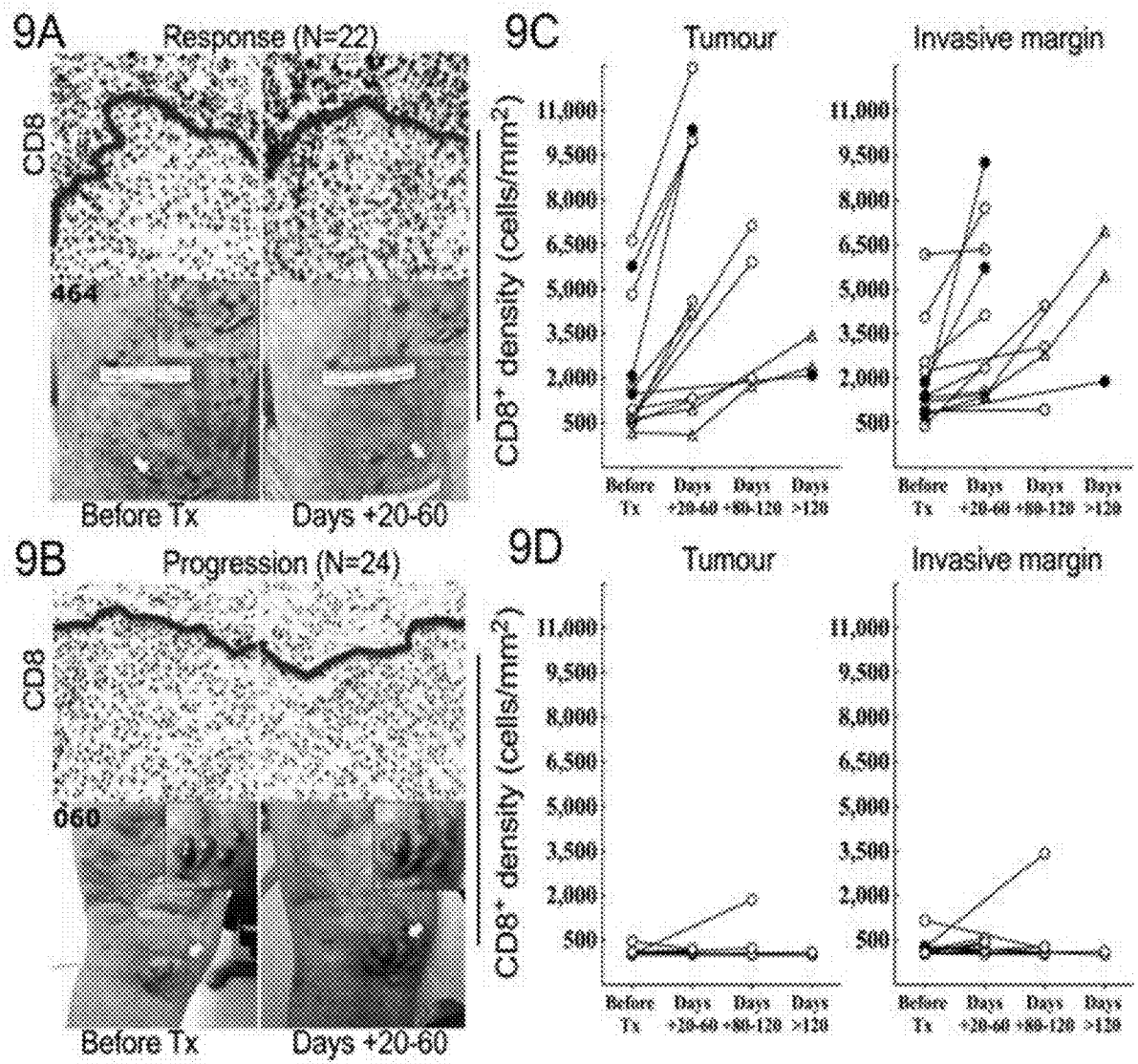
FIGS. 9A-9D illustrate immunohistochemical analysis of CD8$^+$ T cells in samples obtained before and during pembrolizumab treatment.

FIGS. 9A-9D illustrate immunohistochemical analysis of CD8$^+$ T cells in samples obtained before and during pembrolizumab treatment. FIGS. 9A and 9B, are digital photomicrographs showing examples of CD8 expression in melanoma tumours serially biopsied before PD-1 blocking treatment (Tx; left column of images) and 20-60 days after treatment began (Days$^+$20-60; right column of images) from a patient in the Response (FIG. 9A) and Progression (FIG. 9B) groups. Thick line separates tumour parenchyma (below line) and invasive margin (above line). Magnification, ×20. FIGS. 9C and 9D plot CD8$^+$ cell density at the tumour center (left panel) and invasive margin (right panel) in samples from all Responders (FIG. 9C, n=13) and Progressors (FIG. 9D, n=12) who received a biopsy before and during treatment. •=complete response, ○=partial response, Δ=delayed response.

FIGS. 10A-10B are digital photomicrographs showing that regressing tumours during treatment are associated with proliferating CD8T cells that localize to the tumour. FIG. 10A, Representative example of CD8/Ki67 chromogenic double staining from a sample obtained during tumour regression shows double positive CD8 cells localized to the tumour parenchyma. The thick line separates the invasive margin (above line) and tumour (below line). FIG. 10B, Top: Representative single positive quiescent CD8+ cells (no Ki-67 labeling in nucleus) from the invasive margin. Bottom: Representative double positive cells (labeled Ki67 nucleus, CD8 labeled membrane) with characteristic chromatin patterns associated with subphases of mitosis. Magnification, ×40.

FIG. 11 is a set of plots showing baseline density and location of CD8$^+$ and CD4$^+$ cells, according to treatment outcome. Melanoma samples collected before treatment with PD-1 blocking therapy were assessed for CD8 (Response n=22, Progression n=24) and CD4 (Response n=19, Progression n=18) density by quantitative immunohistochemistry in the tumour compartment and at the invasive margin. P<0.01, *P<0.001, ****P<0.0001.

Figure 12:
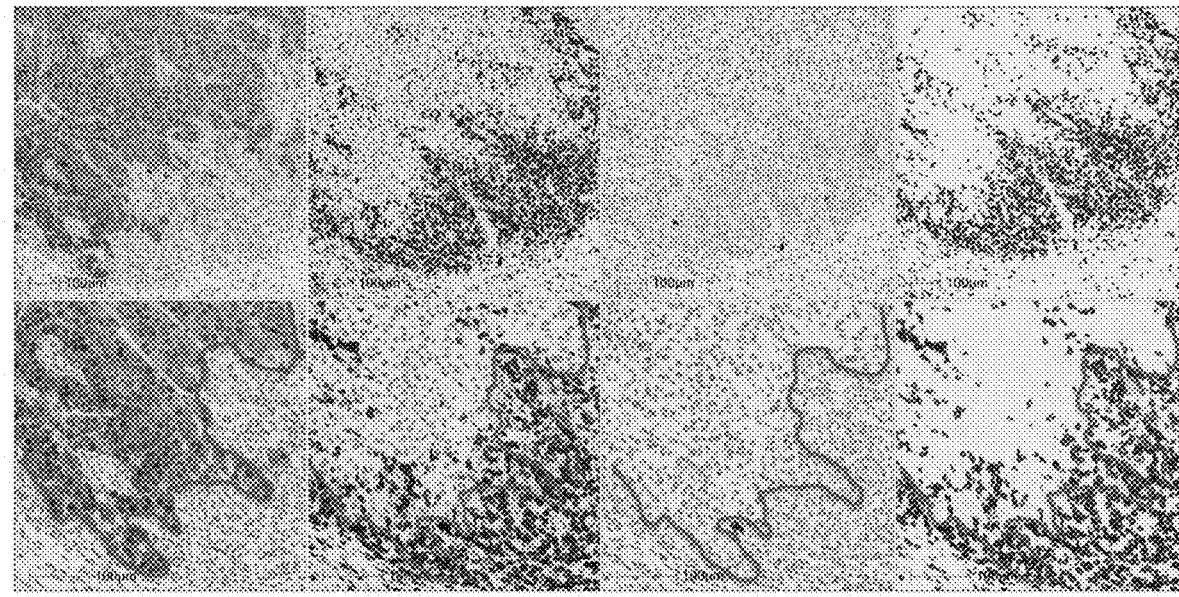
FIG. 12 is a series of digital photomicrographs showing segmentation of the invasive margin and tumour parenchyma using S100 and CD8 chromogenic staining. Low magnification (top row) and high magnification (bottom row) are shown. The line illustrates S100$^+$ tumour (left of line) and S100$^-$ stroma (right of line). Coordinates of the invasive margin and tumour parenchyma are generated from the S100 stained image (1$^{st}$ column) and subsequently imported into the CD8 stained image (2$^{nd}$ column). This is followed by a deconvolution imaging algorithm of the CD8 stained image where first, all nuclei (3$^{rd}$ column) are identified and quantified, irrespective of what type of cell. This is followed by identifying CD8+ membrane (4$^{th}$ column) for cell quantification and analysis.

FIG. 12 is a series of digital photomicrographs showing segmentation of the invasive margin and tumour parenchyma using S100 and CD8 chromogenic staining. Low magnification (top row) and high magnification (bottom row) are shown. The line illustrates S100$^+$ tumour (left of line) and S100$^-$ stroma (right of line). Coordinates of the invasive margin and tumour parenchyma are generated from the S100 stained image (1$^{st}$ column) and subsequently imported into the CD8 stained image (2$^{nd}$ column). This is followed by a deconvolution imaging algorithm of the CD8 stained image where first, all nuclei (3$^{rd}$ column) are identified and quantified, irrespective of what type of cell. This is followed by identifying CD8+ membrane (4$^{th}$ column) for cell quantification and analysis.

Figure 13:
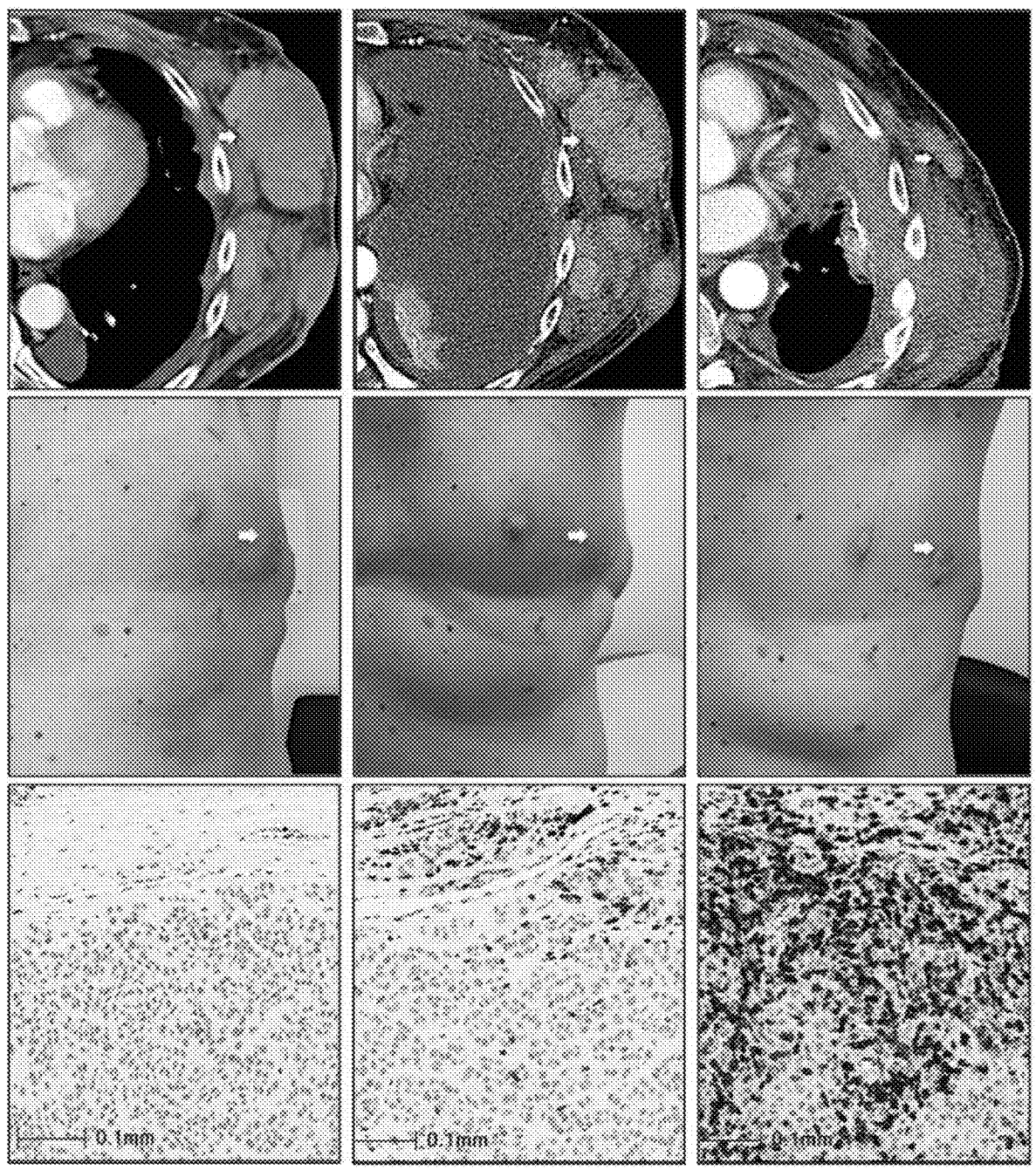
FIG. 13 is a series of digital images illustrating CD8+ T-cell kinetics within the tumour microenvironment in a serially sampled tumour responding to PD-1 blocking therapy. Example of radiographic, clinical, and CD8 IHC in a serially sampled melanoma tumour of the left chest wall that was obtained from a patient with a delayed response. On day +20, clinical and radiographic examinations indicated progressive disease; at a time when CD8 T-cells expression increased in density at the invasive margin.
Figure 16:
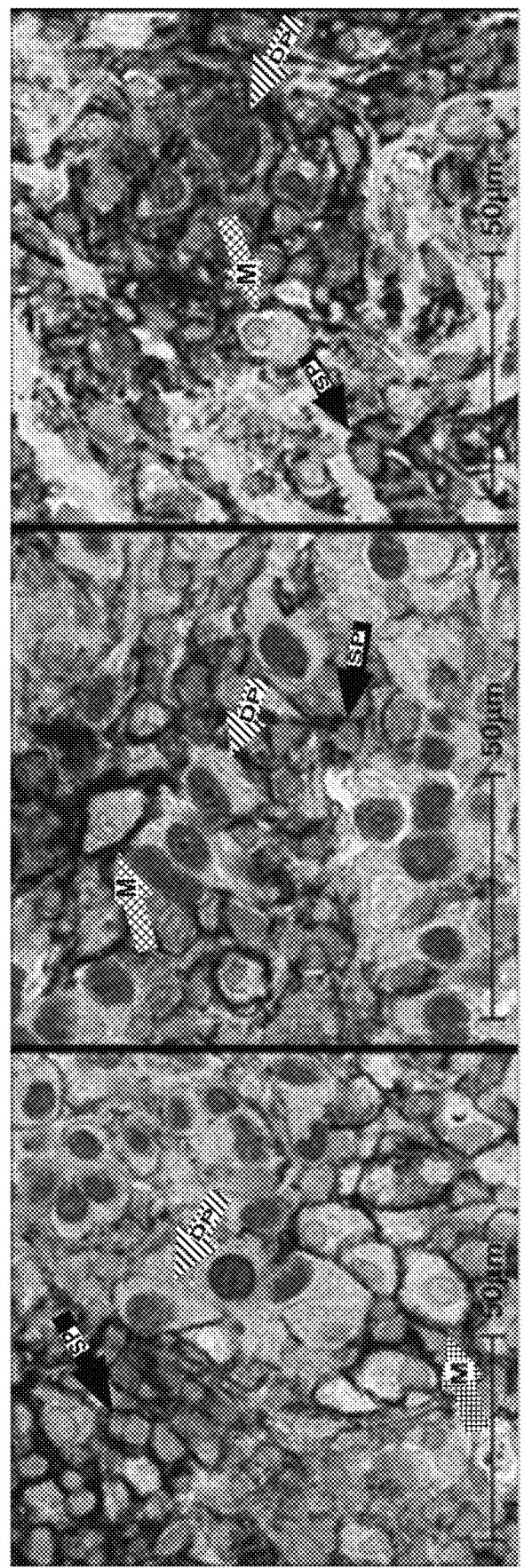
FIG. 16 is a set of digital photomicrographs showing multiplexed chromogenic staining for SOX-10 and PD-L1. Multiplexed chromogenic staining of SOX-10 (stained nucleus) and PD-L1 (stained membrane) was used to evaluate PD-L1 expression on melanoma cells, lymphocytes, and macrophages within the tumour microenvironment. SOX-10 is a transcription factor that is melanoma cell specific. Representative high power fields of double positive cells (DP arrows) show melanoma cells expressing PD-L1 and single positive PD-L1 cells comprising of lymphocytes (high nuclear:cytoplasmic ratio, SP arrows) and macrophages (low nuclear:cytoplasmic ratio, M arrows) in three responders from samples obtained during tumour regression. Magnification, ×40.

FIG. 13 is a series of digital images illustrating CD8+ T-cell kinetics within the tumour microenvironment in a serially sampled tumour responding to PD-1 blocking therapy. Example of radiographic, clinical, and CD8 IHC in a serially sampled melanoma tumour of the left chest wall that was obtained from a patient with a delayed response. On day +20, clinical and radiographic examinations indicated progressive disease; at a time when CD8 T-cells expression increased in density at the invasive margin.

Figure 14:
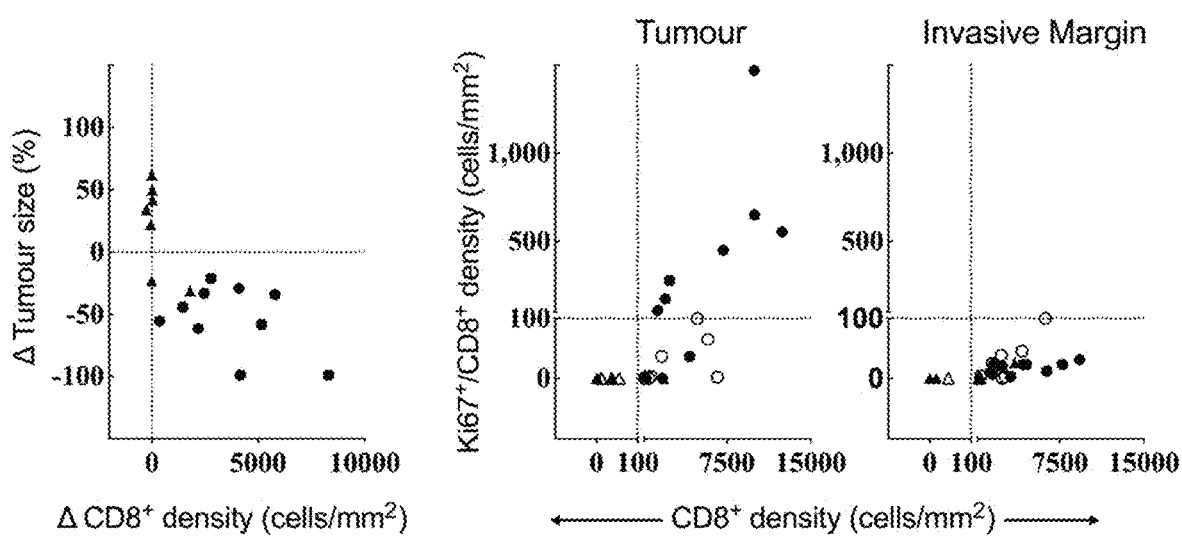
FIG. 14 is a series of graphs illustrating proliferation of CD8$^+$ T cells in regressing tumours. Left panel, Relationship of the change in CD8$^+$ cell density and best percent change in tumour size in serially sampled tumours that were assessed using quantitative immunohistochemistry and CT scan measurements (n=18, Spearman r=−0.75, P=0.0002). Center & right panels, CD8$^+$ cell density and Ki67$^+$/CD8$^+$ cell density in the Response group before treatment (n=11, empty circles) and during treatment (n=17, filled circles) and the Progression group before treatment (n=9, empty triangles), and during treatment (n=15, filled triangles).

FIG. 14 is a series of graphs illustrating proliferation of CD8+ T cells in regressing tumours. Left panel, Relationship of the change in CD8 cell density and best percent change in tumour size in serially sampled tumours that were assessed using quantitative immunohistochemistry and CT scan measurements (n=18, Spearman r=−0.75, P=0.0002). Center & right panels, CD8$^+$ cell density and Ki67$^+$/CD8+ cell density in the Response group before treatment (n=11, empty circles) and during treatment (n=17, filled circles) and the Progression group before treatment (n=9, empty triangles), and during treatment (n=15, filled triangles).

FIGS. 15A-15D show immunohistochemical analysis of Granzyme B and pSTAT1 expression before and during treatment in terms of clinical response. FIG. 15A, Representative examples of granzyme B expression according to clinical response. FIG. 15B, Samples collected during PD-1 blocking therapy were evaluated for Granzyme B signal (Response n=13, Progression n=12) using quantitative immunohistochemistry. **P<0.0001. FIG. 15C, Localization of CD8$^+$ and pSTAT1$^+$ cells in samples obtained before treatment from a responder, and two progressors (+/−a CD8 presence). The progressor with a moderate presence of CD8 cells did not show pSTAT1 expression in the area. FIG. 15D**, Using quantitative IHC analysis, the Response group was associated with significantly higher expression of pSTAT1$^+$ at the invasive margin before and during treatment (Response n=16, Progression n=18, p=0.002 for pre-treatment biopsies and Response n=13, Progression n=12, p<0.0001 for post treatment biopsies).

FIG. 15 is a set of digital photomicrographs showing multiplexed chromogenic staining for SOX-10 and PD-L1. Multiplexed chromogenic staining of SOX-10 (stained nucleus) and PD-L1 (stained membrane) was used to evaluate PD-L1 expression on melanoma cells, lymphocytes, and macrophages within the tumour microenvironment. SOX-10 is a transcription factor that is melanoma cell specific. Representative high power fields of double positive cells (DP arrows) show melanoma cells expressing PD-L1 and single positive PD-L1 cells comprising of lymphocytes (high nuclear:cytoplasmic ratio, SP arrows) and macrophages (low nuclear:cytoplasmic ratio, M arrows) in three responders from samples obtained during tumour regression. Magnification, ×40.

TABLE 2

Demographic & clinical characteristics of patients in Study & Validation cohorts

| Variable | Response | Progression | p-value* |
|---|---|---|---|
| UCLA Patients (N = 46) | N = 22$^\varepsilon$ | N = 24 | |
| Male (%) | 17 (74%) | 19 (79%) | >0.99 |
| Median Age (range) | 65 (45-90) | 64 (36-86) | 0.86$^\pounds$ |
| Median WBC Count (range) | 6.9 (3.9-21.3) | 7.1 (4.0-24.8) | 0.52 |
| Median Pre-TX Tumor Burden in cm (range)$^¥$ | 8.7 (1.1-32.2) | 7.9 (1.1-19.4) | 0.9$^\pounds$ |
| Metastatic Status | | | |
| M0 | 3 (13%) | 2 (8%) | 0.13$^\pounds$ |
| M1a | 4 (17%) | 2 (8%) | |

TABLE 2-continued

Demographic & clinical characteristics of patients in Study & Validation cohorts

| Variable | Response | Progression | p-value* |
|---|---|---|---|
| M1b | 7 (30%) | 6 (25%) | |
| M1c | 8 (35%) | 14 (58%) | |
| Dosing Regimen | | | |
| 10Q2W | 9 (39%) | 5 (21%) | 0.2 |
| 10Q3W | 8 (35%) | 8 (33%) | |
| 2Q3W | 5 (22%) | 11 (46%) | |
| BRAF Mutation | | | |
| Mutant (# not wild type) | 7 (30%) | 9 (38%) | 0.76 |
| Previous Treatment | | | |
| chemotherapy | 3 (13%) | 5 (21%) | 0.7 |
| BRAF or MEK inhibitor | 3 (13%) | 5 (21%) | 0.7 |
| immunotherapy | | | |
| ipilimumab | 8 (35%) | 13 (54%) | 0.25 |
| other | 7 (30%) | 9 (38%) | 0.76 |
| Pre TX Biopsy Location[¤] | | | |
| Subcutaneous | 14 (61%) | 11 (46%) | 0.02[£] |
| Liver | 0 | 8 (33%) | |
| Lung | 5 (22%) | 1 (4%) | |
| Other | 3 (13%) | 3 (13%) | |
| IGR Patients (N = 15) | N = 10 | N = 5 | |
| Median Age (range) | 55 (26-73) | 60 (38-61) | 0.77[£] |
| Male (%) | 4 (40%) | 2 (40%) | >0.99 |
| Metastatic Status | | | |
| M0 | 2 (20%) | 0 (0%) | 0.51[£] |
| M1a | 3 (30%) | 1 (20%) | |
| M1b | 0 (0%) | 1 (20%) | |
| M1c | 5 (50%) | 3 (60%) | |
| Dosing Regimen | | | |
| 10Q2W | 5 (50%) | 2 (40%) | 0.62 |
| 10Q3W | 3 (30%) | 3 (60%) | |
| 2Q3W | 2 (20%) | 0 (0%) | |
| BRAF Mutation | | | |
| Mutant (# not wild type) | 4 (40%) | 2 (40%) | >0.99 |
| Previous Treatment | | | |
| chemotherapy | 2 (20%) | 3 (60%) | 0.25 |
| BRAF or MEK inhibitor | 2 (20%) | 0 (0%) | 0.52 |
| immunotherapy | | | |
| ipilimumab | 4 (40%) | 2 (40%) | >0.99 |
| other | 1 (10%) | 1 (20%) | >0.99 |

*p-values calculated using Fisher's exact test

[£]p-values represent estimations using the non-parametric Kruskal-Wallis test

[¥]Tumor burden represents the sum of the longest measurement of identified target lesions as defined by RECIST 1.1 criteria.

[€] Stable disease (1 patient who experienced a 29% reduction in tumor size) included in the response group

[¤] One patient (Progression) did not receive a pre TX biopsy

TABLE 3

Anatomical location of biopsies performed before & during treatment. The anatomical locations that correspond with FIG. 9 are provided (Response n = 13, Progression n = 12 tumours biopsied at before and during aPD-1). The term lymph node/subcutaneous refers to a tumour identified as lymph node on radiographic imaging but with no evidence of lymph node architecture on histologic examination. Two out of the 25 patients had mets in transit which were distinct nodules that were <1 cm apart from each other at the time of biopsy.

| Patient | Baseline Biopsy | Post-Dosing Biopsy | Anatomical Location |
|---|---|---|---|
| 1 | duodenal lesion | duodenal lesion | Gastrointestinal |
| 2 | Segment 4 hepatic mass | Segment 4 hepatic mass | Liver |
| 3 | Segment 5 hepatic mass | Segment 5 hepatic mass | Liver |
| 4 | R. lower lobe lung mass | R. lower lobe lung mass | Lung |
| 5 | R. lower lobe lung mass | R. lower lobe lung mass | Lung |
| 6 | L. axillary mass | L. axillary mass | Lymph Node (Subcutaneous) |
| 7 | L. inguinal mass | L. inguinal mass | Lymph Node (Subcutaneous) |
| 8 | Right supraclavicular fossa mass | Right supraclavicular fossa mass | Lymph Node (Subcutaneous) |
| 9 | R. cervical neck mass | R. cervical neck mass | Lymph Node (Subcutaneous) |
| 10 | R. axillary mass | R. axillary mass | Lymph Node (Subcutaneous) |
| 11 | R. submandibular mass | R. submandibular mass | Lymph Node (Subcutaneous) |
| 12 | L. medial thigh | L. medial thigh | Subcutaneous/skin |
| 13 | L. lower back mass | L. lower back mass | Subcutaneous/skin |
| 14 | L. chest wall mass | L. chest wall mass | Subcutaneous/skin |
| 15 | Middle back mass | Middle back mass | Subcutaneous/skin |
| 16 | L. face mass | L. face mass | Subcutaneous/skin |
| 17 | L. scapula mass | L. scapula mass | Subcutaneous/skin |
| 18 | L. forearm mass | L. forearm mass | Subcutaneous/skin |
| 19 | L. popliteal mass | L. popliteal mass | Subcutaneous/skin |
| 20 | L. lower abdomen mass | L. lower abdomen mass | Subcutaneous/skin |
| 21 | L. lower abdomen mass | L. lower abdomen mass | Subcutaneous/skin |
| 22 | L. scalp mass | L. scalp mass | Subcutaneous/skin |
| 23 | L. anterolateral leg mass | L. anterolateral leg mass | Subcutaneous/skin |
| 24 | L. upper arm (mets in transit) | L. upper arm (mets in transit) | Subcutaneous/skin (mets in transit) |
| 25 | lower leg (mets in transit) | lower leg (mets in transit) | Subcutaneous/skin (mets in transit) |

TABLE 4

CD8 and CD4 expression before treatment in terms of clinical response to pembrolizumab and previous treatment with ipilimumab (anti-CTLA4) No significant association was found with previous treatment with ipilimumab and expression levels of the markers prior to receiving aPD-1 in terms of treatment outcome.

| | Ipilimumaub Treatment History | | |
|---|---|---|---|
| Variable | Response (Naïve) vs. Response (Treated) | Response (Naïve) vs. Progression (All) p-value* | Response (Naïve) vs. Progression (Treated) |
| Tumor density (cells/mm$^2$) | | | |
| CD8 | 0.0513 | <0.0001 | 0.0019 |
| CD4 | 0.2453 | 0.3453 | 0.3948 |

TABLE 4-continued

CD8 and CD4 expression before treatment in terms of clinical response to pembrolizumab and previous treatment with ipilimumab (anti-CTLA4) No significant association was found with previous treatment with ipilimumab and expression levels of the markers prior to receiving aPD-1 in terms of treatment outcome.

| | Ipilimumaub Treatment History | | |
|---|---|---|---|
| Variable | Response (Naïve) vs. Response (Treated) | Response (Naïve) vs. Progression (All) p-value* | Response (Naïve) vs. Progression (Treated) |
| Invasive Margin density (cells/mm²) | | | |
| CD8 | 0.0170 | <0.0001 | 0.0016 |
| CD4 | 0.2051 | 0.4183 | 0.4316 |

*p-values represent estimations using the non-parametric Mann-Whitney test

TABLE 5

ROC curve analysis for clinical response based on pre-treatment CD8+ and CD4+ cells The area under the ROC curve (AUC) was used to measure response prediction performance for pre-treatment CD8+ and CD4+ cell densities (cells/mm²).

| Variable | N | AUC (95% CI) | p-value |
|---|---|---|---|
| Tumor | | | |
| CD8+ Density | 45 | .91 (0.81, 1.00) | <0.001 |
| CD4+ Density | 37 | .66 (0.48, 0.84) | 0.095 |
| Invasive Margin | | | |
| CD8+ Density | 45 | .94 (0.88, 1.00) | <0.001 |
| CD4+ Density | 37 | .66 (0.48, 0.84) | 0.095 |

P-values were computed on the basis of the Wilcoxon rank sum statistic.

TABLE 6

Performance of a model for clinical response using CD8+ (cells/mm²) A logistic regression model was constructed using pre-treatment CD8+ (cells/mm²) versus the outcome of clinical response (Response vs. Progression) using the study cohort. This fixed model was then applied to the CD8+ density measurements in the validation cohort to compute predicted probabilities of response to treatment.

| Patient ID | CD8+ Density, Before Tx (Invasive Margin) | Predicted Probability of Response (Logistic Model) | Blinded Prediction | True Clinical Response (RECIST 1.1) |
|---|---|---|---|---|
| IGR - A | 58 | 0.35 | Progression | Progression |
| IGR - B | 159 | 0.37 | Progression | Progression |
| IGR - C | 329 | 0.40 | Progression | Progression |
| IGR - D | 341 | 0.41 | Progression | Progression |
| IGR - E | 2120 | 0.75 | Response | Stable |
| IGR - F | 5466 | 0.98 | Response | Progression |
| IGR - G | 2211 | 0.76 | Response | Response |
| IGR - H | 3810 | 0.92 | Response | Response |
| IGR - I | 4294 | 0.95 | Response | Response |
| IGR - J | 4948 | 0.97 | Response | Response |
| IGR - K | 5565 | 0.98 | Response | Response |
| IGR - L | 6004 | 0.99 | Response | Response |
| IGR - M | 5951 | 0.99 | Response | Complete Response |
| IGR - N | 7230 | 0.99 | Response | Complete Response |
| IGR - O | 6320 | 0.99 | Response | Complete Response |

References Cited in Example 4

1 Topalian, S. L. et al. N. Engl. J. Med. 366, 2443-2454 (2012).
2 Brahmer, J. R. et al. N. Engl. J. Med. 366, 2455-2465 (2012).
3 Hamid, O. et al. N. Engl. J. Med. 369, 134-144, doi: 10.1056/NEJMoa1305133 (2013).
4 Wolchok, J. D. et al. N. Engl. J. Med. 369, 122-133, doi:10.1056/NEJMoa1302369 (2013).
5 Topalian, S. L. et al. J Clin Oncol 32, 1020-1030, doi:10.1200/JCO.2013.53.0105 (2014).
6 Pardoll. D. M. Nature Reviews Cancer 12, 252-264 (2012).
7 Spranger, S. et al. Sci Transl Med 5, 200ra116, doi: 10.1126/scitranslmed.3006504 (2013).
8 Robert, C. et al. Lancet, doi:10.1016/S0140-6736(14) 60958-2 (2014).
9 Parsa, A. T. et al. Nat Med 13, 84-88, doi:10.1038/nm1517 (2007).
10 Atefi, M. et al. Clin. Cancer Res. 20, 3446-3457, doi: 10.1158/1078-0432.CCR-13-2797 (2014).
11 Bald, T. et al. Cancer discovery 4, 674-687, doi:10.1158/ 2159-8290.CD-13-0458 (2014).
12 Duraiswamy, J., et al. Cancer Res 74, 633-634; discussion 635, doi:10.1158/0008-5472.CAN-13-2752 (2014).
13 Galon, J. et al. Science 313, 1960-1964, doi:10.1126/ science.1129139 (2006).
14 Pages, F. et al. N. Engl. J. Med. 353, 2654-2666, doi:10.1056/NEJMoa051424 (2005).
15 Taube, J. M. et al. Clin. Cancer Res., doi:10.1158/1078-0432.CCR-13-3271 (2014).
16 Robins, H. S. et al. Blood 114, 4099-4107, doi:10.1182/ blood-2009-04-217604 (2009).
17 Carlson, C. S. et al. Nature communications 4, 2680, doi:10.1038/ncomms3680 (2013).
18 Zhang, L. et al. N. Engl. J. Med. 348, 203-213, doi: 10.1056/NEJMoa020177 (2003).
19 Ribas, A., et al. J Clin Oncol 32, 5s (2014).
20 Wolchok, J. D. et al. Clin. Cancer Res. 15, 7412-7420, doi:10.1158/1078-0432.CCR-09-1624 (2009).

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for improving treatment outcome by treating a subject with a monotherapy or combination therapy based on a tumor microenvironment of a melanoma of the subject, the method comprising:
(a) assessing a location of target cells and T lymphocytes in an invasive margin of a melanoma sample isolated from the subject, wherein the target cells express CD11c, or CD163, wherein the assessing comprises contacting the biological sample with an antibody that specifically binds to CD163 or CD11c;

(b) measuring, by a computer processor, a density of the target cells and the T lymphocytes in the invasive margin of the melanoma sample;
(c) determining, by a computer processor, a proximity between the target cells and the T lymphocytes in the invasive margin of the melanoma sample;
(d) generating, by a computer processor, an overall score based at least in part on parameters (a) to (c);
(e) comparing the overall score to a reference; and
(1) if the overall score is equal to or greater than the reference:
   a) administering to the subject an effective amount of a single agent that blocks PD-1/PD-L1/PD-L2 pathway; or
   b) if the subject is initially treated with an anti-PD-1/PD-L1/PD-L2 agent, continuing administration of the anti-PD-1/PD-L1/PD-L2 agent; or
   c) if the subject is initially provided combination therapy, discontinuing administration of an antitumor agent and continuing administration of an agent that blocks PD-1/PDL1/PD-L2 pathway; or
(2) if the overall score is less than the reference score:
   a) administering to the subject an effective amount of an agent that blocks PD-1/PDL1/PD-L2 pathway and an effective amount of an antitumor agent; or
   b) if the subject is initially treated with an anti-PD-1/PD-L1/PD-L2 agent, administering to the subject an effective amount of an antitumor agent, and administering the anti-PD-1/PD-L1/PD-L2 agent or a different agent that blocks PD-1/PD-L1/PD-L2 pathway; or
   c) if the subject is initially provided combination therapy, administering to the subject an agent or a different agent that blocks PD-1/PD-L1/PD-L2 pathway, and administering an antitumor agent.

2. The method of claim 1, wherein the melanoma sample is obtained from the subject prior to treatment or during treatment.

3. The method of claim 1, further comprising determining a density score for the density of the target cells in the melanoma sample or a proximity score for the proximity between the target cells in the melanoma sample, and wherein:
the density score is determined based at least in part on weighting of the density of particular types of the target cells in the melanoma sample;
the proximity score is determined based at least in part on weighting of the proximity between particular types of the target cells of interest in the melanoma sample; and
the overall score is determined based at least in part on weighting of the density score or the proximity score.

4. The method of claim 3, wherein the density score, the proximity score or the overall score, or any combination or all thereof, is adjusted based on:
(1) whether the melanoma sample is obtained from the subject prior to treatment or during treatment; or
(2) a particular type of tumor the subject has; or
(3) location of primary tumor or location of any metastatic tumor; or
(4) ethnicity or race, gender, age, body mass index, diet, risk factors, medical history or overall health, or any combination or all thereof, of the subject; or
(5) therapeutic outcome of treatment of other subjects with a particular type of tumor using a particular single agent that blocks PD-1/PD-L1/PD-L2 pathway, or using a particular anti-PD-1/PDL1/PD-L2 agent and a particular additional antitumor agent (combination therapy); or
(6) any combination, or all, of (1) to (5).

5. The method of claim 1, wherein the target cells express biomarkers selected from the group consisting of CD4, CD8, CD11 b, CD15, CD16, CD19, CD25, CD56, CD68, CD80, CD123, CD138, CTLA-4, Foxp3, granzyme B, HLA-A, HLA-B, HLA-C, HLA-DR, IgG-k, IgG-A, Ki67, LDH, MPO, OX40 (CD134), PD-1, PD-L1, PD-L2 and pSTAT1.

6. The method of claim 5, wherein the target cells express at least 5, 10, 15, 20 or 25, or all, of the biomarkers recited in claim 5.

7. The method of claim 1, wherein the one or more biomarkers, or the target cells expressing the one or more biomarkers, are detected by staining using antibodies that specifically bind to the one or more biomarkers.

8. The method of claim 1, wherein the melanoma sample comprises tissue or blood.

9. The method of claim 1, wherein:
(1) if the overall score is equal to or greater than a threshold score, the overall score indicates or predicts that the subject will respond to treatment with a single agent that blocks PD-1/PD-L1/PD-L2 pathway; or
(2) if the overall score is less than a threshold score, the overall score indicates or predicts that the subject will not respond to treatment with a single agent that blocks PD-1/PD-L1/PD-L2 pathway.

10. The method of claim 1, which is performed:
(1) on a melanoma sample obtained from the subject prior to treatment to guide decision on selection of treatment with a single agent that blocks PD-1/PD-L1/PD-L2 pathway, or with an agent that blocks PD-1/PD-L1/PD-L2 pathway and at least one other antitumor agent; and
(2) on at least one melanoma sample obtained from the subject during treatment to monitor response of the subject to a current treatment regimen and to guide decision on selection of treatment with a single-agent PD-1/PD-L1/PD-L2 blockade therapy or with a combination therapy.

11. The method of claim 9, which is used to stratify subjects as responders or non-responders to PD-1/PD-L1/PD-L2 blockade therapy and to select subjects in clinical practice, in a clinical trial, or in drug discovery or development, whether relating to a single-agent therapy or a combination therapy.

12. The method of claim 1, which is used to guide or effect treatment decision in clinical practice, in a clinical trial, or in drug discovery or development, whether relating to a single-agent therapy or a combination therapy.

13. The method of claim 1, wherein the overall score correlates to a probability that, or predicts whether, the subject will respond to treatment with a particular single agent that blocks PD-1/PD-L1/PD-L2 pathway, or with a particular anti-PD-1/PD-L1/PD-L2 agent and a particular additional antitumor agent.

14. The method of claim 1, wherein the agent that blocks PD-1/PD-L1/PD-L2 pathway is selected from the group consisting of nivolumab (BMS-936558, MDX-1106 or ON0-4538), pembrolizumab (lambrolizumab or MK-3475), pidilizumab (CT-011), MEDI-0680 (AMP-514), AMP-224, BMS-936559 (MDX-1105), MEDI-4736, MPDL3280A (RG7446), MSB0010718C, and analogs, derivatives, fragments and salts thereof.

15. The method of claim 1, which is implemented with a computer system comprising at least one processor, wherein the computer system is configured or provided with algorithms, instructions or codes for performing the method which are executable by the at least one processor.

16. The method of claim 1, wherein the overall score is less than the reference score and the subject is administered a combination therapy.

17. The method of claim 1, wherein the measured density of the target cells and the T lymphocytes in the invasive margin of the melanoma sample comprises about 1000 cells per mm$^2$ or more.

* * * * *

UNITED STATES PATENT AND TRADEMARK OFFICE
CERTIFICATE OF CORRECTION

PATENT NO. : 11,275,080 B2  
APPLICATION NO. : 14/933853  
DATED : March 15, 2022  
INVENTOR(S) : Tumeh et al.

Page 1 of 1

It is certified that error appears in the above-identified patent and that said Letters Patent is hereby corrected as shown below:

In the Claims

Claim 1, Line 9, delete "biological" and insert --melanoma--

Claim 5, Line 2, "biomarkers" should read --one or more biomarkers--

Claim 6, Line 2, "biomarkers" should read --one or more biomarkers--

Claim 7, Line 1, "claim 1" should read --claim 5--

Signed and Sealed this  
Twenty-ninth Day of November, 2022

Katherine Kelly Vidal  
*Director of the United States Patent and Trademark Office*